(12) United States Patent
Penninger et al.

(10) Patent No.: US 7,794,707 B2
(45) Date of Patent: Sep. 14, 2010

(54) ACE2 ACTIVATION FOR TREATMENT OF HEART, LUNG AND KIDNEY DISEASE AND HYPERTENSION

(75) Inventors: Joseph Penninger, Vienna (AT); Michael A. Crackower, Moonpark, CA (US)

(73) Assignee: University Health Network, Toronto, Ontario (CA)

( * ) Notice: Subject to any disclaimer, the term of this patent is extended or adjusted under 35 U.S.C. 154(b) by 0 days.

(21) Appl. No.: 10/518,599

(22) PCT Filed: Jun. 19, 2003

(86) PCT No.: PCT/CA03/00882

§ 371 (c)(1), (2), (4) Date: May 31, 2005

(87) PCT Pub. No.: WO04/000367

PCT Pub. Date: Dec. 31, 2003

(65) Prior Publication Data

US 2005/0251873 A1    Nov. 10, 2005

Related U.S. Application Data

(60) Provisional application No. 60/389,709, filed on Jun. 19, 2002.

(51) Int. Cl.
A61K 38/43 (2006.01)
C07K 17/00 (2006.01)
(52) U.S. Cl. ..................... 424/94.1; 530/350
(58) Field of Classification Search ............... 516/316, 516/350; 530/350; 424/94.1
See application file for complete search history.

(56) References Cited

U.S. PATENT DOCUMENTS

| | | | |
|---|---|---|---|
| 4,708,871 A | 11/1987 | Geysen et al. | 424/186.1 |
| 5,399,346 A | 3/1995 | Anderson et al. | 424/93.21 |
| 5,436,146 A | 7/1995 | Shenk et al. | 435/457 |
| 5,529,774 A | 6/1996 | Barba et al. | 424/93.21 |
| 5,547,932 A | 8/1996 | Curiel et al. | 435/456 |
| 5,645,829 A | 7/1997 | Shockley et al. | 424/93.21 |
| 5,656,465 A | 8/1997 | Panicali et al. | 435/456 |
| 5,670,488 A | 9/1997 | Gregory et al. | 514/44 |
| 5,672,344 A | 9/1997 | Kelley et al. | 424/93.2 |
| 5,736,337 A | 4/1998 | Avruch et al. | 435/7.1 |
| 5,741,486 A | 4/1998 | Pathak et al. | 424/93.21 |
| 5,767,075 A | 6/1998 | Avruch et al. | 514/12 |
| 5,792,851 A | 8/1998 | Schuster et al. | 536/23.5 |
| 5,851,788 A | 12/1998 | Fukuda et al. | 435/29 |
| 6,071,890 A | 6/2000 | Scheule et al. | 514/44 |
| 6,174,871 B1 | 1/2001 | Hammond et al. | 514/44 |
| 6,194,556 B1 * | 2/2001 | Acton et al. | 536/23.2 |
| 6,224,584 B1 | 5/2001 | Mach et al. | 604/508 |
| 6,306,830 B1 | 10/2001 | Hammond et al. | 514/44 |
| 6,322,536 B1 | 11/2001 | Rosengart et al. | 604/164.01 |
| 6,632,830 B1 * | 10/2003 | Acton et al. | 514/365 |

FOREIGN PATENT DOCUMENTS

| | | |
|---|---|---|
| WO | WO 00/18899 | 4/2000 |
| WO | WO 01/29040 | 4/2001 |
| WO | WO 02/12471 | * 2/2002 |

OTHER PUBLICATIONS

Crackower, M.A et al ACE2: A novel candidate gene for hypertension. American Journal of Hypertension, (Apr. 2001), 14 (4) Part 2, pp. 78A. Sixteenth Annual Scientific Meeting of the American Society of Hypertension. San Francisco, California, USA. May 15-19, 2001 (abstract).*
Goodman & Gilman's The Pharmacological basis of Therapeutics, McGraw-Hill, New York, NY. pp. 77-101.*
Verma and Somia (1997) Nature 389:239-242.*
Pfeifer and Verma (2001) Annual Review of Genomics and Human Genetics.2: 177-211.*
Filion et al Br J Pharmacol. 1997;122(3): 551-557.*
Davis et al Current Opinion in Biotechnology 2002, 13:128-131.*
Scientific Considerations Related to Developing Follow-on Protein Products. Division of Dockets Management U.S. Food and Drug Administration Nov. 12, 2004, pp. 1-12.*
Vile et al Gene Therapy, 2000, 7: 2-8.*
Holschneider et al. Int J Devl Neuroscience, 2000, 18: 615-618.*
Tailleux et al Trends Pharmacol Sci. 2003;24(10):530-4.*
Altschul et al., "Basic local alignment search tool," *J. Mol. Biol.*, 215:403-410,1990.
Altschul et al., "Gapped blast and psi-blast: a new generation of protein database search programs," *Nucleic Acids Research*, 25:3389-3402,1997.
Andreoli et al., *Essentials of Medicine*, W.B. Saunders Company, 3:40-243,1993.
Carretero, et al., "Essential hypertension," *Circulation*, 101:329-335,2000.
Christian et al., "Simplified methods for construction, assessment and rapid screening of peptide libraries in bacteriophage," *J. Mol. Biol.*, 227:711-718.
Corvol et al., "Peptidyl-dipeptidase a/angiotensin i-converting enzyme," *Handbook of Proteolytic Enzyme $2^{nd}$ Edn*, Elsevier Ltd., 82:332-346.
Corvol et al., "Peptidyl-dipeptidase a/angiotensin i-converting enzyme," *Clan MA-M2*, 359:1066-1076.
Cwirla et al., "Peptides on phage: a vast library of peptides for identifying ligands," *Biochemistry*, 87:6378-6382.
Donoghue et al., "A novel angiotensin-converting enzyme-related carboxypeptidase (ace2) converts angiotensin to angiotensin 1-9," *Circ. Res.*, 87:1-9,2000.
Elkind et al., "Stroke risk factors and stroke prevention," *Seminars in Neurology*, 18:429-439,1998.

(Continued)

*Primary Examiner*—Tekchand Saidha
(74) *Attorney, Agent, or Firm*—Fulbright & Jaworski LLP

(57) ABSTRACT

The invention relates to ACE2 activating compounds for prevention and treatment of cardiovascular disease, kidney disease, lung disease and hypertension. The invention also includes methods of diagnosing cardiovascular disease, kidney disease, lung disease and hypertension by measuring ACE2 expression or nucleotide polymorphism analysis.

6 Claims, 19 Drawing Sheets

OTHER PUBLICATIONS

Enseleit et al., "Vascular protective effects of angiotensin converting enzyme inhibitors and their relation to clinical events," *Journal of Cardiovascular Pharmacology*, 37:S21-S30,2001.

Esther et al., "Mice lacking angiotensin-converting enzyme have low blood pressure, renal pathology, and reduced mal fertility," *Laboratory Investigation*, 74:953-965,1996.

Figlin et al., "Technology evaluation: interleukin-2 gene therapy for the treatment of renal cell carcinoma," *Molecular Thereutics*, 1:271-278.

Franz et al., "Analysis of tissue-specific gene delivery by recombinant adenoviruses containing cardiac-specific promoters," *Cardiovascular Research*, 35:560-566,1997.

Garg, et al, "Overview of randomized trials of angiotensin-converting enzyme inhibitors on morality and morbidity in patients with heart failure," *Jama*, 273:1450-1456,1995.

Giordano et al., "A cardiac myocyte vascular endothelial growth factor paracrine pathway is required to maintain cardiac function," *PNAS*, 98:5780-5785,2001.

Gish et al., "Identification of protein coding regions by database similarity search," *Nature Genetics*, 3:266-272,1993.

Herold et al,. "Herpes simplex virus as a model vector system for gene therapy in renal disease," *Kidney International*, 61:S3-S8,2002.

Heusch, "Hibernation Mycardium," *Physiological Reviews*, 78:1055-1085,1998.

Hilbert et al., "Chromosomal mapping of two genetic loci associated with blood-pressure regulation in hereditary hypertensive rats," *Nature*, 353:521-528,1991.

Hollenberg, N.K. et al., Angiotensin converting enzyme inhibiton and the kidney,: *Cardiology*, 3:S19-S29,1988.

Jacob, Howard, "Physiological Genetics," *Clinical and Experimental Pharmacology and Physiology and Physiology*, 26:530-535,1999.

Keitzmann et al., "Induction of the plasminogen activator inhibitor-1 gene expression by mild hypoxia via a hypoxia response element binding the hypoxia-inducible factor-1 in rat hepatocytes," *Blood*, 94:4177-4185,1999.

Kloner et al., "Medical and cellular implication of stunning, hibernation, and preconditioning," *Circulation*, 97:1848-1867,1998.

Klöting et al., "Metabolic features of newly established congenic diabetes-prone bb.shr rat strains," *Life Science*, 62:973-979,1998.

Kong et al., "Opgl is a key regulator of osteoclastogenesis, lymphocyte development and lymph-node organogenesis," *Nature*, 397:315-323,1999.

Krege et al., "Male-female differences in fertility and blood pre3ssure in ace-deficient mice," *Nature*, 375:146-148,1995.

Langer et al., "Adeno-associated virus gene transferred into renal cells: potential for in vivo gene delivery," *Exp. Nephrol.*, 6:189-194,1998.

Lien et al., "Gene therapy for renal disease," *Kidney International*, 52:S85-S88,1997.

Madden et al., "Application of network blast server," *Methods in Enzymology*, 266:131-141,1996.

Murphy et al., "Transgenic mouse model of stunned myocardium," *Science*, 287:488-490,2000.

Ohno et al., "Cell-specific targeting of sindbis virus vectors displaying igg-binding domains of protein a," *Nature Biotechnology*, 15:763-767,1997.

Phillips et al., "Vigilant vector: heart-specific promoter in an adeno-associated virus vector for cardioprotection," *Hypertension*, 39:651-655,2002.

Rapp, John P., "Genetic Analysis of Inherited Hypertension in the rat," *Physiological Reviews*, 80:135-172, 2000.

*Remington: The Science and Practice of Pharmacy*,Lippincott Williams and Wilkins, 14:186-200,Unknown Year.

Risch et al., "No excess of homozygosity at loci used for dna fingerprinting," *Science*, 249:1416-1420,1990.

Rothmann et al., "Heart muscle-specific gene expression using replication defective recombinant adenovirus," *Gene Therapy*, 3:919-926,1996.

Scott-Taylor et al., "Adenovirus facilitated infection of human cells with ecotropic retrovirus," *Gene Therapy*, 5:621-629,1998.

Skeggs et al., "The biochemistry of the renin-angiotensin system," *Adv Exp Med Biol.* 130:1-27,1980.

Sowter et al., "Hif-1-dependent regulation of hypoxic induction of the cell death factors bnip3 and nix in human tumors," *Cancer Research*, 61:6669-6673,2001.

Stoll et al., "A genomic-systems biology map for cardiovascular function," *Science*, 294:1723-1726,2001.

Tanimoto et al., "Angiotensinogen-deficient mice with hypotension," *The Journal of Biological Chemistry*, 269:31334-31337,1994.

Taylor et al., "The acer gene of drosophila codes for an angiotensin-converting enzyme homologue," *Gene*, 181:191-197,1996.

Tipnis et al., "A human homolog of angiotensin-converting enzyme," *The Journal of Biological Chemistry*, 275:33238-33243,2000.

Varda-Bloom et al., "Tissue-specific gene therapy directed to tumor angiogenesis," *Gene Therapy*, 8:819-827,2001.

Vickers et al., "Hydrolysis of biological peptides by human angiotesin-converting enzyme-related carboxypeptidase," *The Journal of Biological Chemistr*, 277:14838-14843,2002.

Weiss et al., "Angiotensin II and atherosclerosis," *Am. J. Hum. Genet.*, 87:52C-32C, 2001.

Wickengarden et al., "Targeted expression of a dominat-negative $k_v$ 4.2 $k^+$channel subunit in the mouse heart" *Circulation Research*, 85:1067-1076,1999.

Wuyts et al., "Angiotensin i-converting enzyme insertion/deletion polymorphism: clinical implications," *Acta Clinica Belgica*, 52-6:338-349,1997.

Wyngaarden et al., *Cecil Textbook of Medicine*, W.B. Saunders Company, 2:1272-1281,1992.

Yagil et al., "Role of chromosome x in the sabra rat model of salt-sensitive hypertension," *Hypertension*, 33:261-265,1999.

Yangil et al., "Development, genotype and phenotype of a new colony of that sabra hypertension prone (sbh/y) and resistant (sbn/y) rat model of salt sensitivity and resistance," *Journal of Hypertension*, 14:1175-1182, 1996.

Yusuf et al., "Global burden of cardiovascular disease," *Circulation*, 104:2746-2753,2001.

Zhang et al., "Powerblast: a new network blast application for interactive or automated sequence analysis and annotation," *Genome Research*, 7:649-656,1997.

Zvaritch et al., "The transgenic expression of highly inhibitory monomeric forms of phospholamban in mouse heart impairs cardiac contractility," *The Journal of Biological Chemistry*, 275:1485-14991,2000.

BLASTP 2.2.14 search for peptide DRVYTHPF Angiotensin II in all GenBank databases, May 7, 2006.

Imai et al., "Angiotensin-converting enzyme 2 protects from severe acute lung failure," *Nature*, 436:112-116, 2005.

Kuba et al., "A crucial role of angiotensin converting enzyme 2 (ACE2) in SARS coronavirus-induced lung injury," *Nature Medicine*, 11(8):875-879, 2005.

Macours et al., "Structure, evolutionary conservation, and functions of angiotensin- and endothelin-converting enzymes," *International Review of Cytology*, 239:47-97.

Crackower et al., "Angiotensin-converting enzyme 2 is an essential regulator of heart function," *Nature*, 417:822-828, 2002.

Donoghue et al, "A novel angiotensin-converting enzyme-related carboxypeptidase (ACE2) converts angiotensin I to angiotensin 1-9," *Circulation Research*, 87:e1-e9, 2000.

Gramatikoff "Angiotensin-converting enzyme 2 regulates heart function," Database Biocarta, 2002.

Yagil et al., "Role of chromosome X in the sagra rat model of salt-sensitive hypertension," *Hypertension*, 33:261-265, 1999.

Japanese Office Action, issued in Japanese Application No. 2004-514460, dated Nov. 17, 2009.

Turner and Hooper, "The angiotensin-converting enzyme gene family: genomics and pharmacology," *Trends in Pharmacological Sciences*, 23:177-183, 2002.

\* cited by examiner

Figure 5c, 5d
c
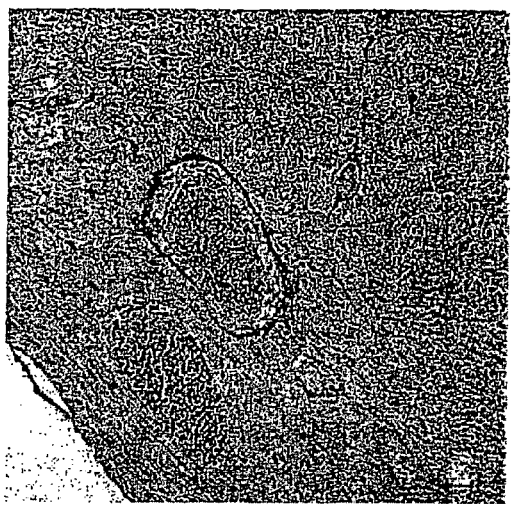
ace2+/y
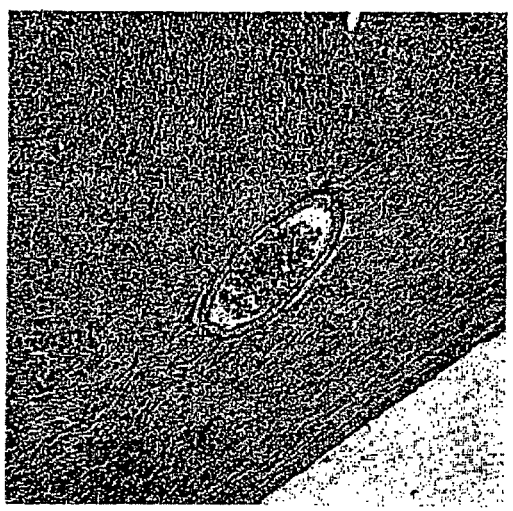
ace2-/y
d
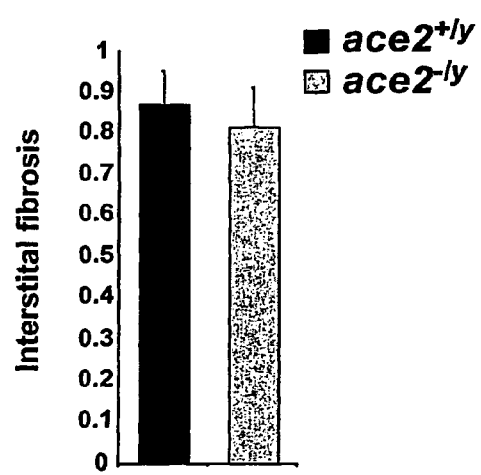

Figure 10a

```
   1 cgcccaaccc aagttcaaag gctgataaga gagaaaatct catgaggagg ttttagtcta
  61 gggaaagtca ttcagtggat gtgatcttgg ctcacagggg acgatgtcaa gctcttcctg
 121 gctccttctc agccttgttg ctgtaactgc tgctcagtcc accattgagg aacaggccaa
 181 gacattttg gacaagttta accacgaagc cgaagacctg ttctatcaaa gttcacttgc
 241 ttcttggaat tataacacca atattactga agagaatgtc caaaacatga ataatgctgg
 301 ggacaaatgg tctgcctttt taaaggaaca gtccacactt gcccaaatgt atccactaca
 361 agaaattcag aatctcacag tcaagcttca gctgcaggct cttcagcaaa atgggtcttc
 421 agtgctctca gaagacaaga gcaaacggtt gaacacaatt ctaaatacaa tgagcaccat
 481 ctacagtact ggaaaagttt gtaacccaga taatccacaa gaatgcttat tacttgaacc
 541 aggtttgaat gaaataatgg caaacagttt agactacaat gagaggctct gggcttggga
 601 aagctggaga tctgaggtcg gcaagcagct gaggccatta tatgaagagt atgtggtctt
 661 gaaaaatgag atggcaagag caaatcatta tgaggactat ggggattatt ggagaggaga
 721 ctatgaagta aatggggtag atggctatga ctacagccgc ggccagttga ttgaagatgt
 781 ggaacatacc tttgaagaga ttaaaccatt atatgaacat cttcatgcct atgtgagggc
 841 aaagttgatg aatgcctatc cttctatat cagtccaatt ggatgcctcc ctgctcattt
 901 gcttggtgat atgtgggta gattttggac aaatctgtac tctttgacag ttcccttttgg
 961 acagaaacca aacatagatg ttactgatgc aatggtggac caggcctggg atgcacagag
1021 aatattcaag gaggccgaga agttctttgt atctgttggt cttcctaata tgactcaagg
1081 attctgggaa aattccatgc taacggaccc aggaaatgtt cagaaagcag tctgccatcc
1141 cacagcttgg gacctgggga agggcgactt caggatcctt atgtgcacaa aggtgacaat
1201 ggacgacttc ctgacagctc atcatgagat ggggcatatc cagtatgata tggcatatgc
1261 tgcacaacct tttctgctaa gaaatggagc taatgaagga ttccatgaag ctgttgggga
1321 aatcatgtca ctttctgcag ccacacctaa gcatttaaaa tccattggtc ttctgtcacc
1381 cgattttcaa gaagacaatg aaacagaaat aaacttcctg ctcaaacaag cactcacgat
1441 tgttgggact ctgccattta cttacatgtt agagaagtgg aggtggatgg tctttaaagg
1501 ggaaattccc aaagaccagt ggatgaaaaa gtggtgggag atgaagcgag atagttgg
1561 ggtggtggaa cctgtgcccc atgatgaaac atactgtgac cccgcatctc tgttccatgt
1621 ttctaatgat tactcattca ttcgatatta cacaaggacc ctttaccaat tccagtttca
1681 agaagcactt tgtcaagcag ctaaacatga aggccctctg cacaaatgtg acatctcaaa
1741 ctctacagaa gctggacaga aactgttcaa tatgctgagg cttggaaaat cagaccctg
1801 gaccctagca ttggaaaatg ttgtaggagc aaagaacatg aatgtaaggc cactgctcaa
1861 ctactttgag cccttattta cctggctgaa agaccagaac aagaattctt ttgtgggatg
1921 gagtaccgac tggagtccat atgcagacca aagcatcaaa gtgaggataa gcctaaaatc
1981 agctcttgga gataaagcat atgaatggaa cgacaatgaa atgtacctgt tccgatcatc
2041 tgttgcatat gctatgaggc agtacttttt aaaagtaaaa aatcagatga ttcttttggg
2101 ggaggaggat gtgcgagtgg ctaatttgaa accaagaatc tcctttaatt tctttgtcac
2161 tgcacctaaa aatgtgtctg atatcattcc tagaactgaa gttgaaaagg ccatcaggat
2221 gtcccggagc cgtatcaatg atgctttccg tctgaatgac aacagcctag agtttctggg
2281 gatacagcca acacttggac ctcctaacca gccccctgtt ccatatggc tgattgtttt
2341 tggagttgtg atgggagtga tagtggttgg cattgtcatc ctgatcttca ctgggatcag
2401 agatcggaag aagaaaaata agcaagaag tggagaaaat ccttatgcct ccatcgatat
2461 tagcaaagga gaaaataatc caggattcca aacactgat gatgttcaga cctccttta
2521 gaaaaatcta tgtttttcct cttgaggtga ttttgttgta tgtaaatgtt aatttcatgg
2581 tatagaaaat ataagatgat aaagatatca ttaaatgtca aaactatgac tctgttcaga
2641 aaaaaattg tccaaagaca acatggccaa ggagagagca tcttcattga cattgctttc
2701 agtatttatt tctgtctctg gatttgactt ctgttctgtt tcttaataag gatttgtat
2761 tagagtatat tagggaaagt gtgtatttgg tctcacaggc tgttcaggga taatctaaat
2821 gtaaatgtct gttgaatttc tgaagttgaa aacaaggata tcattgga gcaagtgttg
2881 gatcttgtat ggaatatgga tggatcactt gtaaggacag tgcctgggaa ctggtgtagc
2941 tgcaaggatt gagaatggca tgcattagct cactttcatt taatccattg tcaaggatga
```

(continued next page)

Figure 10a continued

```
3001 catgctttct tcacagtaac tcagttcaag tactatggtg atttgcctac agtgatgttt
3061 ggaatcgatc atgctttctt caaggtgaca ggtctaaaga gagaagaatc cagggaacag
3121 gtagaggaca ttgcttttc  acttccaagg tgcttgatca acatctccct gacaacacaa
3181 aactagagcc aggggcctcc gtgaactccc agagcatgcc tgatagaaac tcatttctac
3241 tgttctctaa ctgtggagtg aatgaaatt  ccaactgtat gttcaccctc tgaagtgggt
3301 acccagtctc ttaaatcttt tgtatttgct cacagtgttt gagcagtgct gagcacaaag
3361 cagacactca ataaatgcta gatttacaca ctcaaaaaaa aaaaa
```

SEQ ID NO:1

Figure 10b

MSSSSWLLLSLVAVTAAQSTIEEQAKTFLDKFNHEAEDLFYQSSLASWNYNTNITEENVQNMNNAGDKWSAFLKEQSTLAQMY
PLQEIQNLTVKLQLQALQQNGSSVLSEDKSKRLNTILNTMSTIYSTGKVCNPDNPQECLLLEPGLNEIMANSLDYNERLWAWE
SWRSEVGKQLRPLYEEYVVLKNEMARANHYEDYGDYWRGDYEVNGVDGYDYSRGQLIEDVEHTFEEIKPLYEHLHAYVRAKLM
NAYPSYISPIGCLPAHLLGDMWGRFWTNLYSLTVPFGQKPNIDVTDAMVDQAWDAQRIFKEAEKFFVSVGLPNMTQGFWENSM
LTDPGNVQKAVCHPTAWDLGKGDFRILMCTKVTMDDFLTAHHEMGHIQYDMAYAAQPFLLRNGANEGFHEAVGEIMSLSAATP
KHLKSIGLLSPDFQEDNETEINFLLKQALTIVGTLPFTYMLEKWRWMVFKGEIPKDQWMKKWWEMKREIVGVVEPVPHDETYC
DPASLFHVSNDYSFIRYYTRTLYQFQFQEALCQAAKHEGPLHKCDISNSTEAGQKLFNMLRLGKSEPWTLALENVVGAKNMNV
RPLLNYFEPLFTWLKDQNKNSFVGWSTDWSPYADQSIKVRISLKSALGDKAYEWNDNEMYLFRSSVAYAMRQYFLKVKNQMIL
FGEEDVRVANLKPRISFNFFVTAPKNVSDIIPRTEVEKAIRMSRSRINDAFRLNDNSLEFLGIQPTLGPPNQPPVSIWLIVFG
VVMGVIVVGIVILIFTGIRDRKKKNKARSGENPYASIDISKGENNPGFQNTDDVQTSF

SEQ ID NO:2

Figure 11

```
   1 catattggtc cagcagcttg tttactgttc tcttctgttt cttcttctgc ttttttttc
  61 ttctcttctc agtgcccaac ccaagttcaa aggctgatga gagagaaaaa ctcatgaaga
 121 gattttactc tagggaaagt tgctcagtgg atgggatctt ggcgcacggg gaaagatgtc
 181 cagctcctcc tggctccttc tcagccttgt tgctgttact actgctcagt ccctcaccga
 241 ggaaaatgcc aagacatttt taaacaactt taatcaggaa gctgaagacc tgtcttatca
 301 aagttcactt gcttcttgga attataatac taacattact gaagaaaatg cccaaaagat
 361 gagtgaggct gcagccaaat ggtctgcctt ttatgaagaa cagtctaaga ctgcccaaag
 421 tttctcacta caagaaatcc agactccgat catcaagcgt caactacagg cccttcagca
 481 aagtgggtct tcagcactct cagcagacaa gaacaaacag ttgaacacaa ttctgaacac
 541 catgagcacc atttacagta ctggaaaagt ttgcaaccca agaacccac aagaatgctt
 601 attacttgag ccaggattgg atgaaataat ggcgacaagc acagactaca actctaggct
 661 ctgggcatgg gagggctgga gggctgaggt tggcaagcag ctgaggccgt tgtatgaaga
 721 gtatgtggtc ctgaaaaacg agatggcaag agcaaacaat tataacgact atggggatta
 781 ttggagaggg gactatgaag cagagggagc agatggctac aactataacc gtaaccagtt
 841 gattgaagat gtagaacgta ccttcgcaga gatcaagcca ttgtatgagc atcttcatgc
 901 ctatgtgagg aggaagttga tggataccta cccttcctac atcagcccca ctggatgcct
 961 ccctgcccat ttgcttggtg atatgtgggg tagattttgg acaaatctgt acccttgac
1021 tgttcccttt gcacagaaac caaacataga tgttactgat gcaatgatga atcagggctg
1081 ggatgcagaa aggatatttc aagaggcaga gaaattcttt gtttctgttg gccttcctca
1141 tatgactcaa ggattctggg caaactctat gctgactgag ccagcagatg gccggaaagt
1201 tgtctgccac cccacagctt gggatctggg acacggagac ttcagaatca agatgtgtac
1261 aaaggtcaca atggacaact tcttgacagc ccatcacgag atgggacaca tccaatatga
1321 catggcatat gccaggcaac cttttcctgct aagaaacgga gccaatgaag ggttccatga
1381 agctgttgga gaaatcatgt cactttctgc agctaccccc aagcatctga aatccattgg
1441 tcttctgcca tccgattttc aagaagatag cgaaacagag ataaacttcc tactgaaaca
1501 ggcattgaca attgttggaa cactaccgtt tacttacatg ttagagaagt ggaggtggat
1561 ggtctttcgg ggtgaaattc ccaaagagca gtggatgaaa aagtggtggg agatgaagcg
1621 ggagatcgtt ggtgtggtgg agcctctgcc tcatgatgaa acatactgtg accctgcatc
1681 tctgttccat gtttctaatg attactcatt cattcgatat tacacaagga ccatttacca
1741 attccagttt caagaagctc tttgtcaagc agctaagtat aatggttctc tgcacaaatg
1801 tgacatctca aattccactg aagctgggca gaagttgctc aagatgctga gtcttggaaa
1861 ttcagagccc tggaccaaag ccttggaaaa tgtggtagga gcaaggaata tggatgtaaa
1921 accactgctc aattacttcc aaccgttgtt tgactggctg aaagagcaga acagaaattc
1981 ttttgtgggg tggaacactg aatgagccc atatgccgac caaagcatta agtgaggat
2041 aagcctaaaa tcagctcttg gagctaatgc atatgaatgg accaacaacg aaatgttcct
2101 gttccgatca tctgttgcat atgccatgag aaagtatttt tcaataatca aaaccagac
2161 agttcctttt ctagaggaag atgtacgagt gagtgatttg aaaccaagag tctccttcta
2221 cttctttgtc acctcacccc aaaatgtgtc tgatgtcatt cctagaagtg aagttgaaga
2281 tgccatcagg atgtctcggg gccgcatcaa tgatgtcttt ggcctgaatg ataacagcct
2341 ggagtttctg gggattcacc caacacttga gccaccttac cagcctcctg tcaccatatg
2401 gctgattatt tttggtgttg tgatggcact ggtagtggtt ggcatcatca tcctgattgt
2461 cactggcatc aaaggtcgaa agaagaaaaa tgaaacaaaa agagaagaga cccttatga
2521 ctcgatggac attggaaaag gagaaagcaa tgcaggattc caaaacagtg atgatgctca
2581 gacttccttt tagcaaagca cttgtcatct tcctgtatgt aaatgctaac ttcatagtac
2641 acaaaatatg agagtataca catgtcatta gctatcaaaa ctatgatctg ttcagtaaac
2701 gttgtccaaa gagcatcaaa aaaaaaaaaa aaaaaaaa
```

SEQ ID NO:3

Figure 12

| | | African Am | Asian | Caucasian | Reference | |
|---|---|---|---|---|---|---|
| rs879922 | C(C/G) | 60 | 100 | 70 | C | TTAACTTGAAGTCCAAAAACATATGTTCTTCACCTA[C/G]TAACCCCAGT CCTTGAATTTGCTGGAGCTCAGTTT SEQ ID NO. 5 |
| rs757066 | T(C/T) | 100 | 100 | 70 | T | GTATCTCACCATCAGAAAACACAAGCTTGTGTC[C/T]AGGATATTAGCTA ATAAAGTTTGTAAAcat SEQ ID NO.6 |
| rs714205 | C(C/G) | 70 | 50 | 80 | C | CCATGAGTTCTAGCGAGACTTCTTCAACCAGCACCTGCTCCC[C/G]TT TACCAGAGAGCATTCTCAGACCACAAGATCC SEQ ID NO. 7 |
| rs329442 | C(A/C) | 50 | 90 | 90 | A/C | Acaggtttgtcttaaaacttcatatcagagttatgtgaaaactgcacatc[C/A] CACTATTGGAAATATTCTGGTGTTATCTTTGTATTTAATTTCTCAGTGGG T SEQ ID NO.8 |
| rs233574 | C(C/T) | 80 | 100 | 60 | C | Attgtgccactgcctctgcctaggtgacagagagcaagactc[C/T] GTTCAAAAAAAAAAGGAATATACACC SEQ ID NO.9 |
| rs1978124 | C(C/T) | 90 | 100 | 50 | C | CTTTGAAACCTGTTTAACCAAGCTTTTTTCCATATCTCTATCTGAT GGAC[C/T]TCTCCACACTTCTACATCAGCAGCTTTATGACAC SEQ ID NO. 10 |
| rs1978124-2new | G(G/A) | 30 | 70 | 40 | C | CTTTGGAAACCTGTTTAACCAAGCTTTTTTCCATATCTCTATCTGAT GG[G/A]CCTCTCCACACTTCTACATCAGCAGCTTTATGACAC SEQ ID NO. 11 |
| rs1514282 | A(A/G) | 70 | 100 | 100 | A | AACACAGCAGTCACAAATGAATAAATGCCAACCATTTATACATTTCCAC ACTT[G/A]CAACTCAATTTCCAATGGAGCTGTTGATGAACCTAATCTA GGTTGCAAGGCATGAAA SEQ ID NO. 12 |
| rs1514282-2(new) | A(A/G) | 20 | 50 | 30 | A | TTCTTGCCAAATATGATAACTTTGCCCTTAAACACAGCAGTCACAAATG AATAAAT[G/A]CCAACCATTTATACATTTCCACACTTACAACTCAATTTT CCAATGGAGCTGTTGATG SEQ ID NO.13 |
| rs1514281 | A(A/G) | 70 | 100 | 100 | A | GAAATTCTTGCCAAATATGATAACTTTGCCCTTAAACACAGCAGTCACA AATGAATAAATACCA[G/A]ACCATTTATACATTTCCACACTTACAACTCA ATTTTCCAATGGAGCTGTTGATGAA SEQ ID NO. 14 |
| rs1514281-2(new) | A(A/G) | 20 | 50 | 50 | A | GAAATTCTTGCCAAATATGATAACTTTGCCCTTAAACACAGCAGTCACA AATGAATAAAT[G/A]CCAACCATTTATACATTTCCACACTTACAACTCAA TTTTCCAATGGAGCTGTTGATGAA SEQ ID NO. 15 |
| rs1514279 | A(A/G) | Failed | 100 | 70 | A | ATAGTCACTAAAATGTATTGCACCAGGTACTATGCT[G/A]TATCTTATAT GATGGTTCTTTATGAATATCTG SEQ ID NO. 16 |
| rs1514280 | C(C/T) | 80 | 100 | 80 | C | GTTTACAAAGTGTTATTTTCATTTGAA[C/T]GTCAAGTTTTTCTTTTACA CTTATAGATAAGTACATTTC SEQ ID NO.17 |
| rs233575 | C(C/T) | 100 | 100 | 50 | C | GTGCTACCTCCAAATGCCAATACCTTTATTTGGAAAATA[C/T] TACTATAGAGACTTGGTCATAGGACCTGATTCATT SEQ ID NO. 18 |

SEQUENCE LISTING

```
<160> NUMBER OF SEQ ID NOS: 24

<210> SEQ ID NO 1
<211> LENGTH: 3405
<212> TYPE: DNA
<213> ORGANISM: Homo sapiens

<400> SEQUENCE: 1
cgcccaaccc aagttcaaag gctgataaga gagaaaatct catgaggagg ttttagtcta      60
gggaaagtca ttcagtggat gtgatcttgg ctcacagggg acgatgtcaa gctcttcctg     120
gctccttctc agccttgttg ctgtaactgc tgctcagtcc accattgagg aacaggccaa     180 gacattttg gacaagttta accacgaagc cgaagacctg ttctatcaaa gttcacttgc     240
ttcttggaat tataacacca atattactga agagaatgtc caaaacatga ataatgctgg     300
ggacaaatgg tctgcctttt taaggaaca gtccacactt gcccaaatgt atccactaca     360
agaaattcag aatctcacag tcaagcttca gctgcaggct cttcagcaaa tgggtcttc     420 agtgctctca gaagacaaga gcaaacggtt gaacacaatt ctaaatacaa tgagcaccat     480
ctacagtact ggaaaagttt gtaacccaga taatccacaa gaatgcttat tacttgaacc     540
aggtttgaat gaaataatgg caaacagttt agactacaat gagaggctct gggcttggga     600
aagctggaga tctgaggtcg gcaagcagct gaggccatta tatgaagagt atgtggtctt     660
gaaaaatgag atggcaagag caaatcatta tgaggactat ggggattatt ggagaggaga     720
ctatgaagta aatgggtag atggctatga ctacagccgc ggccagttga ttgaagatgt     780
ggaacatacc tttgaagaga ttaaaccatt atatgaacat cttcatgcct atgtgagggc     840
aaagttgatg aatgcctatc cttcctatat cagtccaatt ggatgcctcc ctgctcattt     900
gcttggtgat atgtggggta gattttggac aaatctgtac tctttgacag ttcccttgg     960 acagaaacca acatagatg ttactgatgc aatggtggac caggcctggg atgcacagag    1020
aatattcaag gaggccgaga gttctttgt atctgttggt cttcctaata tgactcaagg    1080
attctgggaa aattccatgc taacggaccc aggaaatgtt cagaaagcag tctgccatcc    1140
cacagcttgg gacctgggga agggcgactt caggatcctt atgtgcacaa aggtgacaat    1200
ggacgacttc ctgacagctc atcatgagat ggggcatatc cagtatgata tggcatatgc    1260
```

```
tgcacaacct tttctgctaa gaaatggagc taatgaagga ttccatgaag ctgttgggga    1320
aatcatgtca ctttctgcag ccacacctaa gcatttaaaa tccattggtc ttctgtcacc    1380
cgattttcaa gaagacaatg aaacagaaat aaacttcctg ctcaaacaag cactcacgat    1440
tgttgggact ctgccattta cttacatgtt agagaagtgg aggtggatgg tctttaaagg    1500
ggaaattccc aaagaccagt ggatgaaaaa gtggtgggag atgaagcgag agatagttgg    1560
ggtggtggaa cctgtgcccc atgatgaaac atactgtgac cccgcatctc tgttccatgt    1620
ttctaatgat tactcattca ttcgatatta cacaaggacc ctttaccaat tccagtttca    1680
agaagcactt tgtcaagcag ctaaacatga aggccctctg cacaaatgtg acatctcaaa    1740
ctctacagaa gctggacaga aactgttcaa tatgctgagg cttggaaaat cagaaccctg    1800
gaccctagca ttggaaaatg ttgtaggagc aaagaacatg aatgtaaggc cactgctcaa    1860
ctactttgag cccttattta cctggctgaa agaccagaac aagaattctt ttgtgggatg    1920
gagtaccgac tggagtccat atgcagacca agcatcaaa gtgaggataa gcctaaaatc    1980
agctcttgga gataaagcat atgaatggaa cgacaatgaa atgtacctgt ccgatcatc    2040 tgttgcatat gctatgaggc agtacttttt aaaagtaaaa aatcagatga ttctttttgg    2100
ggaggaggat gtgcgagtgg ctaatttgaa accaagaatc tcctttaatt tctttgtcac    2160
tgcacctaaa aatgtgtctg atatcattcc tagaactgaa gttgaaaagg ccatcaggat    2220
gtcccggagc cgtatcaatg atgctttccg tctgaatgac aacagcctag agtttctggg    2280
gatacagcca acacttggac ctcctaacca gcccctgtt tccatatggc tgattgtttt    2340
tggagttgtg atgggagtga tagtggttgg cattgtcatc ctgatcttca ctgggatcag    2400
agatcggaag aagaaaaata agcaagaag tggagaaaat ccttatgcct ccatcgatat    2460
tagcaaagga gaaataatc caggattcca aaacactgat gatgttcaga cctccttta    2520 gaaaaatcta tgttttcct cttgaggtga ttttgttgta tgtaaatgtt aatttcatgg    2580
tatagaaaat ataagatgat aaagatatca ttaaatgtca aaactatgac tctgttcaga    2640
aaaaaaattg tccaaagaca acatggccaa ggagagagca tcttcattga cattgctttc    2700
agtatttatt tctgtctctg gatttgactt ctgttctgtt tcttaataag gattttgtat    2760
tagagtatat tagggaaagt gtgtatttgg tctcacaggc tgttcaggga taatctaaat    2820
gtaaatgtct gttgaatttc tgaagttgaa aacaaggata tatcattgga gcaagtgttg    2880
gatcttgtat ggaatatgga tggatcactt gtaaggacag tgcctgggaa ctggtgtagc    2940
tgcaaggatt gagaatggca tgcattagct cactttcatt taatccattg tcaaggatga    3000
catgctttct tcacagtaac tcagttcaag tactatggtg atttgcctac agtgatgttt    3060
ggaatcgatc atgctttctt caaggtgaca ggtctaaaga gagaagaatc cagggaacag    3120
gtagaggaca ttgcttttc acttccaagg tgcttgatca acatctccct gacaacacaa    3180
aactagagcc aggggcctcc gtgaactccc agagcatgcc tgatagaaac tcatttctac    3240
tgttctctaa ctgtggagtg aatggaaatt ccaactgtat gttcaccctc tgaagtgggt    3300
acccagtctc ttaaatcttt tgtatttgct cacagtgttt gagcagtgct gagcacaaag    3360
cagacactca ataaatgcta gatttacaca ctcaaaaaaa aaaaa                    3405
```

<210> SEQ ID NO 2
<211> LENGTH: 805
<212> TYPE: PRT
<213> ORGANISM: Homo sapiens

<400> SEQUENCE: 2

```
Met Ser Ser Ser Ser Trp Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415
```

```
His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
            450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
            610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Asp Val Arg Val
            660                 665                 670

Ala Asn Leu Lys Pro Arg Ile Ser Phe Asn Phe Val Thr Ala Pro
            675                 680                 685

Lys Asn Val Ser Asp Ile Ile Pro Arg Thr Glu Val Glu Lys Ala Ile
            690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
            755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 3
<211> LENGTH: 2739
<212> TYPE: DNA
```

<213> ORGANISM: Mus musculus

<400> SEQUENCE: 3

```
catattggtc cagcagcttg tttactgttc tcttctgttt cttcttctgc ttttttttc      60
ttctcttctc agtgcccaac ccaagttcaa aggctgatga gagagaaaaa ctcatgaaga     120
gattttactc tagggaaagt tgctcagtgg atgggatctt ggcgcacggg gaaagatgtc     180
cagctcctcc tggctccttc tcagccttgt tgctgttact actgctcagt ccctcaccga     240
ggaaaatgcc aagacatttt taaacaactt taatcaggaa gctgaagacc tgtcttatca     300
aagttcactt gcttcttgga attataatac taacattact gaagaaaatg cccaaaagat     360
gagtgaggct gcagccaaat ggtctgcctt ttatgaagaa cagtctaaga ctgcccaaag     420
tttctcacta caagaaatcc agactccgat catcaagcgt caactacagg cccttcagca     480
aagtgggtct tcagcactct cagcagacaa gaacaaacag ttgaacacaa ttctgaacac     540
catgagcacc atttacagta ctggaaaagt ttgcaaccca agaacccac aagaatgctt      600
attacttgag ccaggattgg atgaaataat ggcgacaagc acagactaca actctaggct     660
ctgggcatgg gagggctgga gggctgaggt tggcaagcag ctgaggccgt tgtatgaaga     720
gtatgtggtc ctgaaaaacg agatggcaag agcaaacaat tataacgact atggggatta     780
ttggagaggg gactatgaag cagagggagc agatggctac aactataacc gtaaccagtt     840
gattgaagat gtagaacgta ccttcgcaga gatcaagcca ttgtatgagc atcttcatgc     900
ctatgtgagg aggaagttga tggataccta cccttcctac atcagcccca ctggatgcct     960
ccctgcccat ttgcttggtg atatgtgggg tagattttgg acaaatctgt acccttttgac    1020
tgttcccttt gcacagaaac caaacataga tgttactgat gcaatgatga atcagggctg    1080
ggatgcagaa aggatatttc aagaggcaga gaattctttt gtttctgttg gccttcctca    1140
tatgactcaa ggattctggg caaactctat gctgactgag ccagcagatg gccggaaagt    1200
tgtctgccac cccacagctt gggatctggg acacggagac ttcagaatca agatgtgtac    1260
aaaggtcaca atggacaact tcttgacagc ccatcacgag atgggacaca tccaatatga    1320
catggcatat gccaggcaac ctttcctgct aagaaacgga gccaatgaag ggttccatga    1380
agctgttgga gaaatcatgt cactttctgc agctaccccc aagcatctga atccattgg     1440
tcttctgcca tccgattttc aagaagatag cgaaacagag ataaacttcc tactgaaaca    1500
ggcattgaca attgttggaa cactaccgtt tacttacatg ttagagaagt ggaggtggat    1560
ggtctttcgg ggtgaaattc ccaaagagca gtggatgaaa aagtggtggg agatgaagcg    1620
ggagatcgtt ggtgtggtgg agcctctgcc tcatgatgaa acatactgtg accctgcatc    1680
tctgttccat gtttctaatg attactcatt cattcgatat tacacaagga ccatttacca    1740
attccagttt caagaagctc tttgtcaagc agctaagtat aatggttctc tgcacaaatg    1800
tgacatctca aattccactg aagctgggca gaagttgctc aagatgctga gtcttggaaa    1860
ttcagagccc tggaccaaag ccttggaaaa tgtggtagga gcaaggaata tggatgtaaa    1920
accactgcta aattacttcc aaccgttgtt tgactggctg aaagagcaga acagaaattc    1980
ttttgtgggg tggaacactg aatggagccc atatgccgac caaagcatta agtgaggat     2040
aagcctaaaa tcagctcttg gagctaatgc atatgaatgg accaacaacg aaatgttcct    2100
gttccgatca tctgttgcat atgccatgag aaagtatttt tcaataatca aaaccagac     2160
agttcctttt ctagaggaag atgtacgagt gagtgatttg aaaccaagag tctccttcta    2220
cttctttgtc acctcacccc aaaatgtgtc tgatgtcatt cctagaagtg aagttgaaga    2280
```

-continued

```
tgccatcagg atgtctcggg gccgcatcaa tgatgtcttt ggcctgaatg ataacagcct    2340
ggagtttctg gggattcacc caacacttga gccaccttac cagcctcctg tcaccatatg    2400
gctgattatt tttggtgttg tgatggcact ggtagtggtt ggcatcatca tcctgattgt    2460
cactggcatc aaaggtcgaa agaagaaaaa tgaaacaaaa agagaagaga acccttatga    2520
ctcgatggac attggaaaag gagaaagcaa tgcaggattc caaaacagtg atgatgctca    2580
gacttccttt tagcaaagca cttgtcatct tcctgtatgt aaatgctaac ttcatagtac    2640
acaaaatatg agagtataca catgtcatta gctatcaaaa ctatgatctg ttcagtaaac    2700
gttgtccaaa gagcatcaaa aaaaaaaaaa aaaaaaaa                             2739
```

<210> SEQ ID NO 4
<211> LENGTH: 805
<212> TYPE: PRT
<213> ORGANISM: Mus musculus

<400> SEQUENCE: 4

```
Met Ser Ser Ser Ser Trp Leu Leu Leu Ser Leu Val Ala Val Thr Thr
1               5                   10                  15

Ala Gln Ser Leu Thr Glu Glu Asn Ala Lys Thr Phe Leu Asn Asn Phe
            20                  25                  30

Asn Gln Glu Ala Glu Asp Leu Ser Tyr Gln Ser Ser Leu Ala Ser Trp
        35                  40                  45

Asn Tyr Asn Thr Asn Ile Thr Glu Glu Asn Ala Gln Lys Met Ser Glu
    50                  55                  60

Ala Ala Ala Lys Trp Ser Ala Phe Tyr Glu Glu Gln Ser Lys Thr Ala
65                  70                  75                  80

Gln Ser Phe Ser Leu Gln Glu Ile Gln Thr Pro Ile Ile Lys Arg Gln
                85                  90                  95

Leu Gln Ala Leu Gln Gln Ser Gly Ser Ser Ala Leu Ser Ala Asp Lys
            100                 105                 110

Asn Lys Gln Leu Asn Thr Ile Leu Asn Thr Met Ser Thr Ile Tyr Ser
        115                 120                 125

Thr Gly Lys Val Cys Asn Pro Lys Asn Pro Gln Glu Cys Leu Leu Leu
    130                 135                 140

Glu Pro Gly Leu Asp Glu Ile Met Ala Thr Ser Thr Asp Tyr Asn Ser
145                 150                 155                 160

Arg Leu Trp Ala Trp Glu Gly Trp Arg Ala Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn Asn Tyr Asn Asp Tyr Gly Asp Tyr Trp Arg Gly Asp Tyr Glu
        195                 200                 205

Ala Glu Gly Ala Asp Gly Tyr Asn Tyr Asn Arg Asn Gln Leu Ile Glu
    210                 215                 220

Asp Val Glu Arg Thr Phe Ala Glu Ile Lys Pro Leu Tyr Glu His Leu
225                 230                 235                 240

His Ala Tyr Val Arg Arg Lys Leu Met Asp Thr Tyr Pro Ser Tyr Ile
                245                 250                 255

Ser Pro Thr Gly Cys Leu Pro Ala His Leu Leu Gly Asp Met Trp Gly
            260                 265                 270

Arg Phe Trp Thr Asn Leu Tyr Pro Leu Thr Val Pro Phe Ala Gln Lys
        275                 280                 285
```

```
Pro Asn Ile Asp Val Thr Asp Ala Met Met Asn Gln Gly Trp Asp Ala
290                 295                 300

Glu Arg Ile Phe Gln Glu Ala Glu Lys Phe Phe Val Ser Val Gly Leu
305                 310                 315                 320

Pro His Met Thr Gln Gly Phe Trp Ala Asn Ser Met Leu Thr Glu Pro
                325                 330                 335

Ala Asp Gly Arg Lys Val Val Cys His Pro Thr Ala Trp Asp Leu Gly
                340                 345                 350

His Gly Asp Phe Arg Ile Lys Met Cys Thr Lys Val Thr Met Asp Asn
                355                 360                 365

Phe Leu Thr Ala His His Glu Met Gly His Ile Gln Tyr Asp Met Ala
370                 375                 380

Tyr Ala Arg Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Pro Ser Asp Phe Gln Glu Asp Ser
                420                 425                 430

Glu Thr Glu Ile Asn Phe Leu Leu Lys Gln Ala Leu Thr Ile Val Gly
                435                 440                 445

Thr Leu Pro Phe Thr Tyr Met Leu Glu Lys Trp Arg Trp Met Val Phe
450                 455                 460

Arg Gly Glu Ile Pro Lys Glu Gln Trp Met Lys Lys Trp Trp Glu Met
465                 470                 475                 480

Lys Arg Glu Ile Val Gly Val Val Glu Pro Leu Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Ile Tyr Gln Phe Gln Phe Gln Glu Ala
                515                 520                 525

Leu Cys Gln Ala Ala Lys Tyr Asn Gly Ser Leu His Lys Cys Asp Ile
530                 535                 540

Ser Asn Ser Thr Glu Ala Gly Gln Lys Leu Lys Met Leu Ser Leu
545                 550                 555                 560

Gly Asn Ser Glu Pro Trp Thr Lys Ala Leu Glu Asn Val Val Gly Ala
                565                 570                 575

Arg Asn Met Asp Val Lys Pro Leu Leu Asn Tyr Phe Gln Pro Leu Phe
                580                 585                 590

Asp Trp Leu Lys Glu Gln Asn Arg Asn Ser Phe Val Gly Trp Asn Thr
                595                 600                 605

Glu Trp Ser Pro Tyr Ala Asp Gln Ser Ile Lys Val Arg Ile Ser Leu
                610                 615                 620

Lys Ser Ala Leu Gly Ala Asn Ala Tyr Glu Trp Thr Asn Asn Glu Met
625                 630                 635                 640

Phe Leu Phe Arg Ser Ser Val Ala Tyr Ala Met Arg Lys Tyr Phe Ser
                645                 650                 655

Ile Ile Lys Asn Gln Thr Val Pro Phe Leu Glu Glu Asp Val Arg Val
                660                 665                 670

Ser Asp Leu Lys Pro Arg Val Ser Phe Tyr Phe Phe Val Thr Ser Pro
                675                 680                 685

Gln Asn Val Ser Asp Val Ile Pro Arg Ser Glu Val Glu Asp Ala Ile
                690                 695                 700

Arg Met Ser Arg Gly Arg Ile Asn Asp Val Phe Gly Leu Asn Asp Asn
```

```
                705                 710                 715                 720
Ser Leu Glu Phe Leu Gly Ile His Pro Thr Leu Glu Pro Pro Tyr Gln
                725                 730                 735

Pro Pro Val Thr Ile Trp Leu Ile Ile Phe Gly Val Val Met Ala Leu
                740                 745                 750

Val Val Val Gly Ile Ile Ile Leu Ile Val Thr Gly Ile Lys Gly Arg
            755                 760                 765

Lys Lys Lys Asn Glu Thr Lys Arg Glu Glu Asn Pro Tyr Asp Ser Met
        770                 775                 780

Asp Ile Gly Lys Gly Glu Ser Asn Ala Gly Phe Gln Asn Ser Asp Asp
785                 790                 795                 800

Ala Gln Thr Ser Phe
            805

<210> SEQ ID NO 5
<211> LENGTH: 73
<212> TYPE: DNA
<213> ORGANISM: Homo sapiens

<400> SEQUENCE: 5
ttaacttgaa gtccaaaaac atatgttctt cacctacgta accccagtcc ttgaatttgc    60
tggagctcag ttt                                                        73

<210> SEQ ID NO 6
<211> LENGTH: 64
<212> TYPE: DNA
<213> ORGANISM: Homo sapiens

<400> SEQUENCE: 6
gtatctcacc atcagaaaac acaagcttgt gtctaggata ttagctaata aagtttgtaa    60
acat                                                                  64

<210> SEQ ID NO 7
<211> LENGTH: 77
<212> TYPE: DNA
<213> ORGANISM: Homo sapiens
<220> FEATURE:
<221> NAME/KEY: misc_feature
<222> LOCATION: (44)..(44)
<223> OTHER INFORMATION: n= c or g

<400> SEQUENCE: 7
ccatgagttc tagccagact ttcttcaacc agcacctgct cccntttacc agagagcatt    60
ctcagaccac aagatcc                                                    77

<210> SEQ ID NO 8
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: n= c or a

<400> SEQUENCE: 8
acaggtttgt cttaaaactt catatcagag ttatgtgaaa actgcacatc ncactattgg    60
aatattctgg tgttatcttt gtatttaatt tctcagtggg t                        101

<210> SEQ ID NO 9
<211> LENGTH: 74
```

<212> TYPE: DNA
<213> ORGANISM: Homo sapiens
<220> FEATURE:
<221> NAME/KEY: misc_feature
<222> LOCATION: (43)..(43)
<223> OTHER INFORMATION: n= c or t

<400> SEQUENCE: 9
attgtgccac tgccctctag cctaggtgac agagcaagac tcngtttcaa aaaaaaaaaa    60
aaggaatata cacc                                                      74

<210> SEQ ID NO 10
<211> LENGTH: 89
<212> TYPE: DNA
<213> ORGANISM: Homo sapiens
<220> FEATURE:
<221> NAME/KEY: misc_feature
<222> LOCATION: (55)..(55)
<223> OTHER INFORMATION: n= c or t

<400> SEQUENCE: 10
ctttggaaac ctgttttaac caagcttttt tttccatatc tctatctgat ggacntctcc    60
acacttctac atcagcagct ttatgacac                                      89

<210> SEQ ID NO 11
<211> LENGTH: 89
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n= g or a

<400> SEQUENCE: 11
ctttggaaac ctgttttaac caagcttttt tttccatatc tctatctgat ggncctctcc    60
acacttctac atcagcagct ttatgacac                                      89

<210> SEQ ID NO 12
<211> LENGTH: 112
<212> TYPE: DNA
<213> ORGANISM: Homo sapiens
<220> FEATURE:
<221> NAME/KEY: misc_feature
<222> LOCATION: (54)..(54)
<223> OTHER INFORMATION: n= g or a

<400> SEQUENCE: 12
aacacagcag tcacaaatga ataaatgcca accatttata catttccaca cttncaactc    60
aattttccaa tggagctgtt gatgaaccta atctaggttg caaggcatga aa           112

<210> SEQ ID NO 13
<211> LENGTH: 114
<212> TYPE: DNA
<213> ORGANISM: Homo sapiens
<220> FEATURE:
<221> NAME/KEY: misc_feature
<222> LOCATION: (57)..(57)
<223> OTHER INFORMATION: n=g or a

<400> SEQUENCE: 13
ttcttgccaa atatgataac tttgccctta aacacagcag tcacaaatga ataaatncca    60
accatttata catttccaca cttacaactc aattttccaa tggagctgtt gatg         114

<210> SEQ ID NO 14

```
<211> LENGTH: 121
<212> TYPE: DNA
<213> ORGANISM: Homo sapiens
<220> FEATURE:
<221> NAME/KEY: misc_feature
<222> LOCATION: (65)..(65)
<223> OTHER INFORMATION: n= g or a

<400> SEQUENCE: 14
gaaattcttg ccaaatatga taactttgcc cttaaacaca gcagtcacaa atgaataaat      60
accanaccat ttatacattt ccacacttac aactcaattt tccaatggag ctgttgatga     120
a                                                                     121

<210> SEQ ID NO 15
<211> LENGTH: 120
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n= g or a

<400> SEQUENCE: 15
gaaattcttg ccaaatatga taactttgcc cttaaacaca gcagtcacaa atgaataaat      60
nccaaccatt tatacatttc cacacttaca actcaatttt ccaatggagc tgttgatgaa    120

<210> SEQ ID NO 16
<211> LENGTH: 69
<212> TYPE: DNA
<213> ORGANISM: Homo sapiens
<220> FEATURE:
<221> NAME/KEY: misc_feature
<222> LOCATION: (37)..(37)
<223> OTHER INFORMATION: n= g or a

<400> SEQUENCE: 16
atagtcacta aaatgtattg caccaggtac tatgctntat cttatatgat ggttctttat      60
gaatatctg                                                              69

<210> SEQ ID NO 17
<211> LENGTH: 68
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n= c or t

<400> SEQUENCE: 17
gtttacaaag tgttattttt catttgaang tcaagttttt cttttacact tatagataag      60
tacatttc                                                               68

<210> SEQ ID NO 18
<211> LENGTH: 76
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n= c or t

<400> SEQUENCE: 18
gtgctacctc caaatgccaa tacctttat ttggaaaata ntactataga gacttggtca      60
taggacctga ttcatt                                                     76
```

```
<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
tcaatttact gctgaggggg                                                       20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
gagggataac ccagtgcaaa                                                       20

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide

<400> SEQUENCE: 21

Asp Tyr Glu Ala Glu Gly Ala Asp Gly Tyr Asn Tyr Asn Arg Asn Gln
1               5                   10                  15

Leu Ile Glu Asp
            20

<210> SEQ ID NO 22
<211> LENGTH: 732
<212> TYPE: PRT
<213> ORGANISM: Mus musculus

<400> SEQUENCE: 22

Met Gly Gln Gly Trp Ala Thr Pro Gly Leu Pro Ser Phe Leu Phe Leu
1               5                   10                  15

Leu Leu Cys Cys Gly His His Leu Leu Val Leu Ser Gln Val Ala Thr
            20                  25                  30

Asp His Val Thr Ala Asn Gln Gly Ile Thr Asn Gln Ala Thr Thr Arg
        35                  40                  45

Ser Gln Thr Thr Thr His Gln Ala Thr Ile Asp Gln Thr Thr Gln Ile
    50                  55                  60

Pro Asn Leu Glu Thr Asp Glu Ala Lys Ala Asp Arg Phe Val Glu Glu
65                  70                  75                  80

Tyr Asp Arg Thr Ala Gln Val Leu Leu Asn Glu Tyr Ala Glu Ala Asn
                85                  90                  95

Trp Gln Tyr Asn Thr Asn Ile Thr Ile Glu Gly Ser Lys Ile Leu Leu
            100                 105                 110

Glu Lys Ser Thr Glu Val Ser Asn His Thr Leu Lys Tyr Gly Thr Arg
        115                 120                 125

Ala Lys Thr Phe Asp Val Ser Asn Phe Gln Asn Ser Ser Ile Lys Arg
    130                 135                 140

Ile Ile Lys Lys Leu Gln Asn Leu Asp Arg Ala Val Leu Pro Pro Lys
145                 150                 155                 160
```

-continued

```
Glu Leu Glu Glu Tyr Asn Gln Ile Leu Leu Asp Met Glu Thr Thr Tyr
                165                 170                 175
Ser Leu Ser Asn Ile Cys Tyr Thr Asn Gly Thr Cys Met Pro Leu Glu
            180                 185                 190
Pro Asp Leu Thr Asn Met Met Ala Thr Ser Arg Lys Tyr Glu Glu Leu
        195                 200                 205
Leu Trp Ala Trp Lys Ser Trp Arg Asp Lys Val Gly Arg Ala Ile Leu
210                 215                 220
Pro Phe Phe Pro Lys Tyr Val Glu Phe Ser Asn Lys Ile Ala Lys Leu
225                 230                 235                 240
Asn Gly Tyr Thr Asp Ala Gly Asp Ser Trp Arg Ser Leu Tyr Glu Ser
                245                 250                 255
Asp Asn Leu Glu Gln Asp Leu Glu Lys Leu Tyr Gln Glu Leu Gln Pro
            260                 265                 270
Leu Tyr Leu Asn Leu His Ala Tyr Val Arg Arg Ser Leu His Arg His
        275                 280                 285
Tyr Gly Ser Glu Tyr Ile Asn Leu Asp Gly Pro Ile Pro Ala His Leu
290                 295                 300
Leu Gly Asn Met Trp Ala Gln Thr Trp Ser Asn Ile Tyr Asp Leu Val
305                 310                 315                 320
Ala Pro Phe Pro Ser Ala Pro Asn Ile Asp Ala Thr Glu Ala Met Ile
                325                 330                 335
Lys Gln Gly Trp Thr Pro Arg Arg Ile Phe Lys Glu Ala Asp Asn Phe
            340                 345                 350
Phe Thr Ser Leu Gly Leu Leu Pro Val Pro Pro Glu Phe Trp Asn Lys
        355                 360                 365
Ser Met Leu Glu Lys Pro Thr Asp Gly Arg Glu Val Val Cys His Pro
370                 375                 380
Ser Ala Trp Asp Phe Tyr Asn Gly Lys Asp Phe Arg Ile Lys Gln Cys
385                 390                 395                 400
Thr Ser Val Asn Met Glu Asp Leu Val Ile Ala His His Glu Met Gly
                405                 410                 415
His Ile Gln Tyr Phe Met Gln Tyr Lys Asp Leu Pro Val Thr Phe Arg
            420                 425                 430
Glu Gly Ala Asn Pro Gly Phe His Glu Ala Ile Gly Asp Ile Met Ala
        435                 440                 445
Leu Ser Val Ser Thr Pro Lys His Leu Tyr Ser Leu Asn Leu Leu Ser
450                 455                 460
Thr Glu Gly Ser Gly Tyr Glu Tyr Asp Ile Asn Phe Leu Met Lys Met
465                 470                 475                 480
Ala Leu Asp Lys Ile Ala Phe Ile Pro Phe Ser Tyr Leu Ile Asp Gln
                485                 490                 495
Trp Arg Trp Arg Val Phe Asp Gly Ser Ile Thr Lys Glu Asn Tyr Asn
            500                 505                 510
Gln Glu Trp Trp Ser Leu Arg Leu Lys Tyr Gln Gly Leu Cys Pro Pro
        515                 520                 525
Val Pro Arg Ser Gln Gly Asp Phe Asp Pro Gly Ser Lys Phe His Val
530                 535                 540
Pro Ala Asn Val Pro Tyr Val Arg Tyr Phe Val Ser Phe Ile Ile Gln
545                 550                 555                 560
Phe Gln Phe His Glu Ala Leu Cys Arg Ala Ala Gly His Thr Gly Pro
                565                 570                 575
Leu His Lys Cys Asp Ile Tyr Gln Ser Lys Glu Ala Gly Lys Leu Leu
```

-continued

```
                580                 585                 590
Ala Asp Ala Met Lys Leu Gly Tyr Ser Lys Pro Trp Pro Glu Ala Met
            595                 600                 605

Lys Leu Ile Thr Gly Gln Pro Asn Met Ser Ala Ser Ala Met Met Asn
        610                 615                 620

Tyr Phe Lys Pro Leu Thr Glu Trp Leu Val Thr Glu Asn Arg Arg His
625                 630                 635                 640

Gly Glu Thr Leu Gly Trp Pro Glu Tyr Asn Trp Ala Pro Asn Thr Ala
            645                 650                 655

Arg Ala Glu Gly Ser Thr Ala Glu Ser Asn Arg Val Asn Phe Leu Gly
        660                 665                 670

Leu Tyr Leu Glu Pro Gln Gln Ala Arg Val Gly Gln Trp Val Leu Leu
    675                 680                 685

Phe Leu Gly Val Ala Leu Leu Val Ala Thr Val Gly Leu Ala His Arg
690                 695                 700

Leu Tyr Asn Ile Arg Asn His His Ser Leu Arg Arg Pro His Arg Gly
705                 710                 715                 720

Pro Gln Phe Gly Ser Glu Val Glu Leu Arg His Ser
            725                 730

<210> SEQ ID NO 23
<211> LENGTH: 732
<212> TYPE: PRT
<213> ORGANISM: Homo sapiens

<400> SEQUENCE: 23

Met Gly Gln Gly Trp Ala Thr Ala Gly Leu Pro Ser Leu Leu Phe Leu
1               5                   10                  15

Leu Leu Cys Tyr Gly His Pro Leu Leu Val Pro Ser Gln Glu Ala Ser
            20                  25                  30

Gln Gln Val Thr Val Thr His Gly Thr Ser Ser Gln Ala Thr Thr Ser
        35                  40                  45

Ser Gln Thr Thr Thr His Gln Ala Thr Ala His Gln Thr Ser Ala Gln
    50                  55                  60

Ser Pro Asn Leu Val Thr Asp Glu Ala Glu Ala Ser Lys Phe Val Glu
65                  70                  75                  80

Glu Tyr Asp Arg Thr Ser Gln Val Val Trp Asn Glu Tyr Ala Glu Ala
            85                  90                  95

Asn Trp Asn Tyr Asn Thr Asn Ile Thr Thr Glu Thr Ser Lys Ile Leu
        100                 105                 110

Leu Gln Lys Asn Met Gln Ile Ala Asn His Thr Leu Lys Tyr Gly Thr
    115                 120                 125

Gln Ala Arg Lys Phe Asp Val Asn Gln Leu Gln Asn Thr Thr Ile Lys
130                 135                 140

Arg Ile Ile Lys Lys Val Gln Asp Leu Glu Arg Ala Ala Leu Pro Ala
145                 150                 155                 160

Gln Glu Leu Glu Glu Tyr Asn Lys Ile Leu Leu Asp Met Glu Thr Thr
            165                 170                 175

Tyr Ser Val Ala Thr Val Cys His Pro Asn Gly Ser Cys Leu Gln Leu
        180                 185                 190

Glu Pro Asp Leu Thr Asn Val Met Ala Thr Ser Arg Lys Tyr Glu Asp
    195                 200                 205

Leu Leu Trp Ala Trp Glu Gly Trp Arg Asp Lys Ala Gly Arg Ala Ile
    210                 215                 220
```

```
Leu Gln Phe Tyr Pro Lys Tyr Val Glu Leu Ile Asn Gln Ala Ala Arg
225                 230                 235                 240

Leu Asn Gly Tyr Val Asp Ala Gly Asp Ser Trp Arg Ser Met Tyr Glu
            245                 250                 255

Thr Pro Ser Leu Glu Gln Asp Leu Glu Arg Leu Phe Gln Glu Leu Gln
            260                 265                 270

Pro Leu Tyr Leu Asn Leu His Ala Tyr Val Arg Arg Ala Leu His Arg
            275                 280                 285

His Tyr Gly Ala Gln His Ile Asn Leu Glu Gly Pro Ile Pro Ala His
            290                 295                 300

Leu Leu Gly Asn Met Trp Ala Gln Thr Trp Ser Asn Ile Tyr Asp Leu
305                 310                 315                 320

Val Val Pro Phe Pro Ser Ala Pro Ser Met Asp Thr Thr Glu Ala Met
            325                 330                 335

Leu Lys Gln Gly Trp Thr Pro Arg Arg Met Phe Lys Glu Ala Asp Asp
            340                 345                 350

Phe Phe Thr Ser Leu Gly Leu Leu Pro Val Pro Pro Glu Phe Trp Asn
            355                 360                 365

Lys Ser Met Leu Glu Lys Pro Thr Asp Gly Arg Glu Val Val Cys His
370                 375                 380

Ala Ser Ala Trp Asp Phe Tyr Asn Gly Lys Asp Phe Arg Ile Lys Gln
385                 390                 395                 400

Cys Thr Thr Val Asn Leu Glu Asp Leu Val Val Ala His His Glu Met
            405                 410                 415

Gly His Ile Gln Tyr Phe Met Gln Tyr Lys Asp Leu Pro Val Ala Leu
            420                 425                 430

Arg Glu Gly Ala Asn Pro Gly Phe His Glu Ala Ile Gly Asp Val Leu
            435                 440                 445

Ala Leu Ser Val Ser Thr Pro Lys His Leu His Ser Leu Asn Leu Leu
450                 455                 460

Ser Ser Glu Gly Gly Ser Asp Glu His Asp Ile Asn Phe Leu Met Lys
465                 470                 475                 480

Met Ala Leu Asp Lys Ile Ala Phe Ile Pro Phe Ser Tyr Leu Val Asp
            485                 490                 495

Gln Trp Arg Trp Arg Val Phe Asp Gly Ser Ile Thr Lys Glu Asn Tyr
            500                 505                 510

Asn Gln Glu Trp Trp Ser Leu Arg Leu Lys Tyr Gln Gly Leu Cys Pro
            515                 520                 525

Pro Val Pro Arg Thr Gln Gly Asp Phe Asp Pro Gly Ala Lys Phe His
            530                 535                 540

Ile Pro Ser Ser Val Pro Tyr Ile Arg Tyr Phe Val Ser Phe Ile Ile
545                 550                 555                 560

Gln Phe Gln Phe His Glu Ala Leu Cys Gln Ala Ala Gly His Thr Gly
            565                 570                 575

Pro Leu His Lys Cys Asp Ile Tyr Gln Ser Lys Glu Ala Gly Gln Arg
            580                 585                 590

Leu Ala Thr Ala Met Lys Leu Gly Phe Ser Arg Pro Trp Pro Glu Ala
            595                 600                 605

Met Gln Leu Ile Thr Gly Gln Pro Asn Met Ser Ala Ser Ala Met Leu
            610                 615                 620

Ser Tyr Phe Lys Pro Leu Leu Asp Trp Leu Arg Thr Glu Asn Glu Leu
625                 630                 635                 640

His Gly Glu Lys Leu Gly Trp Pro Gln Tyr Asn Trp Thr Pro Asn Ser
```

```
                         645                 650                 655
Ala Arg Ser Glu Gly Pro Leu Pro Asp Ser Gly Arg Val Ser Phe Leu
            660                 665                 670

Gly Leu Asp Leu Asp Ala Gln Gln Ala Arg Val Gly Gln Trp Leu Leu
        675                 680                 685

Leu Phe Leu Gly Ile Ala Leu Leu Val Ala Thr Leu Gly Leu Ser Gln
    690                 695                 700

Arg Leu Phe Ser Ile Arg His Arg Ser Leu His Arg Ser His Gly
705                 710                 715                 720

Pro Gln Phe Gly Ser Glu Val Glu Leu Arg His Ser
                725                 730

<210> SEQ ID NO 24
<211> LENGTH: 805
<212> TYPE: PRT
<213> ORGANISM: Rattus rattus

<400> SEQUENCE: 24

Met Ser Ser Ser Cys Trp Leu Leu Ser Leu Val Ala Val Ala Thr
1               5                   10                  15

Ala Gln Ser Leu Ile Glu Glu Lys Ala Glu Ser Phe Leu Asn Lys Phe
            20                  25                  30

Asn Gln Glu Ala Glu Asp Leu Ser Tyr Gln Ser Ser Leu Ala Ser Trp
        35                  40                  45

Asn Tyr Asn Thr Asn Ile Thr Glu Glu Asn Ala Gln Lys Met Asn Glu
    50                  55                  60

Ala Ala Ala Lys Trp Ser Ala Phe Tyr Glu Glu Gln Ser Lys Ile Ala
65                  70                  75                  80

Gln Asn Phe Ser Leu Gln Glu Ile Gln Asn Ala Thr Ile Lys Arg Gln
                85                  90                  95

Leu Lys Ala Leu Gln Gln Ser Gly Ser Ser Ala Leu Ser Pro Asp Lys
            100                 105                 110

Asn Lys Gln Leu Asn Thr Ile Leu Asn Thr Met Ser Thr Ile Tyr Ser
        115                 120                 125

Thr Gly Lys Val Cys Asn Ser Met Asn Pro Gln Glu Cys Phe Leu Leu
    130                 135                 140

Glu Pro Gly Leu Asp Glu Ile Met Ala Thr Ser Thr Asp Tyr Asn Arg
145                 150                 155                 160

Arg Leu Trp Ala Trp Glu Gly Trp Arg Ala Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn Asn Tyr Glu Asp Tyr Gly Asp Tyr Trp Arg Gly Asp Tyr Glu
        195                 200                 205

Ala Glu Gly Val Glu Gly Tyr Asn Tyr Asn Arg Asn Gln Leu Ile Glu
    210                 215                 220

Asp Val Glu Asn Thr Phe Lys Glu Ile Lys Pro Leu Tyr Glu Gln Leu
225                 230                 235                 240

His Ala Tyr Val Arg Thr Lys Leu Met Glu Val Tyr Pro Ser Tyr Ile
                245                 250                 255

Ser Pro Thr Gly Cys Leu Pro Ala His Leu Leu Gly Asp Met Trp Gly
            260                 265                 270

Arg Phe Trp Thr Asn Leu Tyr Pro Leu Thr Thr Pro Phe Leu Gln Lys
        275                 280                 285
```

```
Pro Asn Ile Asp Val Thr Asp Ala Met Val Asn Gln Ser Trp Asp Ala
    290                 295                 300

Glu Arg Ile Phe Lys Glu Ala Glu Lys Phe Phe Val Ser Val Gly Leu
305                 310                 315                 320

Pro Gln Met Thr Pro Gly Phe Trp Thr Asn Ser Met Leu Thr Glu Pro
                325                 330                 335

Gly Asp Asp Arg Lys Val Val Cys His Pro Thr Ala Trp Asp Leu Gly
                340                 345                 350

His Gly Asp Phe Arg Ile Lys Met Cys Thr Lys Val Thr Met Asp Asn
            355                 360                 365

Phe Leu Thr Ala His His Glu Met Gly His Ile Gln Tyr Asp Met Ala
370                 375                 380

Tyr Ala Lys Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Pro Ser Asn Phe Gln Glu Asp Asn
                420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
450                 455                 460

Gln Asp Lys Ile Pro Arg Glu Gln Trp Thr Lys Lys Trp Trp Glu Met
465                 470                 475                 480

Lys Arg Glu Ile Val Gly Val Val Glu Pro Leu Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Ile Tyr Gln Phe Gln Phe Gln Glu Ala
            515                 520                 525

Leu Cys Gln Ala Ala Lys His Asp Gly Pro Leu His Lys Cys Asp Ile
530                 535                 540

Ser Asn Ser Thr Glu Ala Gly Gln Lys Leu Leu Asn Met Leu Ser Leu
545                 550                 555                 560

Gly Asn Ser Gly Pro Trp Thr Leu Ala Leu Glu Asn Val Val Gly Ser
                565                 570                 575

Arg Asn Met Asp Val Lys Pro Leu Leu Asn Tyr Phe Gln Pro Leu Phe
                580                 585                 590

Val Trp Leu Lys Glu Gln Asn Arg Asn Ser Thr Val Gly Trp Ser Thr
            595                 600                 605

Asp Trp Ser Pro Tyr Ala Asp Gln Ser Ile Lys Val Arg Ile Ser Leu
610                 615                 620

Lys Ser Ala Leu Gly Lys Asn Ala Tyr Glu Trp Thr Asp Asn Glu Met
625                 630                 635                 640

Tyr Leu Phe Arg Ser Ser Val Ala Tyr Ala Met Arg Glu Tyr Phe Ser
                645                 650                 655

Arg Glu Lys Asn Gln Thr Val Pro Phe Gly Glu Ala Asp Val Trp Val
                660                 665                 670

Ser Asp Leu Lys Pro Arg Val Ser Phe Asn Phe Phe Val Thr Ser Pro
            675                 680                 685

Lys Asn Val Ser Asp Ile Ile Pro Arg Ser Glu Val Glu Glu Ala Ile
690                 695                 700

Arg Met Ser Arg Gly Arg Ile Asn Asp Ile Phe Gly Leu Asn Asp Asn
```

-continued

```
            705                 710                 715                 720
Ser Leu Glu Phe Leu Gly Ile Tyr Pro Thr Leu Lys Pro Pro Tyr Glu
                725                 730                 735

Pro Pro Val Thr Ile Trp Leu Ile Ile Phe Gly Val Val Met Gly Thr
            740                 745                 750

Val Val Val Gly Ile Val Ile Leu Ile Val Thr Gly Ile Lys Gly Arg
        755                 760                 765

Lys Lys Lys Asn Glu Thr Lys Arg Glu Glu Asn Pro Tyr Asp Ser Met
    770                 775                 780

Asp Ile Gly Lys Gly Glu Ser Asn Ala Gly Phe Gln Asn Ser Asp Asp
785                 790                 795                 800

Ala Gln Thr Ser Phe
                805
```

ACE2 ACTIVATION FOR TREATMENT OF HEART, LUNG AND KIDNEY DISEASE AND HYPERTENSION

This application is a national phase application under 35 U.S.C. §371 of International Application No. PCT/CA2003/000882 filed 19 Jun. 2003, which claims priority to U.S. Provisional Application No. 60/389,709 filed 19 Jun. 2002, the contents of which applications are incorporated herein by reference in their entirety.

FIELD OF THE INVENTION

The present invention provides compositions and methods for use in diagnosing and treating heart, lung and kidney diseases, including hypertension, coronary heart disease, heart and kidney failure, lung edema, and lung injury such as in toxic shock or artificial ventilation.

BACKGROUND OF THE INVENTION

Cardiovascular disease will be the number one health care burden of the 21$^{st}$ century, and is predicted to be the most common cause of death worldwide by 2020. A major risk factor for heart disease is high blood pressure. Hypertension is a multifactorial quantitative trait controlled by both genetic and environmental factors. While much is known about environmental factors that can contribute to high blood pressure, such as diet and physical activity, less is known about the genetic factors that are responsible for predisposition to cardiovascular disease. Despite the identification of several putative genetic quantitative trait loci (QTL) associated with hypertension in animal models, none of these loci have been translated into genes. Thus, the molecular and genetic mechanisms underlying hypertension and other cardiovascular diseases remain largely obscure.

One critical regulator of blood pressure homeostasis is the renin-angiotensin system (RAS). The protease renin cleaves angiotensinogen into the inactive decameric peptide angiotensin I (AngI). The action of angiotensin-converting enzyme (ACE) then catalyzes the cleavage of the AngI into the active octomer angiotensin II (AngII), which can contribute to hypertension by promoting vascular smooth muscle vasoconstriction and renal tubule sodium reabsorption. ACE mutant mice display spontaneous hypotension, partial male infertility, and kidney malformations. In humans, an ACE polymorphism has been associated with determinants of renal and cardiovascular function, and pharmacological inhibition of ACE and AngII receptors are effective in lowering blood pressure and kidney disease. In addition, inhibition of ACE and AngII receptors has beneficial effects in heart failure.

Recently a homologue of ACE, termed ACE2, has been identified which is predominantly expressed in the vascular endothelial cells of the kidney and heart. Interestingly, two ACE homologues also exist in flies. Unlike ACE, ACE2 functions as a carboxypeptidase, cleaving a single residue from AngI, generating Ang1-9, and a single residue form AngII to generate Ang1-7. These in vitro biochemical data suggested that, ACE2 modulates the RAS and thus may play a role in blood pressure regulation. The in vivo role of ACE2 in the cardiovascular system and the RAS is not known.

Acton et al. in U.S. Pat. No. 6,194,556, describe the use of ACE2 in diagnosis and therapeutics of ACE2 associated states. The patent stated that ACE2 expression levels increase with hypertension and that antagonists or inhibitors of ACE2 activity would be useful in the treatment of increased blood pressure or related disorders. Canadian patent application no. 2,372,387 provides specific examples of ACE2 inhibitors which, are intended to be useful for the treatment of heart disease, such as hypertension. This again emphasizes the need to inhibit, rather than increase, ACE2 activity. These references, which teach the need to inhibit ACE2 activity, are based only on in vitro experimental data. They do not provide in vivo data, such as knock out mammal data, to characterize ACE2. To date, no ACE2 inhibitors have been approved as pharmaceuticals for treatment of hypertension. Furthermore, the in vivo role of ACE2 in the cardiovascular system and the RAS remains largely unknown. There remains a need to characterize the function of ACE2 in order to be able to design appropriate diagnostic tests and pharmaceuticals for treatment of heart and kidney disease.

SUMMARY OF THE INVENTION

The invention provides a new paradigm for the regulation of the renin-angiotensin system and shows a completely new and unexpected usage of ACE2, in contrast to prediction based on in vitro data (Acton patent) and unexpected in the previous art, as a critical negative regulator of the RAS required for heart function and blood pressure control. Activation of ACE2 is critical for treatment and prevention of heart, lung and kidney disease. The invention shows for the first time that administering an ACE2 activator to an animal prevents and treats hypertension and cardiac and kidney disease, and lung injury.

BRIEF DESCRIPTION OF THE DRAWINGS

Preferred embodiments of the invention will be described in relation to the drawings in which.

a, Northern blot analysis of ACE2 mRNA from kidneys of Sabra SBH/y and SBN/y rats. Upper section shows representation of Northern blots with actin control levels. Lower panel shows relative levels of ace2 message normalized to actin levels. b, Western blot analysis of ACE2 protein levels from kidneys of Sabra SBH/y and their control SBN/y rats, as well as SHR and SHRSP and their control WKY rats. Upper section shows representative Western blots. Systolic blood pressure (BP) in mmHg for the respective Sabra rats is indicated. Lower panel shows relative protein levels of ACE2 corrected for actin. Bars show mean values+/−SEM. *=$p<0.05$, **=$p<0.01$. (n=4, for all groups).

Figure 3A:
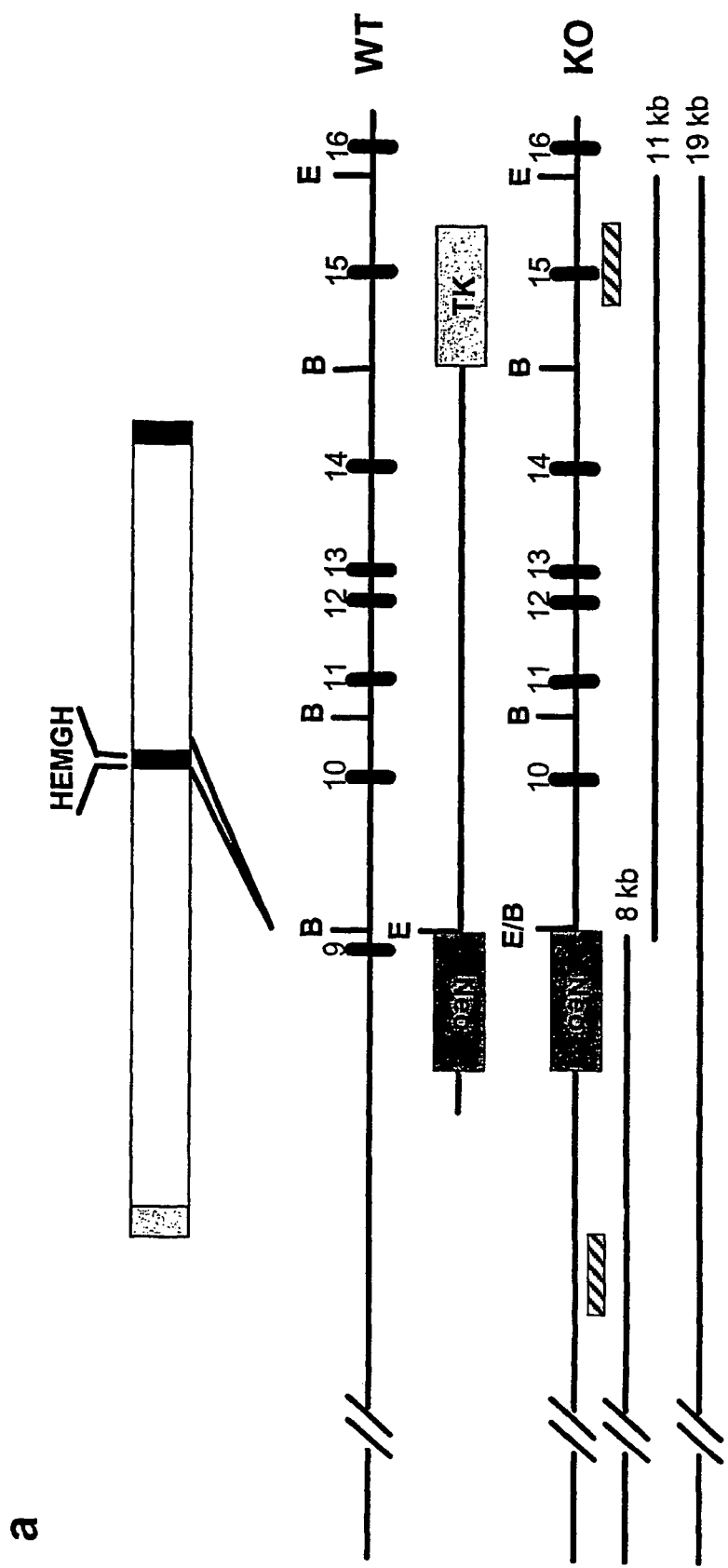

FIG. 3. Targeted disruption of mouse ACE2 by homologous recombination.

a, Gene targeting strategy. A portion of the murine ace2 wild-type locus (top) is shown. Black boxes indicate exons. The targeting vector was designed to replace exon 9 encoding the zinc binding catalytic domain with the neomycin (neo) resistance gene cassette placed in the anti-sense orientation. Thymidine kinase (TK) was used for negative selection. The 3' and 5' flanking probes used for Southern analysis are indicated with a hatched box. b, Southern blot analysis of ace$^{+/y}$ and ace$^{-/y}$ ES cells. Genomic DNA was digested with EcoRI and hybridized to the 3' and 5' flanking probe shown in (a). c, Western blot analysis of ACE2 protein expression in the kidneys of ace2$^{+/y}$ ace$^{-/y}$ mice. The anti-ACE2 Ab is reactive to a region N-terminal to the deletion. d, RT-PCR analysis of ACE mRNA expression in the heart and kidneys of ace2$^{+/y}$ and ace2$^{-/y}$ mice. Different PCR cycles for linear amplification and GAPDH mRNA levels as a control are shown.

FIG. 4. Normal blood pressure and kidney functions a, Blood pressure measurements in 3 month old ace2$^{+/y}$ (n=8) and ace2$^{-/y}$ (n=8) mice in the absence (left panels) or presence of the ACE blocker captopril. Blood pressures were determined by using tail cuffing and mean values+/− SD are shown. Captopril was administered to mice for 2 weeks prior to blood pressure measurements as described in Methods. These blood pressures were confirmed using invasive hemodynamic and Langendorf measurements (not shown). The differences in both captopril-treated ace2$^{+/y}$ and ace2$^{-/y}$ mice are significantly different to that of their respective untreated groups (**p<0.01). b, Normal kidney histologies were seen in 6 month old ace2$^{+/y}$ and ace2$^{-/y}$ mice. Arrows indicate glomeruli.

Figure 5A:
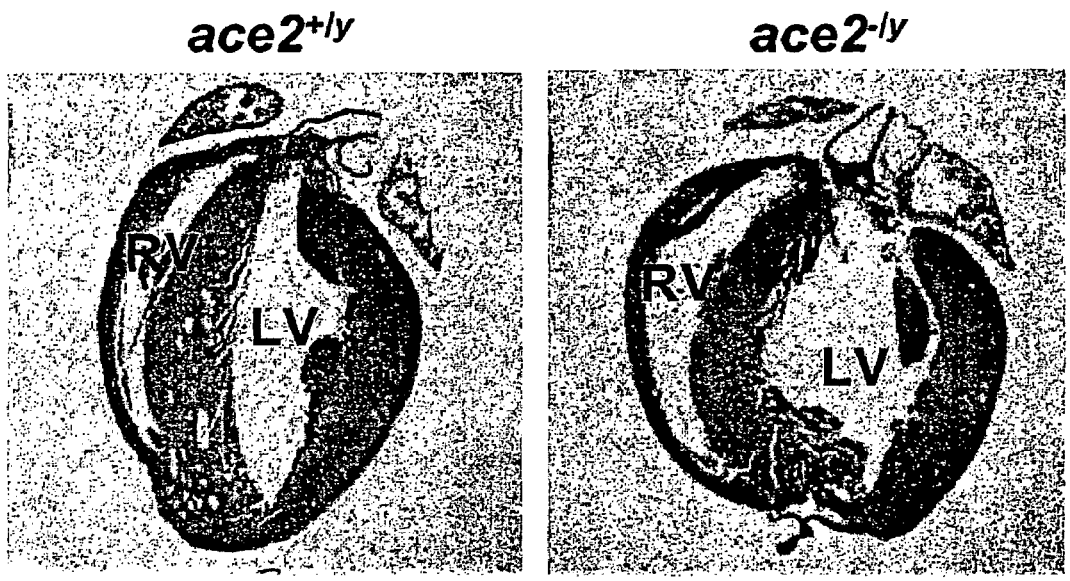
Figure 5B:
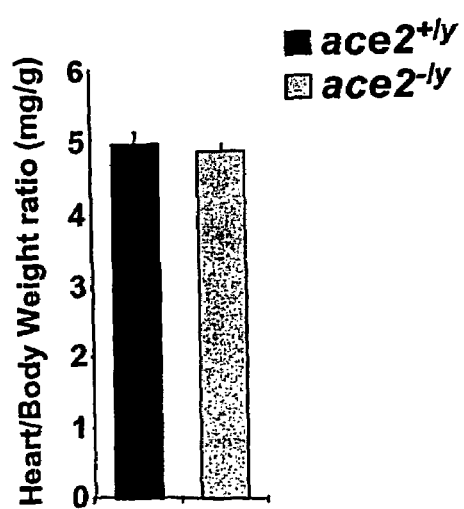

FIG. 5. Heart morphology a, H&E stained sections of hearts isolated from 6 month old ace2$^{+/y}$ and ace2$^{-/y}$ mice. Enlarged left ventricles (LV) and right ventricles (RV) was observed in ace2$^{-/y}$ mice. However, the overall heart size was comparable between both genotypes and there was no evidence of cardiac hypertrophy, macroscopically or in isolated cardiomyocytes. b, Quantitation of heart/body weight ratios from 6 month old ace2$^{+/y}$ (n=8) and ace2$^{-/y}$ (n=8) mice as an indicator of cardiac hypertrophy. It should be noted that the body weights, heart weights, tibial lengths, and the heart weight/tibial length ratios were also not changed between the different genetic groups at all ages analyzed (not shown). c,d, There was an absence of interstitial fibrosis in ace2$^{-/y}$ mice. One hallmark feature for dilated cardiomyopathy is interstitial fibrosis. However, interstitial fibrosis was comparable between the hearts of ace2$^{+/y}$ (n=8) and ace2$^{-/y}$ (n=8) mice. (c) shows PSR staining of individual hearts. Note the normal perivascular fibrosis, stained in red, in both wild type and mutant animals. (d) quantitation of fibrotic changes in the interstitium.

FIG. 6. Loss of ACE2 results in severe contractile heart failure a, Echocardiographic measurements of contracting hearts in a 6 months old ace2$^{+/y}$ and two ace2$^{-/y}$ mice. Peaks and valleys indicate the systole and diastole of individual heart beats. Arrows indicate the distance between systolic contraction (LVESD) and diastolic relaxation (LVEDD), values that determine the percentage of fractional shortening (% FS). Note the increased diastolic and systolic dimensions in the ace2$^{-/y}$ mice indicative of cardiac dilation. The experimental data can be seen in Table 1. b, Percentage fractional shorting and velocity of circumferential fiber shortening, two hallmark parameters for heart contraction was seen, in 6 month old ace2$^{+/y}$ (n=8) and ace2$^{-/y}$ (n=8) mice and 6 month old ace2$^{+/-}$ (n=5) and ace2$^{-/-}$ (n=5) female mice. Values were determined by echocardiography. Mean values+/− SD are shown. * p<0.05 and ** p<0.01 between genetic groups. The experimental data can be seen in Table 1. c, Blood pressure measurements in 6 month old male ace2$^{+/y}$ (n=8) and ace2$^{-/y}$ (n=8) and 6 months old female mice ace2$^{+/-}$ (n=5) and ace2$^{-/-}$ (n=5) female mice. Mean values+/− SD are shown. Blood pressures were confirmed using invasive hemodynamic measurements as can be seen in Table 2. * p<0.05.

Figure 7A:
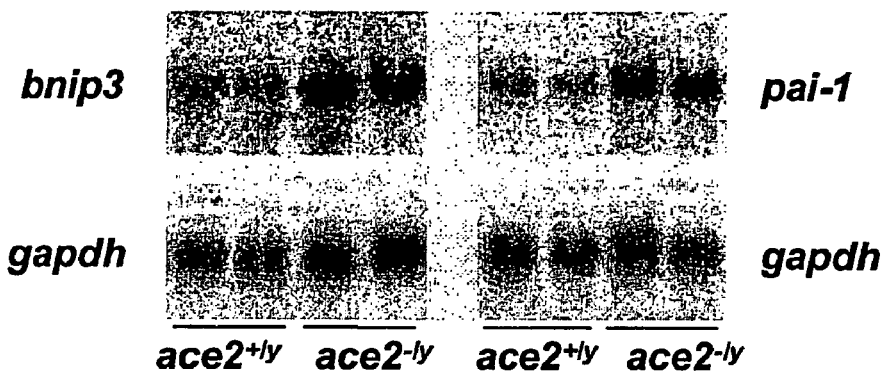
Figure 7B:
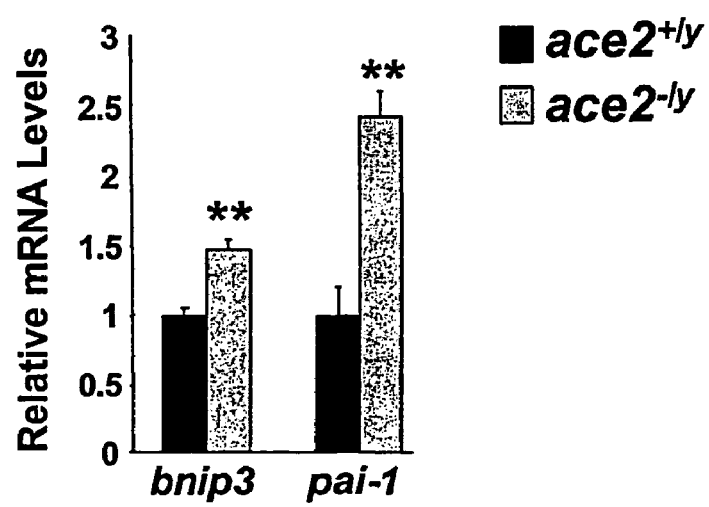
Figure 7C:
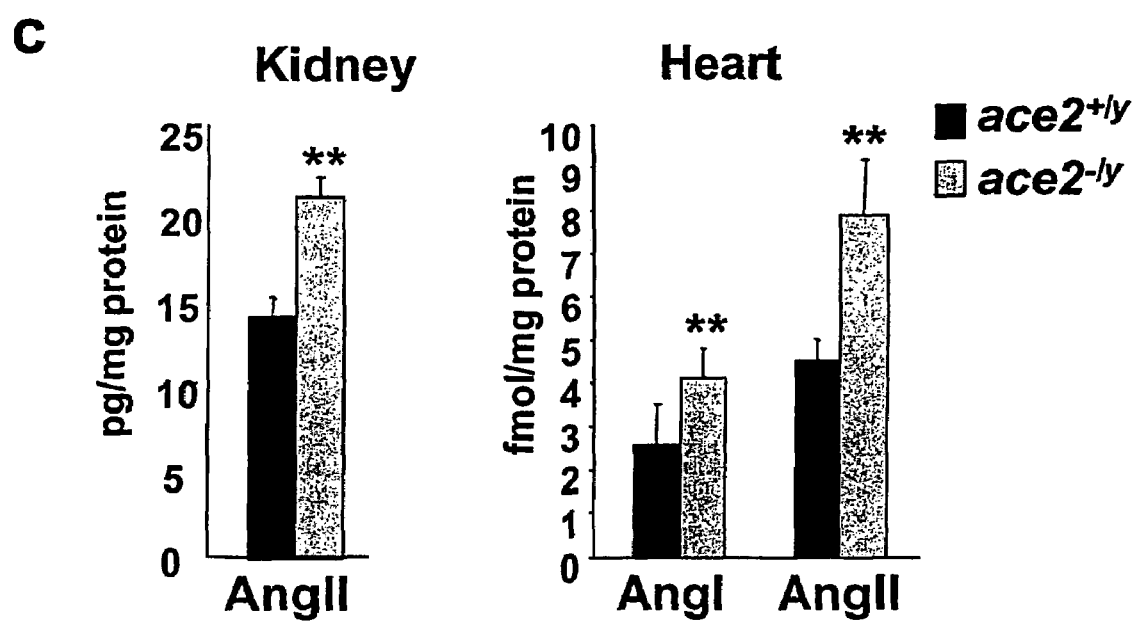

FIG. 7. Up-regulation of hypoxia markers and increased angiotensin II levels in the absence of ACE2 a,b, Northern blot analysis of BNIP3 and PAI-1 mRNA expression levels, two hypoxia-inducible genes in 6 month old male ace2$^{+/y}$ (n=5) and ace2$^{-/y}$ (n=5) mice. (a) shows individual Northern blot data and (b) relative levels of BNIP3 and PAI-1 mRNA levels normalized to the gapdh control. ** p<0.01.

c, AngiotensinI (AngI) and AngiotensinII (AngII) peptide levels in the heart and kidneys of 6 month old male ace2$^{+/y}$ (n=8) and ace2$^{-/y}$ (n=8) littermate mice. AngI and AngII tissue levels were determined by radioimmunoassays. Mean peptide levels+/− SD are shown. ** p<0.01.

Figures 8A, 8B:
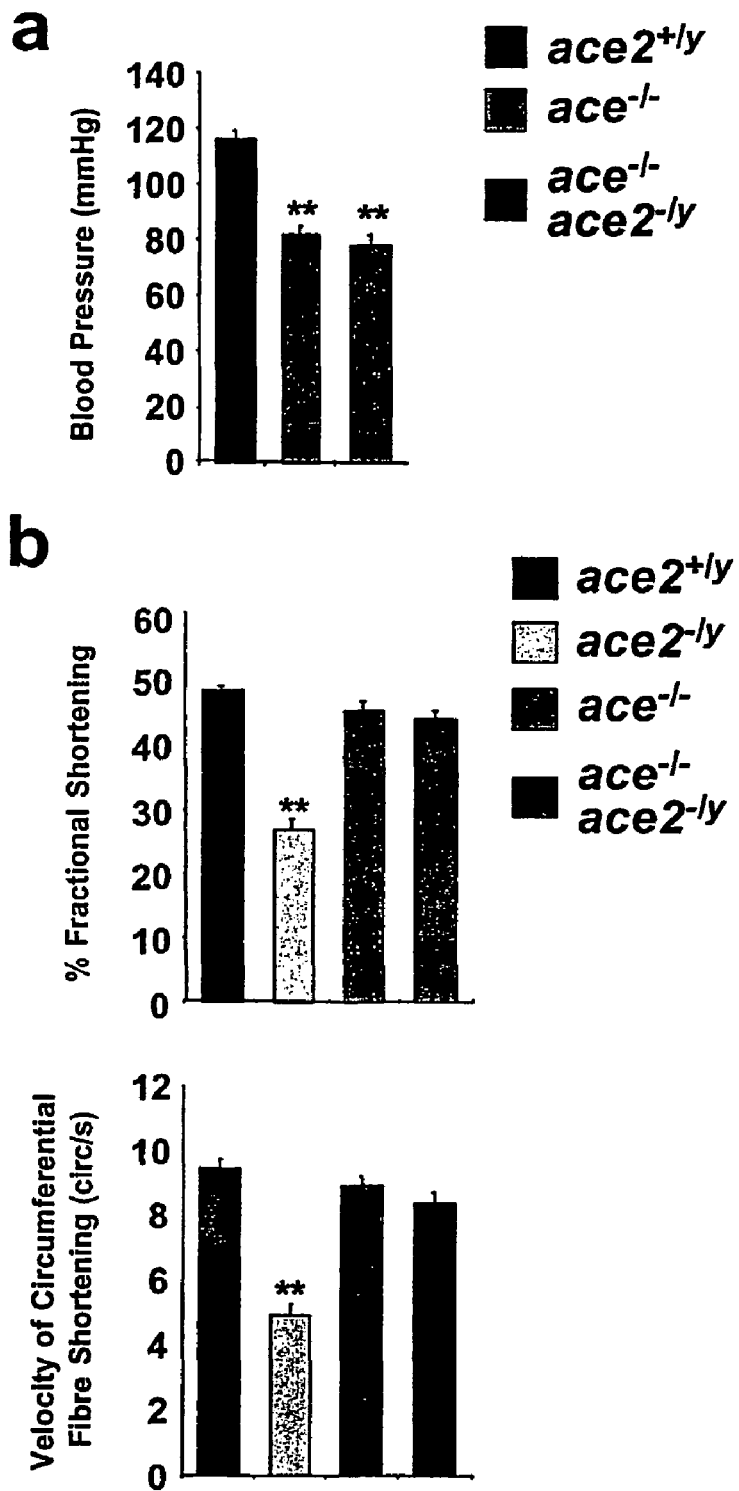
Figure 8C:
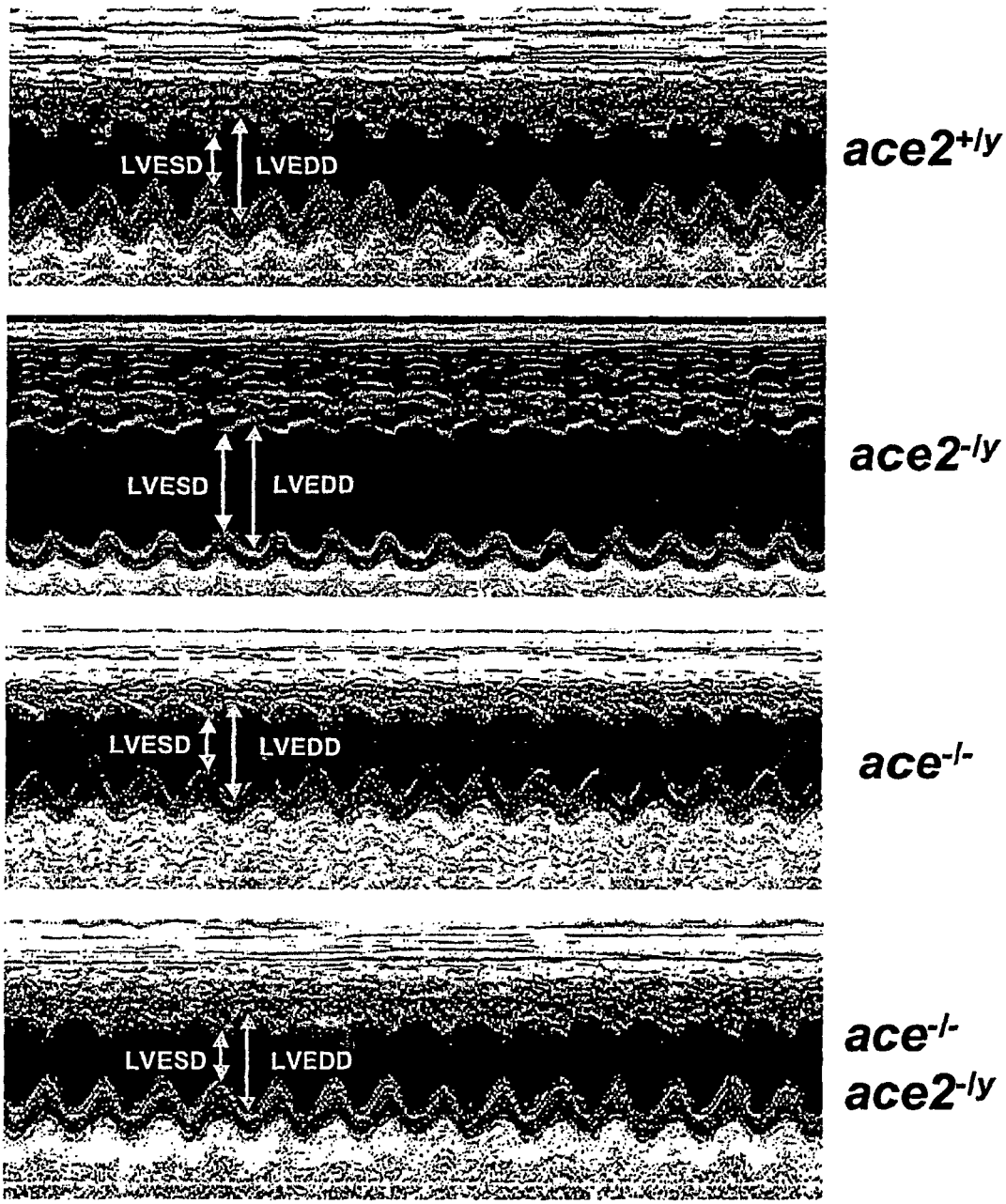

FIG. 8. ACE-ACE2 double mutant mice do not develop heart failure a, Blood pressure measurements in 6 month old male ace2$^{+/y}$ (n=8), ace$^{-/-}$ (n=8), and ace$^{-/-}$ ace2$^{-/y}$ double mutant (n=6) mice. Mean values+/− SD are shown. Blood pressures were confirmed using invasive hemodynamic measurements.  p<0.01 of mutant as compared to wild type mice. b, Percentage fractional shorting and velocity of circumferential fiber shortening in 6 month old male ace2$^{+/y}$ (n=8), ace2$^{-/y}$ (n=8), ace$^{-/-}$ (n=8) and ace$^{-/-}$ ace2$^{-/y}$ double mutant (n=6) littermates. Values were determined by echocardiography. Mean values+/− SD are shown.  p<0.01 between genetic groups. The experimental data can be seen in Table 3. c, Echocardiographic measurements of contracting hearts in a 6 month old male ace2$^{+/y}$, ace2$^{-/y}$, a c e$^{-/-}$, and ace$^{-/-}$ ace2$^{-/y}$ double mutant littermate mice. Echocardiograms were analyzed and are labeled as described in FIG. 6a. Note the ablation of ACE in an ace2 null background completely rescues the contractile heart defects observed in ace2$^{-/y}$ single mutant mice.

Figure 9:
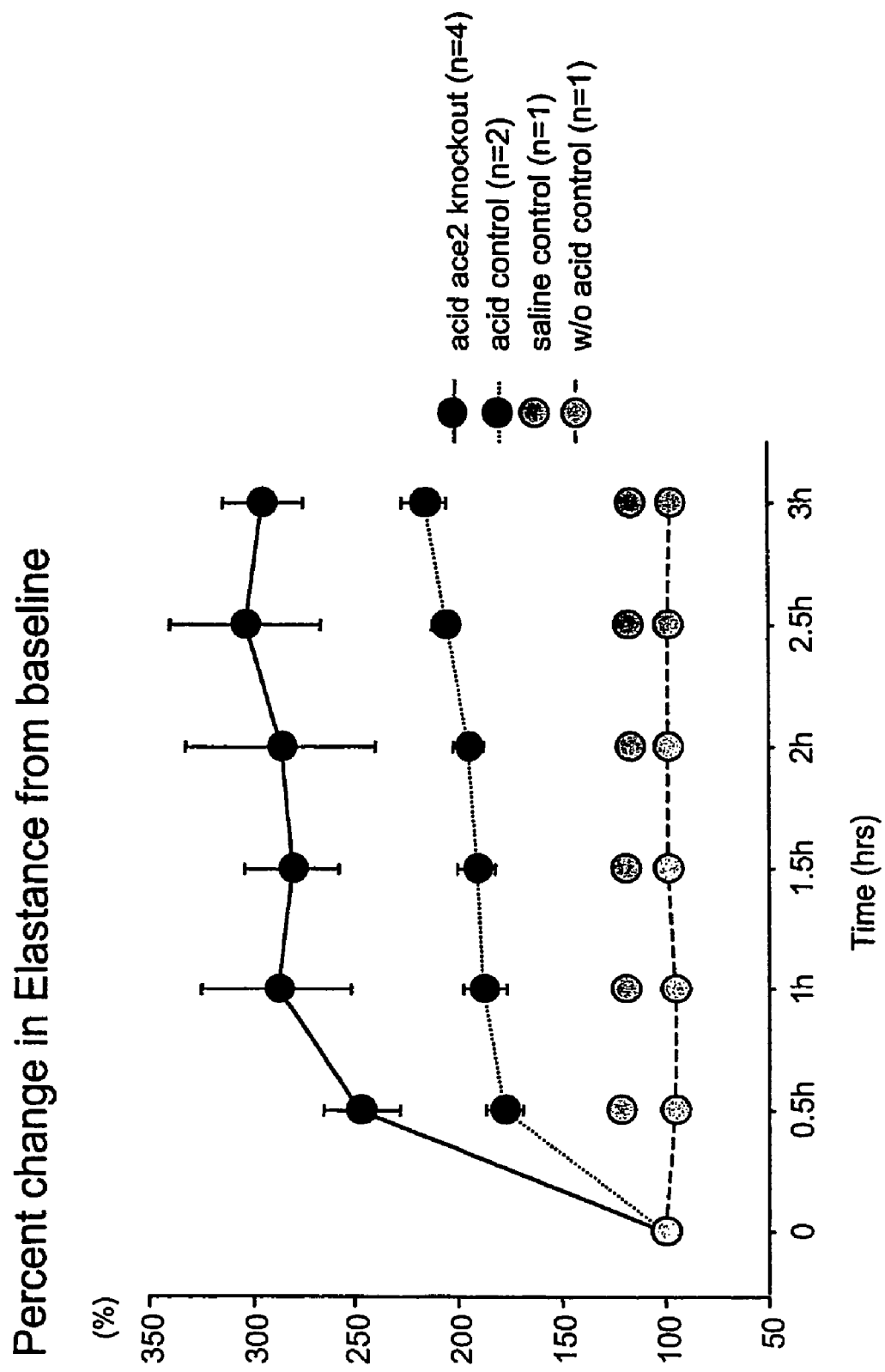

FIG. 9. Percentage change in elastance from baseline was calculated over time. The lung elastance was calculated by dividing tracheal peek pressure with volume.

FIG. 10. a, Human ACE2 DNA (SEQ ID NO:1). b, Human ACE2 polypeptide (SEQ ID NO:2).

FIG. 11. a, Mouse ACE2 DNA (SEQ ID NO:3). b, Mouse ACE2 polypeptide (SEQ ID NO:4)

FIG. 12. ACE2 nucleotide polymorphisms and sequences.

DETAILED DESCRIPTION OF THE INVENTION

The invention provides a new paradigm for the regulation of the RAS system and shows that ACE2 is a critical negative regulator of the RAS required for heart function and cardiovascular function, kidney function and lung injury. Activation of ACE2 is critical for treatment and prevention of heart and kidney disease and hypertension and lung diseases. The invention teaches for the first time that administering an ACE2 activator to an animal prevents and treats heart failure and hypertension, kidney disease and lung injury.

This result is completely unexpected in view of prior art references, such as U.S. Pat. No. 6,194,556 and Canadian patent application no. 2,372,387, described above, that teach that ACE2 activity must be inhibited in order to treat heart disease. It is thus surprising that heart disease is actually treated by activating ACE2 expression and/or activity.

The invention includes activators that include but are not limited to activators of ACE2 function and/or ACE2 mRNA and ACE2 protein expression, and pharmaceutical compositions including the activators. The invention also includes methods of medical treatment of heart disease, lung disease and kidney disease and hypertension by administration of an effective amount of an activator to an animal in need of treatment. Lung disease includes but is not limited to chronic obstructive pulmonary disease, pneumonia, asthma, chromic bronchitis, pulmonary emphysema, cystic fibrosis, interstitial lung disease, primiary pulmonary hypertension, pulmonary embolism, pulmonary sarcodosis, tuberculosis and lung cancers.

The invention also includes screening assays for detecting ACE2 activators, which may be used to treat heart disease and kidney disease and hypertension and lung disease. These assays are in vitro or in vivo. In a preferred embodiment, the invention includes an endothelial, kidney, lung or heart cell assay for evaluating whether a candidate compound is capable of increasing ACE2 expression or activity. Cells are cultured in the presence of at least one compound whose ability to activate expression or activity is sought to be determined and the cells are measured for an increase in the level of ACE2 expression. Another aspect of the invention involves an ACE2 knock-out mouse for identifying compounds that may overcome the effects of loss of ACE2. Polypeptides and small organic molecules are tested in these assays. The invention includes all compounds that are identified with the screening methods of the invention and which are suitable for administration to animals in pharmaceutical compositions.

Another aspect of the invention is the diagnosis of the onset or risk of heart and/or kidney disease and/or hypertension and/or lung disease. This may be diagnosed by measuring ACE2 levels in heart, serum, or kidney, or other tissues. Levels of ACE2 less than wild type levels are indicative of an "ACE2 decreased state" which this invention shows is directly connected with heart and/or kidney disease and/or hypertension, and/or lung disease, or a risk of disease. Wild type levels of ACE2 and decreased levels will be readily apparent to those skilled in the art. An ACE2 decreased state is also indicated by the polymorphisms ACE2a-ACE2m described below. The invention is useful to treat and diagnose diseases associated with decreased ACE2 expression or activity. Diagnosis is also optionally accomplished by analysis of polymorphisms upstream and downstream of and within the ACE2 gene which are associated with an ACE2 reduced state. All the reagents required for the detection of nucleotide(s) that distinguish the polymorphisms, by means described herein, can be provided in a single kit for analysis of isolated genomic DNA from an animal. The kit would contain labelled probes that distinguish polymorphisms of ACE2 in order to allow genotyping and phenotyping, for diagnosis of risk or onset of disease. Polymorphism-specific probes can be appropriately labelled and added to the generated DNA segments under annealing conditions, such that only one of the polymorphism-specific probes hybridizes and can be detected, thereby identifying the specific ACE2 polymorphism.

Therapeutic Methods

As hereinbefore mentioned, the present inventors have shown that ACE2 gene expression is down-regulated in hypertension, heart and kidney disease. Accordingly, the present invention provides a method of treating or preventing hypertension, heart disease, lung or kidney disease comprising administering an effective amount of an agent that can increase the expression of ACE2 to an animal in need thereof.

The term "an agent that can increase the expression of ACE2" as used herein means any agent that can increase the level or activity of an ACE2 gene or protein as compared to the level or activity of the ACE2 gene or protein in the same type of cell in the absence of the agent. The agent can be any type of substance including, but not limited to, nucleic acid molecules (including ACE2 or fragments thereof), proteins (including Ace2 or fragments thereof), peptides, carbohydrates, small molecules, or organic compounds. Whether or not the ACE2 gene is increased can be readily determined by one of skill in the art using known methods including Western blotting SDS-PAGE, immunochemistry, RT-PCR, Northern blotting and in situ hybridization.

The term "animal" as used herein includes all members of the animal kingdom. The animals are preferably human.

The term "effective amount" as used herein means an amount effective at dosages and for periods of time necessary to enhance the level of ACE2.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

Administration of ACE2 Nucleic Acid Molecule

In one embodiment, the expression of the ACE2 gene is increased by administering a nucleic acid that comprises an ACE2 gene or portion thereof.

In another embodiment, the expression of the ACE2 gene may be increased by administering an agent that increases ACE2 gene expression including any agents identified using the screening assays in this application.

Since an animal suffering from disease, disorder or abnormal physical state can be treated by up regulation of ACE2, gene therapy to increase ACE2 expression is useful to modify the development/progression of heart or kidney or lung disease.

The invention includes methods and compositions for providing ACE2 gene therapy for treatment of diseases, disorders or abnormal physical states characterized by decreased ACE2 expression or levels of activity of ACE2 polypeptide.

The invention includes methods and compositions for providing a nucleic acid molecule encoding ACE2 or functionally equivalent nucleic acid molecule to the cells of an animal such that expression of ACE2 in the cells provides the biological activity or phenotype of ACE2 polypeptide to those cells. Sufficient amounts of the nucleic acid molecule are administered and expressed at sufficient levels to provide the biological activity or phenotype of ACE2 polypeptide to the cells. For example, the method can preferably involve a method of delivering a nucleic acid molecule encoding ACE2 to the cells of an animal having cardiovascular or kidney, or lung disease, comprising administering to the subject a vector comprising DNA encoding ACE2. The method may also relate to a method for providing an animal having cardiovascular or kidney, or lung disease with biologically active ACE2 polypeptide by administering DNA encoding ACE2. The method may be performed in vivo or ex vivo (e.g. with heart, lung, endothelial or kidney stem cells, progenitor cells or other cells to be transplanted cells). Methods and compositions for administering ACE2 (including in gene therapy) to isolated cell or an animal are explained, for example, in U.S. Pat. Nos. 5,672,344, 5,645,829, 5,741,486, 5,656,465, 5,547,932, 5,529,774, 5,436,146, 5,399,346, 5,670,488, 5,240,84, 6,322,536, 6,306,830 and 6,071,890 and U.S. Patent Application No. 20010029040 which are incorporated by reference in their entirety.

The method also relates to a method for producing a stock of recombinant virus by producing virus suitable for gene therapy comprising DNA encoding ACE2. This method preferably involves transfecting cells permissive for virus replication (the virus containing the nucleic acid molecule) and collecting the virus produced.

The methods and compositions can be used in vivo or in vitro. The invention also includes compositions (preferably pharmaceutical compositions for gene therapy). The compositions include a vector containing ACE2. The carrier may be a pharmaceutical carrier or a host cell transformant including the vector. Vectors known in the art include but are not restricted to retroviruses, adenoviruses, adeno associated virus (AAV), herpes virus vectors, such as vaccinia virus vectors, HIV and lentivirus-based vectors, or plasmids. The invention also includes packaging and helper cell lines that are required to produce the vector. Methods of producing the vector and methods of gene therapy using the vector are also included with the invention.

The invention also includes a transformed cell containing the vector and the recombinant ACE2 nucleic acid molecule sequences.

Use of ACE2 Variants—Modifications to Polypeptide Sequence

ACE2 variants may be used in methods of the invention. Changes which result in production of a chemically equivalent or chemically similar amino acid sequence are included within the scope of the invention. Polypeptides having sequence identity to ACE2 receptor are tested to ensure that they are suitable for use in the methods of the invention. Variants of the polypeptides of the invention may occur naturally, for example, by mutation, or may be made, for example, with polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine.

Therefore, the invention includes polypeptides having conservative changes or substitutions in amino acid sequences. Conservative substitutions insert one or more amino acids, which have similar chemical properties as the replaced amino acids. The invention includes sequences where conservative substitutions are made that do not destroy compound activity.

Polypeptides comprising one or more d-amino acids are contemplated within the invention. Also contemplated are polypeptides where one or more amino acids are acetylated at the N-terminus. Those with skill in the art recognize that a variety of techniques are available for constructing polypeptide mimetics with the same or similar desired compound activity as the corresponding polypeptide compound of the invention but with more favorable activity than the polypeptide with respect to solubility, stability, and/or susceptibility to hydrolysis and proteolysis. See, for example, Morgan and Gainor, Ann. Rep. Med. Chem., 24:243-252 (1989). Examples of polypeptide mimetics are described in U.S. Pat. No. 5,643,873. Other patents describing how to make and use mimetics include, for example in, U.S. Pat. Nos. 5,786,322, 5,767,075, 5,763,571, 5,753,226, 5,683,983, 5,677,280, 5,672,584, 5,668,110, 5,654,276, 5,643,873. Mimetics of the polypeptides of the invention may also be made according to other techniques known in the art. For example, by treating a polypeptide of the invention with an agent that chemically alters a side group by converting a hydrogen group to another group such as a hydroxy or amino group. Mimetics preferably include sequences that are either entirely made of amino acids or sequences that are hybrids including amino acids and modified amino acids or other organic molecules.

The invention also includes hybrids and polypeptides, for example where a nucleotide sequence is combined with a second sequence.

The invention also includes methods of using polypeptide fragments of ACE2 which may be used to confer compound activity if the fragments retain activity. The invention also includes polypeptides and fragments of the polypeptides of the invention which may be used as a research tool to characterize the polypeptide or its activity. Such polypeptides preferably consist of at least 5 amino acids. In preferred embodiments, they may consist of 6 to 10, 11 to 15, 16 to 25, 26 to 50, 51 to 75, 76 to 100 or 101 to 250 or 250 to 500 amino acids. Fragments may include sequences with one or more amino acids removed, for example, C-terminus amino acids in a compound sequence.

Enhancement of ACE2 Polypeptide Activity

The activity of ACE2 is increased or decreased by carrying out selective site-directed mutagenesis. A DNA plasmid or expression vector containing the nucleic acid molecule or a nucleic acid molecule having sequence identity is preferably used for these studies using the U.S.E. (Unique site elimination) mutagenesis kit from Pharmacia Biotech or other mutagenesis kits that are commercially available, or using PCR. Once the mutation is created and confirmed by DNA sequence analysis, the mutant polypeptide is expressed using an expression system and its activity is monitored.

The invention also includes methods of use of polypeptides which have sequence identity at least about: >20%, >25%, >28%, >30%, >35%, >40%, >50%, >60%, >70%, >80% or >90% more preferably at least about >95%, >99% or >99.5%, to human or mouse ACE2 (or a partial sequence thereof). Modified polypeptide molecules are discussed below. Preferably about: 1, 2, 3, 4, 5, 6 to 10, 10 to 25, 26 to 50 or 51 to 100, or 101 to 250 nucleotides or amino acids are modified.

Identity is calculated according to methods known in the art. Sequence identity is most preferably assessed by the BLAST version 2.1 program advanced search (parameters as above). BLAST is a series of programs that are available on the world wide web at ncbi.nlm.nih.gov/BLAST. The advanced BLAST search (available on the world wide web at ncbi.nlm.nih.gov/blast/blast.cgi?Jform=1) is set to default parameters. (i.e. Matrix BLOSUM62; Gap existence cost 11; Per residue gap cost 1; Lambda ratio 0.85 default).

References to BLAST searches are: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402; Zhang, J. & Madden, T. L. (1997) "PowerBLAST: A new network BLAST application for interactive or automated sequence analysis and annotation." Genome Res. 7:649-656.

Preferably about: 1, 2, 3, 4, 5, 6 to 10, 10 to 25, 26 to 50 or 51 to 100, or 101 to 250 nucleotides or amino acids are modified. The invention includes polypeptides with mutations that cause an amino acid change in a portion of the polypeptide not involved in providing activity or an amino acid change in a portion of the polypeptide involved in providing activity so that the mutation increases or decreases the activity of the polypeptide.

Screening for ACE2 Activators

Small organic molecules are screened to determine if they increase ACE2 expression or activity. Polypeptide fragments of ACE2 as well as polypeptides having sequence identity to ACE2 are also tested to determine if they increase ACE2 activity in vitro assays and in vivo in cell lines. Activators are preferably directed towards specific domains of ACE2 to increase ACE2 activation. To achieve specificity, activators should target the unique sequences of ACE2.

The present invention also includes the isolation of substances that increase ACE2 expression. In particular ligands or substances that can bind to the ACE2 gene or protein may be isolated. Biological samples and commercially available libraries may be tested for substances such as proteins that bind to a ACE2 gene or protein. For example, the amino acid sequence of a ACE2 protein may be used to probe peptide libraries while a nucleic acid sequence encoding ACE2 may be used to probe nucleic acid libraries. In addition, antibodies prepared to ACE2 may be used to isolate other peptides with affinity for ACE2. For example, labelled antibodies may be used to probe phage displays libraries or biological samples.

Conditions which permit the formation of complexes with a substance and a ACE2 gene or protein may be selected having regard to factors such as the nature and amounts of the substance and the ACE2 gene or protein. The substance-protein or substance-gene complex, free substance or non-complexed substance may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against ACE2 or the substance, or labelled protein, or a labelled substance may be utilized. The antibodies, proteins, or substances may be labelled, as appropriate, with a detectable substance as described below.

Once potential binding partners have been isolated, screening methods may be designed in order to determine if the substances that bind to the ACE2 genes or proteins are useful in the methods of the present invention to enhance ACE2 expression on a cell and therefore useful in treating disease.

Therefore, the invention also provides methods for identifying substances which are capable of binding to ACE2 genes or proteins. In particular, the methods may be used to identify substances, which are capable of binding to and augmenting or enhancing expression of the ACE2. Accordingly the invention provides a method of identifying substances, which bind with a ACE2 gene or protein comprising the steps of:

(a) reacting a ACE2 gene or protein, preferably immobilized, and a test substance, under conditions which allow for formation of a complex, and (b) assaying for complexes, for free substance, and for non-complexed gene or protein.

Any assay system or testing method that detects protein-protein interactions may be used including co-immunoprecipitation, crosslinking and co-purification through gradients or chromatographic columns. Additionally, x-ray crystallographic studies may be used as a means of evaluating interactions with substances and molecules. For example, purified recombinant molecules in a complex of the invention when crystallized in a suitable form are amenable to detection of intra-molecular interactions by x-ray crystallography. Spectroscopy may also be used to detect interactions and in particular, Q-TOF instrumentation may be used. Biological samples and commercially available libraries may be tested for ACE2 binding peptides. In addition, antibodies prepared to the ACE2 may be used to isolate other peptides with ACE2 binding affinity. For example, labelled antibodies may be used to probe phage display libraries or biological samples. In this respect peptides may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al. 1992, J. Mol. Biol. 227:711; Devlin et al., 1990 Science 249:404; Cwirla et al. 1990, Proc. Natl. Acad, Sci. USA, 87:6378). Libraries may also be constructed by concurrent synthesis of overlapping peptides (see U.S. Pat. No. 4,708,871). Activators are tested in hypertension, heart or kidney disease model animals.

In one embodiment, the invention includes an assay for evaluating whether a candidate compound is capable of increasing ACE2 expression or activity by culturing cells (preferably kidney or heart cells) in the presence of at least one compound whose ability to activate expression or activity is sought to be determined and thereafter monitoring the cells for an increase in the level of ACE2 expression and/or activity. Increased ACE2 expression and/or activity indicates that the candidate compound is useful for treating heart or kidney disease or hypertension.

A similar screening assay may be done with mammals known in the art that are prone to heart disease or kidney disease. The candidate compound is administered to the mammal and ACE2 expression and/or activity is measured. Increased ACE2 expression and/or activity indicates that the candidate compound is useful for treating heart or kidney disease.

A method of determining whether a candidate compound increases the activity of ACE2 (and is useful for treating cardiovascular disease and/or kidney disease and/or lung, and/or hypertension) can also include:

a) contacting (i) ACE2, a fragment of ACE2 or a derivative of either of the foregoing with (ii) an ACE2 substrate in the presence of the candidate compound; and b) determining whether ACE2 activity on the substrate is increased, thereby indicating that the compound increases the activity of ACE2. Increased ACE2 activity indicates that the compound is useful for treating heart diseases or kidney or lung diseases listed in this application or hypertension. Determination of an increase in ACE2 activity preferably involves determining whether the compound increases ACE2 proteolytic activity (increased hydrolysis of substrates). In a variation of the invention, the assays of the invention are subject to the proviso that the candidate compound is not a sodium-halogen salt or a potassium-halogen salt and the assay is not directed to measuring the effect of increasing ion concentration on ACE2 proteolysis. ACE2 substrates include AngI, AngII, des-Ang, AngII, apelin-13, dynorphin 13, beta-casomorphin and neurotensin.

Methods for producing ACE2 are described in CA 2,372, 387. An example of an in vitro assay for ACE2 activation is shown in Vickers et al., Hydrolysis of biological peptides by human angiotensin-converting enzyme-related carboxypeptidase. J. Biol. Chem. 2002, 277(17):14838. Other assays (as well as variations of the above assays) will be apparent from the description of this invention and techniques such as those disclosed in U.S. Pat. Nos. 5,851,788, 5,736,337 and 5,767,075 which are incorporated by reference in their entirety.

Knock-Out Mammals

Working examples of the cloning of mouse ACE2 and generation of ACE2 knock-out mice are described in the examples below. The term "knockout" refers to partial or complete reduction of the expression of at least a portion of a polypeptide encoded by an ACE2 gene of a single cell, selected cells, or all of the cells of a mammal. The mammal may be a "heterozygous knockout", wherein one allele of the endogenous gene has been disrupted and one allele still exists. In ACE2 on the X chromosome, females may be heterozygous. In males, there is only one allele and males are homozygous. Alternatively, the mammal may be a "homozygous knockout" wherein both alleles of the endogenous gene have been disrupted.

The term "knockout construct" refers to a nucleotide sequence that is designed to decrease or suppress expression of a polypeptide encoded by an endogenous gene in one or more cells of a mammal. The nucleotide sequence used as the knockout construct is typically comprised of (1) DNA from some portion of the endogenous gene (one or more exon sequences, intron sequences, and/or promoter sequences) to be suppressed and (2) a marker sequence used to detect the presence of the knockout construct in the cell. The knockout construct is inserted into a cell containing the endogenous gene to be knocked out. The knockout construct can then integrate within one or both alleles of the endogenous ACE2 gene, and such integration of the ACE2 knockout construct can prevent or interrupt transcription of the full-length endogenous ACE2 gene. Integration of the ACE2 knockout construct into the cellular chromosomal DNA is typically accomplished via homologous recombination (i.e., regions of the ACE2 knockout construct that are homologous or complimentary to endogenous ACE2 DNA sequences can hybridize to each other when the knockout construct is inserted into the cell; these regions can then recombine so that the knockout construct is incorporated into the corresponding position of the endogenous DNA).

Typically, the knockout construct is inserted into an undifferentiated cell termed an embryonic stem cell (ES cell). ES cells are usually derived from an embryo or blastocyst of the same species as the developing embryo into which it can be introduced, as discussed below.

The phrases "disruption of the gene", "gene disruption", "suppressing expression", and "gene suppression", refer to insertion of an ACE2 nucleotide sequence knockout construct into a homologous region of the coding region of the endogenous ACE2 gene (usually containing one or more exons) and/or the promoter region of this gene so to decrease or prevent expression of the full length ACE2 molecule in the cell. Insertion is usually accomplished by homologous recombination. By way of example, a nucleotide sequence knockout construct can be prepared by inserting a nucleotide sequence comprising an antibiotic resistance gene into a portion of an isolated nucleotide sequence encoding ACE2 that is to be disrupted. When this knockout construct is then inserted into an embryonic stem cell ("ES cell"), the construct can integrate into the genomic DNA of at least one ACE2 allele. Thus, many progeny of the cell will no longer express ACE2 at least in some cells, or will express it at a decreased level and/or in a truncated form, as at least part of the endogenous coding region of ACE2 is now disrupted by the antibiotic resistance gene.

The term "marker sequence" refers to a nucleotide sequence that is (1) used as part of a larger nucleotide sequence construct (i.e., the "knockout construct") to disrupt the expression of ACE2 and (2) used as a means to identify those cells that have incorporated the ACE2 knockout construct into the chromosomal DNA. The marker sequence may be any sequence that serves these purposes, although typically it will be a sequence encoding a protein that confers a detectable trait on the cell, such as an antibiotic resistance gene or an assayable enzyme not naturally found in the cell. The marker sequence will also typically contain either a homologous or heterologous promoter that regulates its expression.

Included within the scope of this invention is a mammal in which one or both ACE2 alleles, as well as one or both alleles of another gene(s), have been knocked out. Such a mammal can be generated by repeating the procedures set forth herein for generating an ACE2 knockout mammal but using another gene, or by breeding two mammals, one with one or both alleles of ACE2 knocked out, and one with one or both alleles of a second gene knocked out, to each other, and screening for those offspring that have the double knockout genotype (whether a double heterozygous or a double homozygous knockout genotype, or a variation thereof).

Other knock out animals and cells may be made using similar techniques.

Pharmaceutical Compositions

Activators of ACE2 expression and activity are preferably combined with other components, such as a carrier, in a pharmaceutical composition. These compositions may be administered to an animal, preferably a human, in soluble form to prevent or treat heart disease, kidney disease or hypertension. Heart diseases include chronic heart failure, left ventricular hypertrophy, acute heart failure, myocardial infarction, and cardiomyopathy. Kidney disease includes kidney failure. ACE2 activators are useful for regulating blood pressure and arterial hypertension. Normal blood pressure has a diastolic blood pressure of less than 85 mm Hg. High normal blood pressure has a diastolic blood pressure between 85 and 89 mm Hg. Mild hypertension corresponds to a diastolic blood pressure between 90-104 mm Hg. Moderate hypertension has to a diastolic blood pressure between 105 and 114 mm Hg. Severe hypertension has a diastolic blood pressure higher than 115 mm Hg. Abnormal blood pressure is also determined from the systolic blood pressure (when the diastolic pressure is less than 90 mm Hg). Normal blood pressure has a systolic blood pressure of less than 140 mm Hg. Borderline systolic hypertension shows a systolic blood pressure between 140 and 159 mm Hg. Isolated systolic hypertension has a systolic blood pressure higher than 160 mm Hg. (Cecil: Essentials of Medicine, Third Edition by Andreoli et al. W.B. Saunders Company (1993)). Hypertension is diagnosed in an adult over 18 years old if the average of two or more blood pressure measurements on at least two visits is 90 mm Hg or higher diastolic or 140 mm Hg systolic. Children and pregnant women have a lower blood pressure, so a blood pressure over 120/80 (i.e., 120 mm Hg systolic blood pressure/80 mm Hg diastolic blood pressure) indicates hypertension.

The pharmaceutical compositions can be administered to humans or animals by a variety of methods including, but not restricted to topical administration, oral administration, aerosol administration, intratracheal instillation, intraperitoneal injection, and intravenous injection. Dosages to be administered depend on patient needs, on the desired effect and on the chosen route of administration. Polypeptides may be introduced into cells using in vivo delivery vehicles such as but not exclusive to liposomes.

The pharmaceutical compositions can be prepared by known methods for the preparation of pharmaceutically acceptable compositions which can be administered to patients, such that an effective quantity of the nucleic acid molecule or polypeptide is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA).

On this basis, the pharmaceutical compositions could include an active compound or substance, such as a nucleic acid molecule or polypeptide, in association with one or more pharmaceutically acceptable vehicle or diluent, and contained in buffered solutions with a suitable pH and isoosmotic with the physiological fluids. The methods of combining the active molecules with the vehicles or combining them with diluents is well known to those skilled in the art. The composition could include a targeting agent for the transport of the active compound to specified sites within tissue.

Heterologous Overexpression of ACE2

Expression vectors are useful to provide high levels of ACE2 expression. Cell cultures transformed with the nucleic acid molecules of the invention are useful as research tools, particularly for studies of ACE2 decreased states. The invention includes vectors selective for heart cells and kidney cells preferably endothelial cells which normally make ACE2. The invention also includes transfected cells including these vectors. Examples of vectors for heart and kidney cells are described, for example, in Rosengart et al. U.S. Pat. No. 6,322,536; March et al. U.S. Pat. No. 6,224,584; Hammond et al. U.S. Pat. No. 6,174,871; Wolfgang-M. Franz et al. Analysis of tissue-specific gene delivery by recombinant adenoviruses containing cardiac-specific promoters. Cardiovascular Research 35(1997) 560-566; Rothmann T. et al. Heart muscle-specific gene expression using replication defective recombinant adenovirus. Gene Ther 1996 October;3(10): 919-26; Phillips M I et al. Vigilant vector: heart-specific promoter in an adeno-associated virus vector for cardioprotection. Hypertension 2002, February; 39(2 Pt 2):651-5; Herold BC et al. Herpes simplex virus as a model vector system for gene therapy in renal disease. Kidney Int 2002 January;61 Suppl 1:3-8; Figlin R A et al. Technology evaluation: interleukin-2 gene therapy for the treatment of renal cell carcinoma. Curr Opin Mol Ther 1999 April;1(2):271-8; Varda-Bloom N et al. Tissue-specific gene therapy directed to tumor angiogenesis. Gene Ther 2001 June;8(11):819-27; Scott-Taylor TH et al. Adenovirus facilitated infection of human cells with ecotropic retrovirus. Gene Ther 1998 May;5(5): 621-9; Langer J C et al. Adeno-associated virus gene transfer into renal cells: potential for in vivo gene delivery. Exp Nephrol 1998 May-June;6(3):189-94; Lien Y H et al. Gene therapy for renal diseases. Kidney Int Suppl 1997 October;61:S85-8; and Ohno K et al. Cell-specific targeting of Sindbis virus vectors displaying IgG-binding domains of protein A. Nat Biotechnol 1997 August;15(8):763-7.

Cell cultures, preferably heart and kidney cell cultures and endothelial cell cultures, are used in overexpression and research according to numerous techniques known in the art. For example, a cell line (either an immortalized cell culture or a primary cell culture) may be transfected with a vector containing a ACE2 nucleic acid molecule (or molecule having sequence identity) to measure levels of expression of the nucleic acid molecule and the activity of the nucleic acid molecule and polypeptide. The cells are also useful to identify compounds that bind to and activate the polypeptide.

Diagnostic Kits Measuring ACE2 Activity and/or Expression

The measurement of ACE2 expression or activity is also used in: i) diagnosis of heart or kidney disease, lung disease and/or hypertension ii) identifying patients at risk of developing such disease prior to the development of disease iii) measuring therapeutic response in patients having heart disease such as coronary artery disease, chronic heart failure, or kidney disease and/or hypertension and/or lung injury and iv). measuring the success of interventional disease preventive strategies in such patients at risk. The invention includes a method for assessing the levels of ACE2 in an animal comprising the following steps: (a) preparing a heart or kidney or lung sample from a specimen collected from the animal; (b) testing for the presence of ACE2 in the sample; and (c) correlating the presence or levels of ACE2 in the sample with the presence (or risk) of disease such as heart or kidney or lung disease in the animal. ACE2 levels below normal or low ACE2 activity indicate the presence or risk of disease.

Diagnostic Kits Based on ACE2 Single Nucleotide Polymorphisms

This invention also shows that decreased human ACE2 expression results from polymorphisms that control ACE2 gene expression. The QTL mappings in the rats show that there is a 100% correlation between reduced expression levels of ACE2 and hypertension and cardiovascular and kidney disease. None of the polymorphisms described below are found within the ACE2 coding region. All are upstream or downstream of the ACE2 coding region. None of these polymorphisms or their role in cardiovascular disease, kidney disease, lung disease and hypertension were previously known. A particular SNP haplotype is associated with increased risk of disease. This haplotype is an important diagnostic tool for the assessment of risk of disease and for the determination of appropriate medical treatment.

The polymorphisms are as follows:

| SNP name | SNP description | African Am | Asian | Caucasian | Reference |
|---|---|---|---|---|---|
| ACE2a rs879922 | C(C/G) | 60 | 100 | 70 | C |
| ACE2b rs757066 | T(C/T) | 100 | 100 | 70 | T |
| ACE2c rs714205 | C(C/G) | 70 | 50 | 80 | C |
| ACE2d rs329442 | C(A/C) | 50 | 90 | 90 | A/C |
| ACE2e rs233574 | C(C/T) | 80 | 100 | 60 | C |
| ACE2f rs1978124 | C(C/T) | 90 | 100 | 50 | C |
| ACE2g rs1514282 | A(A/G) | 70 | 100 | 100 | A |
| ACE2h rs1514282-2 | A(A/G) | 20 | 50 | 30 | A |
| ACE2i rs1514281 | A(A/G) | 70 | 100 | 100 | A |
| ACE2j rs1514281-2 | A(A/G) | 20 | 50 | 50 | A |

-continued

| SNP name | SNP description | African Am | Asian | Caucasian | Reference |
|---|---|---|---|---|---|
| ACE2k rs1514279 | A(A/G) | Failed | 100 | 70 | A |
| ACE1 2 rs1514280 | C(C/T) | 80 | 100 | 80 | C |
| ACE2m rs233575 | C(C/T) | 100 | 100 | 50 | C |

The nucleotide number of the polymorphisms that control ACE2 gene expression, as described in the chart above and in FIG. 11, can be readily determined by a person skilled in the art.

The chart shows the percentage of the reference base found in each of the three populations in the chart (African American, Caucasian, Asian). For example, for SNP rs233574, the predicted SNP is C/T, with the reference peak being C. In this case, the African American allele frequency is 80% C; the Asian allele frequency is 100% C (in other words, a monomorphic marker); and the Caucasian allele frequency is 60% C.

The present invention provides polynucleotide probes which can be used to determine an animal's genotype which is whether a person is homozygous for one or the other of the polymorphisms, or heterozygous for these polymorphisms, and by extension, the person's phenotype. The phenotype indicates the amount of ACE2 expression in the person's cells. Further, the invention provides methods of using such polynucleotides in such genotype and phenotype determinations. The oligonucleotides of the invention can be used as probes to detect nucleic acid molecules according to techniques known in the art (for example, see U.S. Pat. Nos. 5,792,851 and 5,851,788).

For example, a polynucleotide of the invention may be converted to a probe by being end-labelled using digoxigenin-11-deoxyuridine triphosphate. Such probes may be detected immunologically using alkaline-phosphate-conjugated polyclonal sheep antidigoxigenin F(ab) fragments and nitro blue tetrazolium with 5-bromo-4-chloro-3-indoyl phosphate as chromogenic substrate.

Thus, in accordance with one aspect of the present invention, a polynucleotide probe is provided that selectively hybridizes to a portion of the ACE upstream or downstream sequence. A probe may be designed to hybridise to one ACE2 polymorphism under stringent conditions but not the other polymorphisms in order to distinguish a particular polymorphism.

The polymorphism-specific polynucleotide hybridization probes of the invention may comprise, for example, genomic DNA or synthetic DNA. Such oligonucleotide probes can be synthesised by automated synthesis and will preferably contain about 10-30 bases, although as understood in the oligonucleotide probe hybridization assay art, as few as 8 and as many as about 50 nucleotides may be useful, depending on the position within the probe where the potential mismatch with the target is located, the extent to which a label on the probe might interfere with hybridization, and the physical conditions (e.g., temperature, pH, ionic strength) under which the hybridization of probe with target is carried out. In accordance with conventional procedures, the design of a polynucleotide probe according to the present invention preferably involves adjusting probe length to accommodate hybridization conditions (temperature, ionic strength, exposure time) while assuring polymorphism-specificity.

In accordance with another aspect of the present invention, a test kit for genotyping is provided comprising:
(a) means for amplifying nucleic acid that comprises at least a portion of an ACE2 5' or 3' region, wherein the portion includes a nucleotide corresponding to one of ACE2a-ACE2m; and
(b) a polynucleotide probe of the invention, that distinguishes one ACE2 polymorphism from the other.

The "means for amplifying" will, as the skilled will readily understand, depend on the amplification method to be used. Thus, for example, these means might include suitable primers, a suitable DNA polymerase, and the four 2'-deoxyribonucleoside triphosphates (dA, dC, dG, dT), if amplification is to be by the PCR method. To cite another example, if the amplification is to be by a method relying on transcription, such as the 3SR method, the means will include two primers, at least one of which, when made double-stranded, will provide a promoter, an RNA polymerase capable of transcribing from that promoter, a reverse transcriptase to function in primer-initiated, DNA-directed and RNA-directed, DNA polymerization and possibly also in RNAse H degradation of RNA to free DNA strands from RNA/RNA hybrids, the four ribonucleoside triphosphates (A, C, G and U), and the four 2'-deoxyribonucleoside triphosphates. In another example, if the amplification is by the ligase chain reaction, the means will include two oligonucleotides (DNAs) and a suitable DNA ligase that will join the two if a target, to which both can hybridize adjacent to one another in ligatable orientation, is present.

The oligonucleotide probes of the invention will preferably be labelled. The label may be any of the various labels available in the art for such probes, including, but not limited to $^{32}P$; $^{35}S$; biotin (to which a signal generating moiety, bound to or complexed with avidin can be complexed); a fluorescent moiety; an enzyme such as alkaline phosphatase (which is capable of catalysing a chromogenic reaction); digoxigenin, as described above; or the like.

RFLP analysis, electrophoretic SSCP analysis or sequencing analysis may also be used to detect an ACE2 polymorphism.

There has also been provided, in accordance with another aspect of the present invention, a method of typing for an ACE2 polymorphism-specific target sequence in a ACE2 nucleic acid derived from an animal, comprising the steps of,
(a) obtaining, by a target nucleic acid amplification process applied to DNA from heart or kidney, an assayable quantity of amplified nucleic acid with a sequence that is that of a subsequence (or the complement of a subsequence) of an upstream or downstream region of ACE2, said subsequence including a nucleotide where an ACE2 polymorphism may occur; and
(b) analyzing (e.g., in a nucleic acid probe hybridization assay employing a polynucleotide probe according to the invention) the amplified nucleic acid obtained in step (a) to determine the base or bases at the polymorphism position.

In one application of the typing methods of the invention, the methods are applied to an individual to determine whether the individual is at risk of developing heart or kidney disease.

People with coronary artery disease and/or following bypass surgery, have cardiac hypoxia. It is also known as cardiac stunning or cardiac hibernation. These patients display little structural changes in the heart but have reduced heart function. It is very uncommom to have altered heart function in the absence of structural changes. In mouse models of cardiac stunning or hypoxia, the animals have a phenotype that precisely resemble that of ACE2 mice. In addition, we have shown that markers of hypoxia are induced in the ACE2 deficient mice. Taken together our data show that these mice have reduced heart function due to chronic hypoxia, and thus are models of coronary artery disease. Thus, the polymorphisms and/or reduced ACE2 expression or activity may be used to diagnose this state in humans. Another example is to test whether the function of the heart in patients with dilated cardiomyopathy and show that the disease outcome is associated with ACE2 polymorphisms. Increasing ACE2 expression and activity may be used to treat this state.

Characterization of ACE2 as a Negative Regulator of the RAS

ACE2 maps to a QTL associated with hypertension in three rat models of high blood pressure and ACE2 levels are reduced in all of these hypertensive rat strains. In mice, genetic inactivation of ACE2 using homologous recombination results in increased AngII peptide levels in tissues, upregulation of hypoxia genes in heart, and severe cardiac dysfunction. Ablation of ACE expression on an ace2-deficient background completely abolished the heart failure phenotype of ace2 single knockout mice. These data provide a new paradigm for the regulation of the RAS and identify ACE2 as a negative regulator of the RAS that controls heart function.

ACE2 and Blood Pressure Control.

Most cardiovascular diseases are multifactorial quantitative traits controlled by both genetic and environmental factors. One major factor for cardiovascular disease is the RAS. In contrast to ACE which is ubiquitously expressed, the recently identified ACE2 displays tissue-specific expression. ACE2 regulates endogenous AngII levels, by competing with ACE for its AngI substrate and/or by cleaving AngII to generate Ang1-7. Prior to this invention, nothing was known about the in vivo role of ACE2 in the cardiovascular system. ACE2 regulates endogenous levels of AngII. It also functions as a negative regulator of the RAS.

In three different rat strains that develop spontaneous or diet-induced hypertension and cardiovascular disease, ACE2 maps within a defined QTL on the X chromosome. In all of these hypertension susceptible rat strains, ACE2 mRNA and protein levels were downregulated. The SS-X locus identified in QTL analysis in Sabra rats was also identified as a locus that confers resistance to salt loading. The reduction in ACE2 in the salt sensitive strain and the absence of any alteration in its expression in the resistant strain shows that ACE2 confers resistance to diet-induced blood pressure changes.

The map position and reduced expression show that ACE2 is the gene contributing to the hypertensive QTL on the X-chromosome. Moreover, increased AngI and AngII expression in ace2 null mice confirm that ACE2 is a regulator of the RAS system in vivo. However, loss of ACE2 in our mice did not result in any direct changes in blood pressure even when ACE function was blocked. Blood pressure changes only occurred when extreme cardiac dysfunction was present in older male mice. The genetic factors that contribute to hypertension do not by themselves alter blood pressure. Rather, these QTL define single determinants of blood pressure, which in concert with other genetic polymorphisms promote the change in blood pressure. We identified the association of ACE2 polymorphisms with high blood pressure in the human population. Importantly, our data shows that ACE2 functions as a negative regulator of increased blood pressure.

ACE2 and the Control of Heart Function.

Unexpectedly, loss of ACE2 in mice results in profound contractile dysfunction leading to severe reduction of systemic blood pressure in older mice. Importantly, this cardiac dysfunction is completely reversed by the disruption of ACE suggesting that a catalytic product of ACE triggers contractile impairment in the absence of ACE2. Since these contractility defects can occur in the absence of hypertrophy or any detectable changes in blood pressure, our data also provides genetic proof that the RAS regulated heart disease phenotype can be genetically uncoupled from its effects on blood pressure and cardiac hypertrophy.

ACE inhibitors and AngII receptor blockers have been shown to have a cardioprotective role in heart failure in humans, thus implicating AngII in cardiac disease. The complete abolition of the cardiac dysfunction in our ace/ace2 double mutant mice shows that the RAS directly controls heart function and that ACE2 is a critical negative regulator that antagonizes the RAS and heart failure. Our genetic rescue experiments strongly indicate that it is in fact a product of ACE that drives heart failure, i.e., the increase in AngII seen in the hearts of ace2 null mice is causative for cardiac dysfunction. Whether pharmacological inhibition of the AngII receptor rescues the heart phenotypes of ace2 mutant mice needs to be determined. Interestingly, our results in flies show that a P-element mutation associated with the ACE homologue, ACER, results in a severe and lethal defect of heart morphogenesis (data not shown) showing that the ACE/ACE2 functions in the heart have been conserved through evolution.

The defect in the ace2 mutant hearts is characterized by severe contractile dysfunction and up-regulation of hypoxia-regulated genes with only slight remodeling in older mice, no hypertrophy and no evidence of myocyte loss. These phenotypic and molecular parameters of failing hearts in ace2 mutant mice are different from hypertrophy and dilated cardiomyopathy. Rather intriguingly, ace2 mutant hearts resemble cardiac stunning and hibernation found in human cases of coronary artery disease and in cases of by-pass surgery. In these human diseases and in animal models of cardiac stunning/hibernation, chronic hypoxic conditions lead to compensatory changes in myocyte metabolism, upregulation of hypoxia-induced genes, and reduced heart function. Since ACE2 is expressed in the vascular endothelium, and not cardiac myocytes, it is likely that the effects of ACE2 are confined to the vasculature. For instance, local increases in AngII could lead to vasoconstriction resulting in hypoperfusion and hypoxia. AngII has also been shown to cause endothelial dysfunction via the induction of oxidative stress. The mechanisms by which loss of ACE2 can result in the upregulation of hypoxia-inducible genes needs to be determined. Importantly, our data show that ACE2 polymorphisms cause the pathology of coronary heart disease in humans.

EXAMPLES

ACE2 Maps to a QTL on the X-Chromosome in Three Hypertensive Rat Strains.

Figure 1:
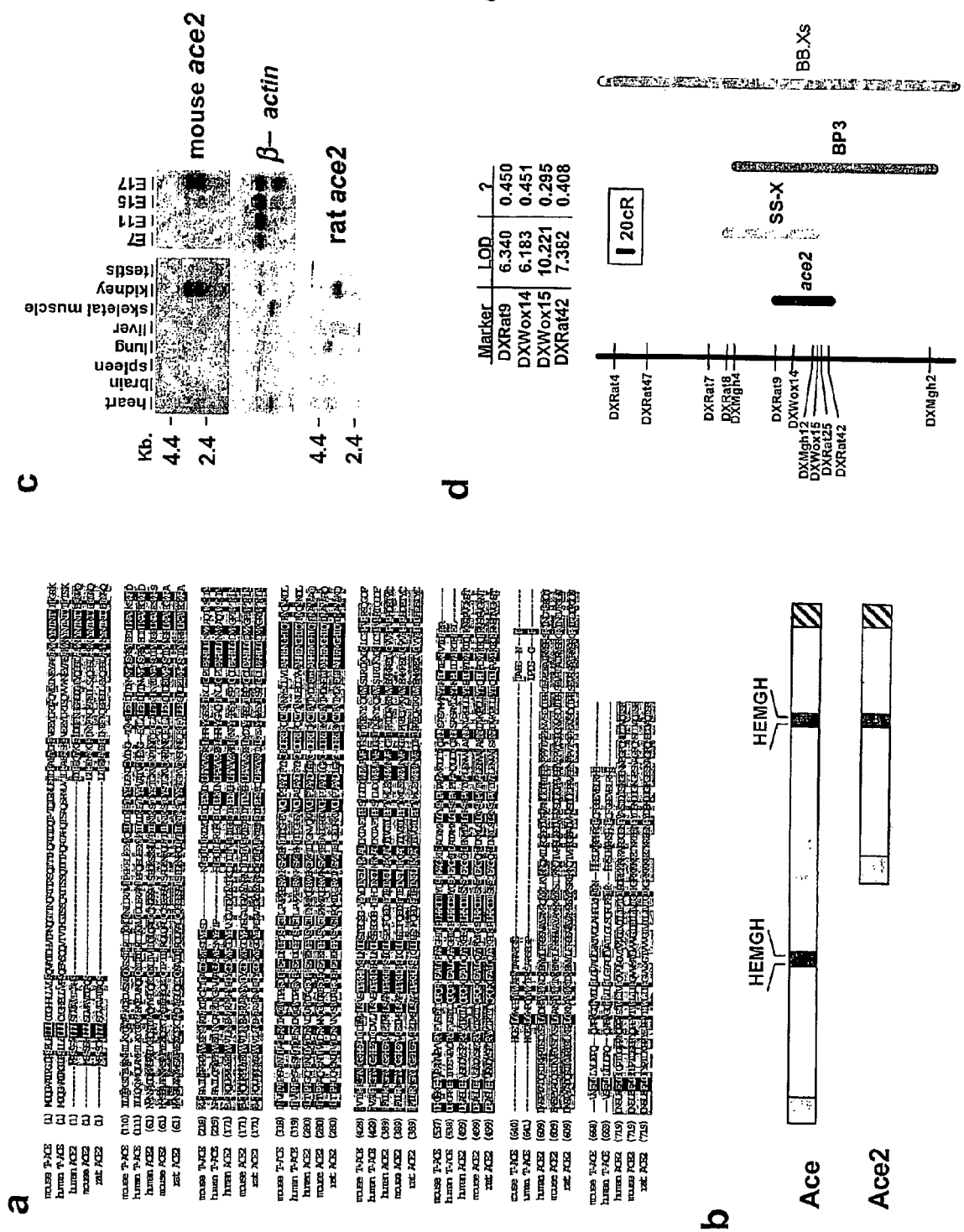
FIG. 1. Sequence and chromosomal mapping of rat ACE2. a, Protein alignment of rat, mouse and human ACE2, with mouse and human testis-ACE (T-ACE). Blackened shading indicates amino acid identity and gray shading indicates degree of amino acid similarity. b, Schematic domain structure of ACE and ACE2. Note that ACE2 only contains one ACE-domain with the consensus zinc binding site HEMGH. The catalytic centers are indicated in black, the signal peptide is indicated in grey and the transmembrane domain in hatched lines. c, Expression patterns of mouse and rat ACE2 genes in different adult tissues and different days of embryonic development (E7=embryonic day 7). Note that two isoforms are present for ACE2 in mice, but not in rat or human (not shown), a feature similar to that seen for ACE[15]. d, Results of radiation hybrid mapping of rat ACE2, compared to the mapping of a QTL identified in Sabra salt-sensitive animals (SS-X), SHRSP (BP3), and SHR rats (BB.Xs). Polymorphic marker names are indicated to the left of the ideogram. LOD scores and theta values for markers linked to ACE2 are shown. cR=centiRads.

Hypertension and most cardiovascular diseases are multifactorial in nature and disease pathogenesis is influenced by multiple genetic susceptibility loci. In various recombinant rat models, multiple QTL for hypertension have been identified. Since ACE2 maps to the X-chromosome in human and a QTL has been mapped to the X-chromosome in several rat models of hypertension with no candidate gene ascribed to it as yet, ACE2 could be a candidate gene for this QTL. To facilitate chromosomal mapping of rat ACE2, the full-length rat ACE2 cDNA was cloned by screening a rat kidney cDNA library. Rat ACE2 is highly homologous to human ACE2 and is 32% identical and 42% similar to human and mouse ACE (FIG. 1a). Like human ACE2, the rat gene is comprised of a single ACE domain with a conserved zinc binding site, a signal peptide and a transmembrane domain (FIG. 1b). Similar to human, ACE2 in mouse and rat is predominantly expressed in kidney and heart, with weaker expression in lung and liver (FIG. 1c).

Radiation hybrid mapping showed that the rat ACE2 gene maps on the X-chromosome with significant LOD scores to markers DXRat9, DXWox14, DXWox15 and DXRat42, placing ace2 between DXRat9 and DXRat42 (FIG. 1d). Comparative mapping showed that the ace2 map position overlaps with a QTL interval for hypertension identified in Sabra salt-sensitive rats found between markers DXMgh12 and DXRat8 (SS-X). Moreover, the chromosomal ace2 region maps to the B P3 QTL interval defined in stroke-prone spontaneously hypertensive rats (SHRSP) rats, and a previously identified hypertensive BB.Xs QTL identified on the X-chromosome of spontaneous hypertensive rats (SHR) by congenic analysis (FIG. 1d). Thus, ACE2 maps to a QTL on the rat X-chromosome identified in three separate models of spontaneous and diet-induced hypertension.

Downregulation of ACE2 Expression in Hypertensive Rats

Figure 2A:
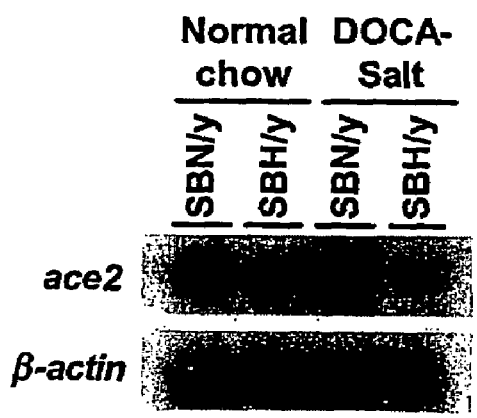
FIG. 2. Expression levels of ACE2 in rat models of hypertension.
Figure 2A:
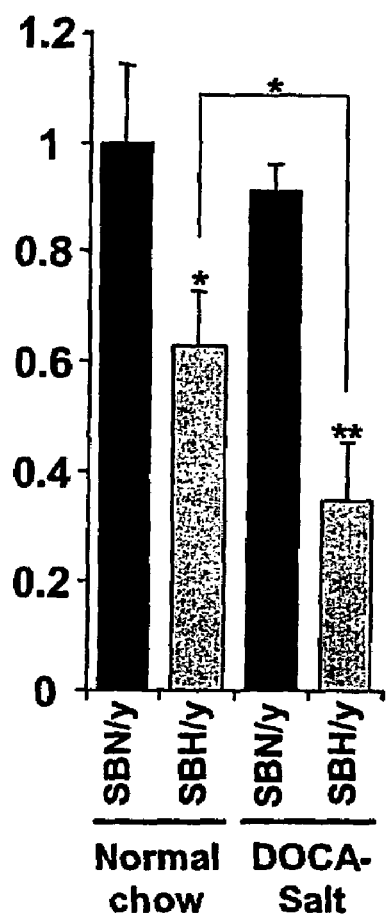

Since the kidney is a major site of blood pressure regulation, ACE2 expression levels in the kidneys of these three hypertensive rat strains was determined. ACE2 mRNA levels were initially measured in the kidneys of salt-sensitive Sabra hypertensive (SBH/y) rats and control salt-resistant Sabra normotensive (SBN/y) rats. Salt loading (with DOCA-salt) had no effect on ACE2 mRNA expression in normotensive SBN/y rats. Intriguingly, in SBH/y rats, salt loading and the development of hypertension were associated with a significant reduction in ACE2 mRNA expression as compared to normotensive SBN/y rats (FIG. 2a). Of note is that ACE2 mRNA was also lower in SBH/y fed regular diet when compared to SBN/y controls fed a similar diet. This latter finding is consistent with the 10-20 mmHg difference in blood pressure observed between SBH/y and SBN/y rats fed normal diet.

Figure 2B:
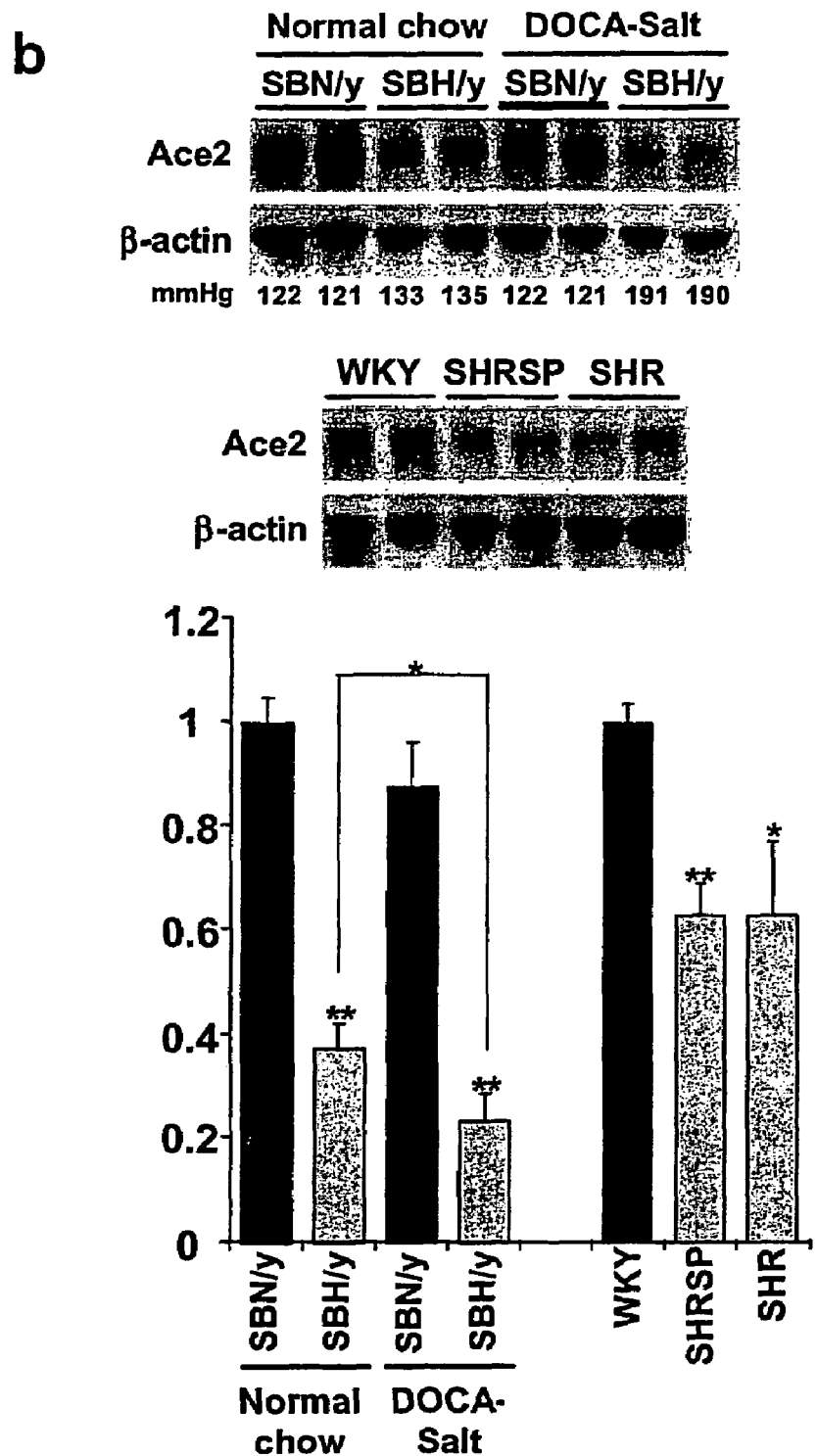

To measure ACE2 protein levels, an ACE2 (aa206-aa225 of mouse ACE2) specific rabbit antiserum was generated, which cross reacts with both rat and human ACE2 (not shown). In line with the decreased ACE2 mRNA expression, ACE2 protein expression was markedly reduced in SBH/y animals that were fed a normal diet (FIG. 2b). Increase in blood pressure of SBH/y rats following a 4-week diet of DOCA-salt correlated with further decreased ACE2 protein expression (FIG. 2b). Salt loading did not trigger increased blood pressure nor did it alter ACE2 expression in salt-resistant SBN/y control rats (FIG. 2b). ACE2 protein levels were also significantly decreased in the kidneys of spontaneously hypertensive SHRSP and SHR animals as compared to their WKY controls (FIG. 2b). Moreover, the levels of ACE2 mRNA were markedly reduced in hypertensive SHRSP and SHR rats (not shown). Cloning and sequencing of the coding region of ACE2 in the hypertensive rat strains did not reveal any sequence changes, indicating that reduced ACE2 expression likely results from polymorphisms that control ACE2 gene expression. The map position and reduced expression of ACE2 in three different rat strains indicate that ace2 is a strong candidate gene for this hypertensive QTL on the X-chromosome. Moreover, reduced ACE2 expression in all three hypertensive rat strains suggested that this enzyme functions as a negative regulator.

Cloning of Mouse ACE2 and Generation of ACE2 Knock-Out Mice

Figures 3B, 3C, 3D:
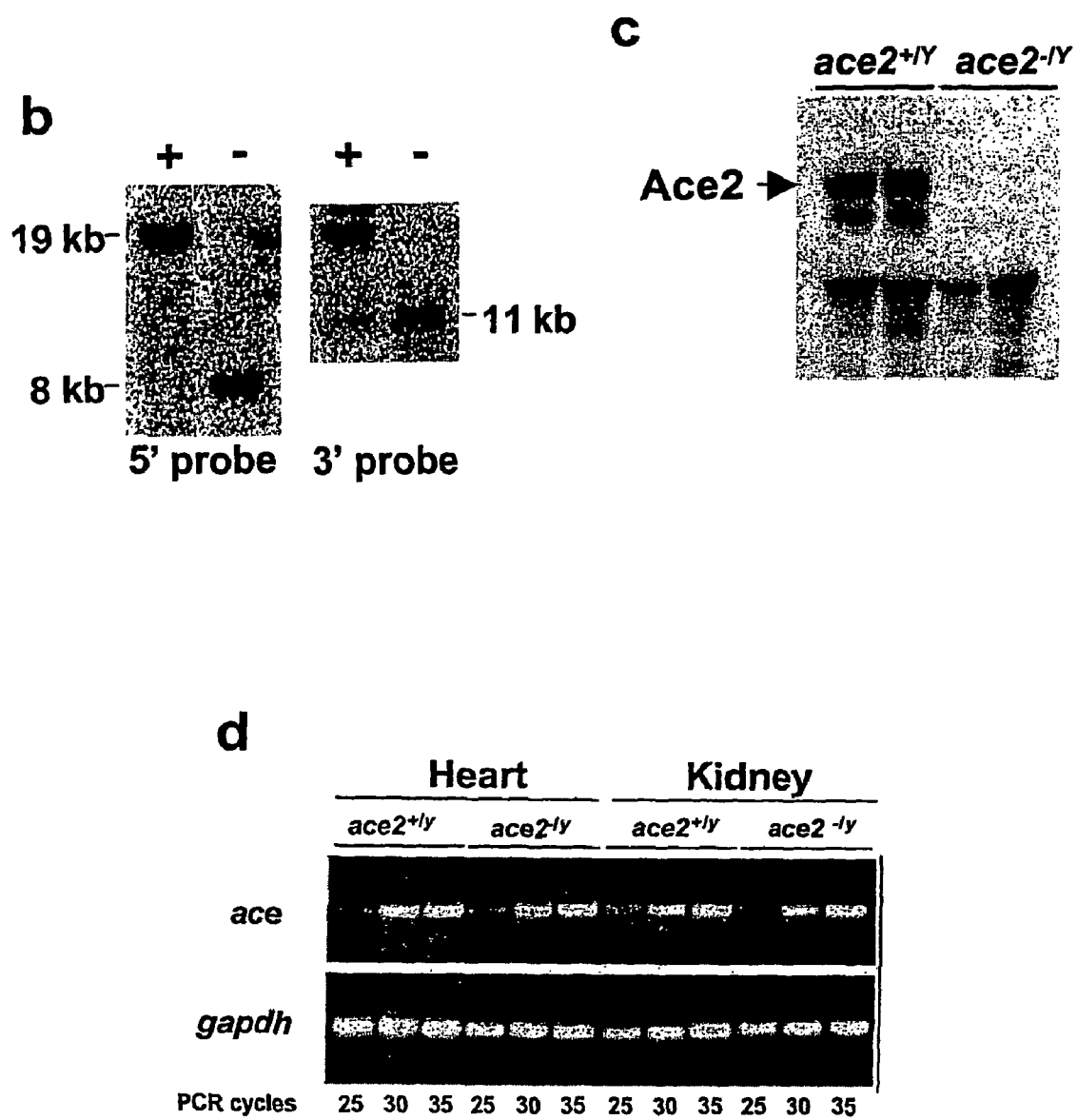

To validate the candidacy of ACE2 as a QTL and to test whether ACE2 has indeed an essential role in the cardiovascular physiology and the pathogenesis cardiovascular diseases, the mouse ACE2 gene was cloned (FIG. 1a). Similar to rat and human ACE2, murine ACE2 also maps to the X-chromosome (not shown) contains a single ACE-domain (FIG. 1b), and is predominantly expressed in the kidneys and heart (FIG. 1c). Interestingly, two isoforms for ACE2 in mouse was observed in all positive tissues. Overexpression of murine ACE2 in COS cells showed that ACE2 cleaves AngI into Ang1-9 (not shown) indicating that murine ACE2 has the same biochemical specificity as human ACE2. To determine the vivo role of ACE2, the ace2 gene in mouse was disrupted replacing exon 9 with a neomycin resistance gene effectively deleting the zinc binding catalytic domain (see Methods and FIG. 3a). Two ES-cell lines mutated at the ace2 locus were used to generate chimeric mice, which were backcrossed to C57BU6 to obtain germline transmission. Both mouse lines displayed identical phenotypes. Transmission of the ace2 mutation was confirmed by Southern blot analysis (FIG. 3b). The null mutation of ace2 was verified by the absence of ace2 mRNA transcripts and protein in Northern (not shown) and Western blot analyses (FIG. 3c). ACE mRNA expression in the kidneys and hearts was not altered in ace2 mutant mice (FIG. 3d).

Since the ACE2 gene maps to the X-chromosome, all male offspring were either null mutants (ace2$^{-/y}$) or wild type for ACE2 (ace2$^{+/y}$) whereas females were either wildtype (ace2$^{+/+}$), heterozygous (ace2$^{+/-}$), or homozygous (ace2$^{-/-}$) for the ace2 mutation. It should be noted that in all experiments described below, ace2$^{+/-}$ females behaved similar to ace2$^{+/+}$ females and ace2$^{+/y}$ males indicating that there is no apparent effect of ace2 heterozygosity. ACE2 null mice were born at the expected Mendelian frequency, appeared healthy, and did not display any gross detectable alterations in all organs analyzed. Moreover, in contrast to ace$^{-/-}$ male mice that display significantly reduced fertility, both male and female ace2 null mice are fertile.

Blood Pressure in Ace2 Mutant Mice

Figure 4A:
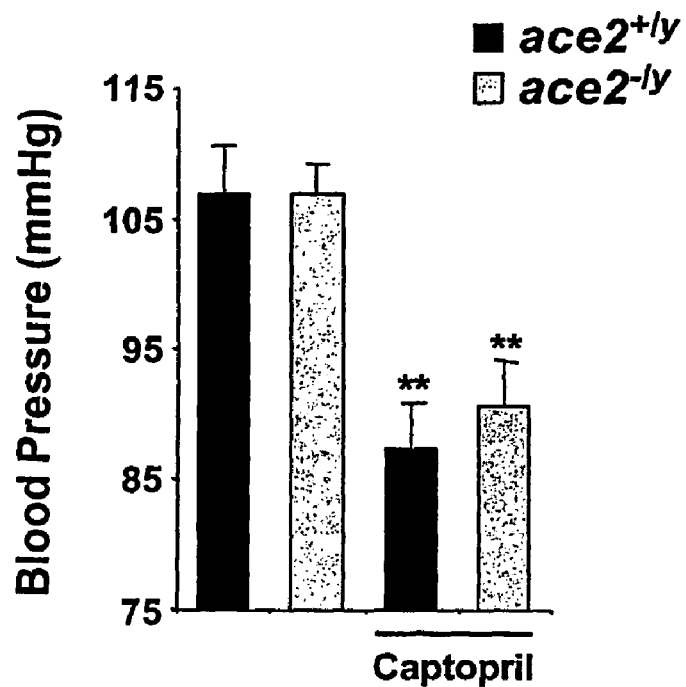

It has been previously shown that ace2 mutant mice display reduced blood pressure and kidney pathology. Therefore, it was first tested whether loss of ACE2 expression affects blood pressure homeostasis and/or kidney development or function. Intriguingly, loss of ACE2 did not result in alteration of blood pressure in 3-month old ace2$^{-/y}$ male (FIG. 4a) or ace2$^{-/-}$ female mice (not shown) as compared to their control littermates. Since it was possible that ACE could compensate for the loss of ACE2, we treated ace2-deficient mice with captopril which blocks ACE but not ACE2 function. However, in vivo inhibition of ACE with captopril reduced the blood pressure of ace$^{-/y}$ male mice to a similar extent as was observed in captopril treated wild-type littermates (FIG. 4a). Thus, even in a scenario of ACE inhibition, loss of ACE2 has no apparent direct effect on blood pressure homeostasis in this defined mouse background. Based on our RAS QTL data, we backcross our mutant mice to other mouse backgrounds to show the role of ACE2 in blood pressure control similar to genetic backgrounds in humans.

Impaired Kidney Function in Ace2 Mutant Mice

Figure 4B:
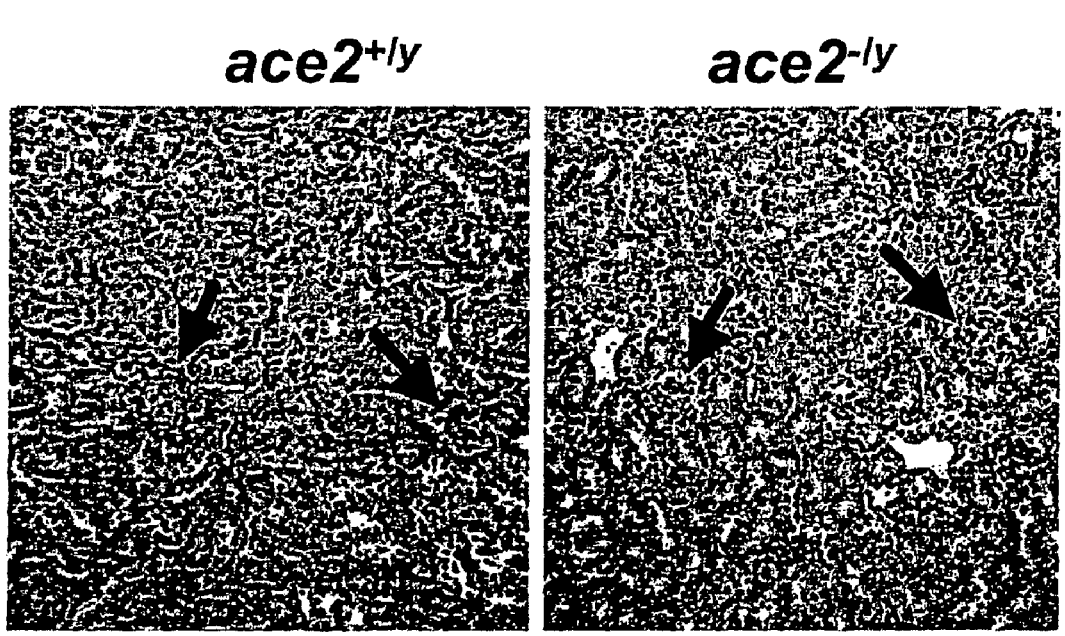

Since ACE2 is highly expressed in the kidneys, we examined kidney morphology and function. All 3 month old and 6 month old ace2$^{-/y}$ male and ace2$^{-/-}$ female mice displayed normal kidney morphology and no apparent changes in any kidney ultrastructures (FIG. 4b). Normal cellularity and kidney structures of the ductal system and glomeruli were also confirmed using serial section morphometry.

Kidneys from male ace2 deficient mice and age-matched littermate control mice were examined using light (PASstaining) and electron microscopy (TEM) at 3 and 12 months of age. The severity of sclerosis for each glomerulus was graded from 0 to 4+ in a blinded manner as follows: 0 represents no lesion, 1+sclerosis of<25% of the glomerulus, while 2+, 3+, and 4+represent sclerosis of 25 to 50%, 50 to 75%, and>75% of the glomerulus, respectively. At 3 months of age, there was no evidence of pathological changes in the kidneys from the ace2 deficient mice. However at 12 months of age, light microscopy revealed increased glomerular sclerosis/injury: 1.45±0.2 vs 0.25±0.06; n=6; p<0.01. Electron microscopy showed increased deposition of collagen fibrils in the renal mesangium and a thickened basement membrane. The chronic exposure to elevated AngII levels leads to hypoxia and oxidative stress in the kidneys from the ace2 deficient mice. Western blot analysis revealed increased expression of hypoxia inducible factor-1alpha (HIF1-α) and vascular endothelial growth factor (VEGF) in the kidneys from the ace2 deficient mice. The measurement of lipid peroxidation products showed increased degree of oxidative stress in the ace2 deficient mice at 6 months of age: hexanal (1001±161 vs 115±13 nmol/g; n=5; p<0.01) and malondialdehyde (48±6.4 vs 24.3±2.8 nmol/g; n=5; p<0.01).

These results show that the loss of ACE2 leads to enhanced angiotensin II signaling in a tissue-specific manner which ultimately mediates detrimental effects in the kidneys of the ace2 deficient mice. Decreased ACE2 expression plays an important pathological role in renal disease.

Loss of ACE2 Results in a Severe Defect in Heart Function

Pharmacological inhibition of ACE or AngII receptors suggested a role for the RAS in the regulation of heart function and cardiac hypertrophy. However, neither ace nor angiotensinogen null mice develop any overt heart disease. Since ACE2 is highly expressed in the vasculature of the heart, hearts of ace2-deficient mice were analyzed. Hearts of ace2 mutant mice display a slight wall thinning of the left ventricle and increased chamber dimensions (FIG. 5a). Thinning of the anterior left ventricular wall (AW) and increase in the left ventricle end diastolic dimension (LVEDD) in ace2-deficient hearts can be also seen by echocardiography (Table 1). These structural changes are primarily observed in 6 month old male mice. However, heart body weight ratios were comparable between age matched 3 month old (not shown) and 6 month old ace2$^{-/y}$ and ace2$^{+/y}$ mice (FIG. 5a,b). Echocardiography also showed that the left ventricle mass (LVM) and LVM/body weight ratios were normal (Table 1). Structural and biochemical changes characteristic of dilated cardiomyopathy were not observed as there was no indication of interstitial cardiac fibrosis (FIG. 5c,d) nor prototypical changes in ANF, BNP, a-MHC, b-MHC, and skeletal muscle actin gene expression (not shown). In addition, individual cardiomyocytes of ACE2 null mice exhibited no evidence of hypertrophy and we did not observe any evidence of altered cardiomyocyte apoptosis in ACE2 null mice as detected by TUNEL staining (not shown). Thus, despite mild dilation of hearts in 6 month old ACE2 null mice, there was no evidence of cardiac hypertrophy or dilated cardiomyopathy.

Figure 6A:
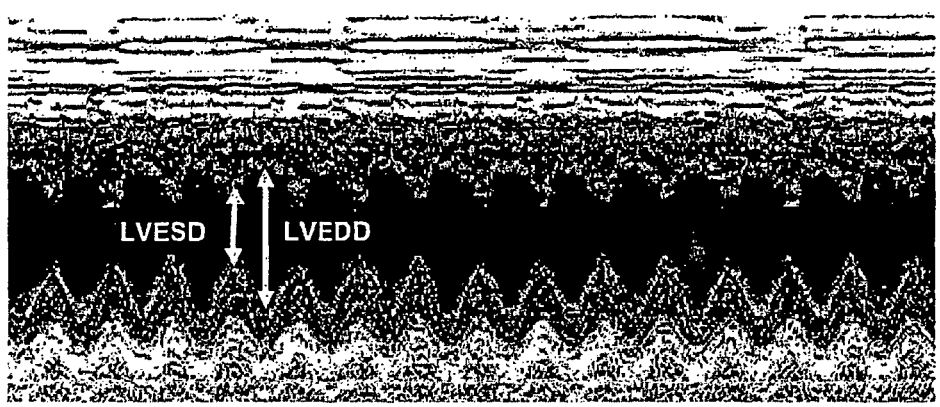
Figure 6A:
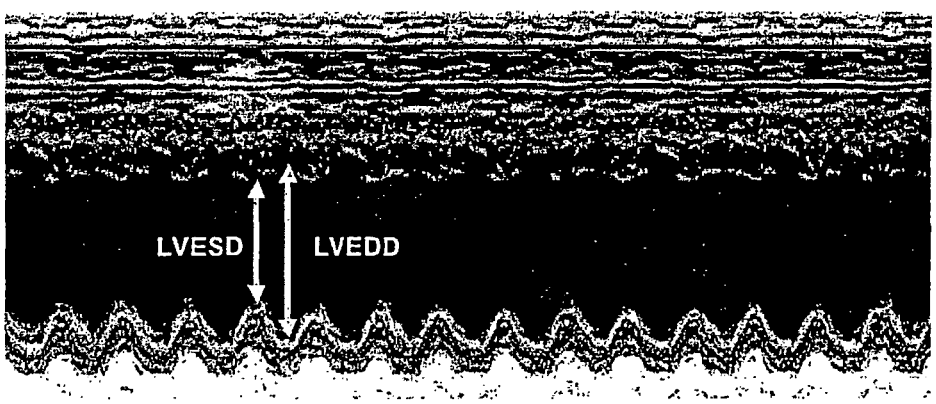
Figure 6A:
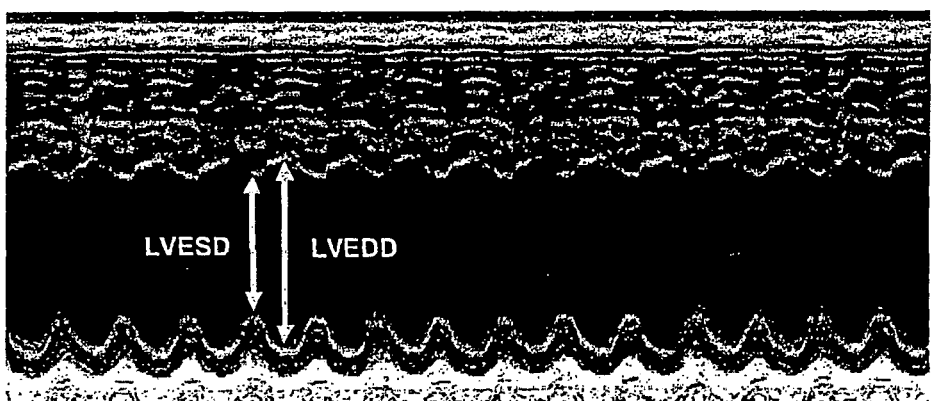
Figures 6B, 6C:
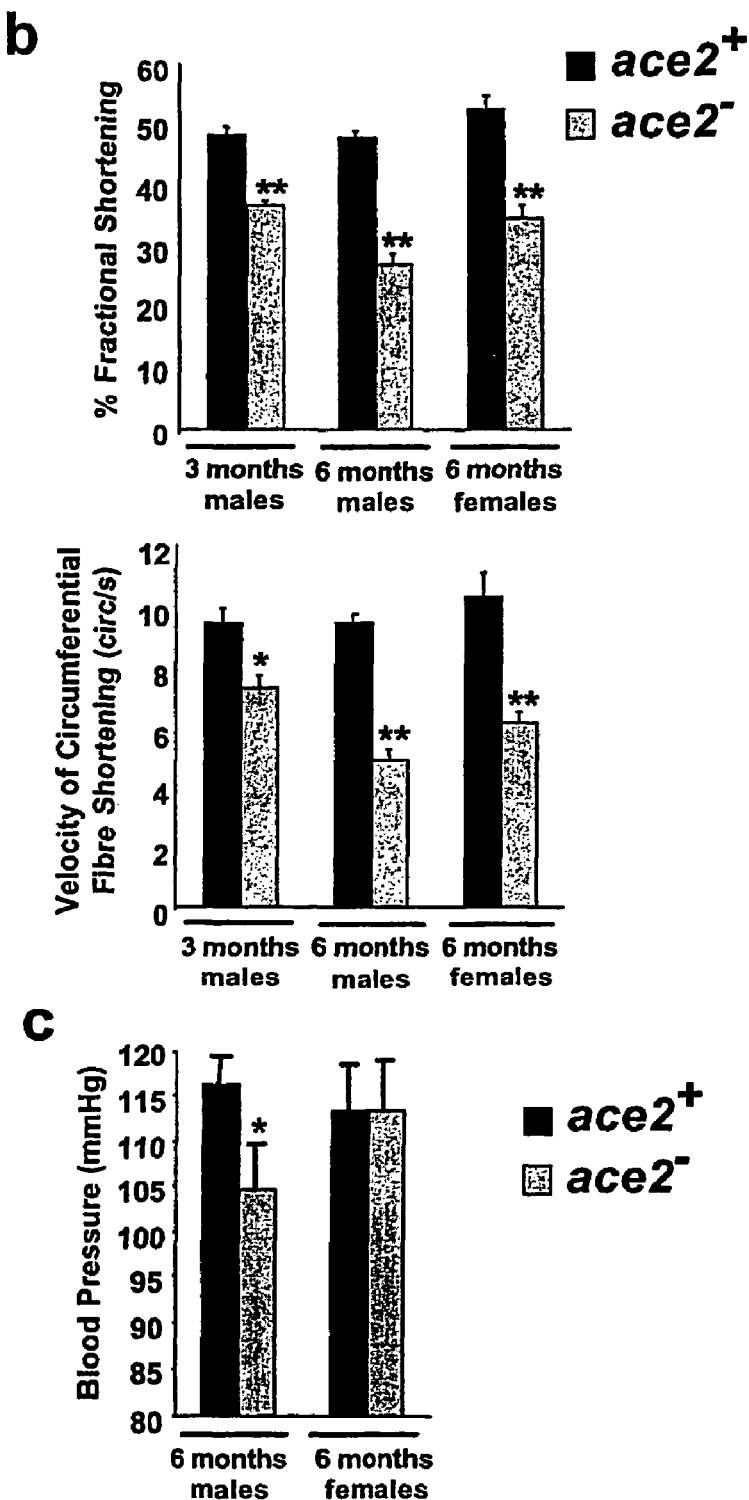

Interestingly, assessment of cardiac function by echocardiography revealed that all ace2$^{-/y}$ male and ace2$^{-/-}$ female mice exhibit severe contractile heart failure as determined by decreased fractional shortening (FS), and decreased velocity of circumferential fiber shortening (Table 1 and FIG. 6a,b). The decrease in function was found to be more severe in 6 month old male and female mice as compared to age matched 3 month old mice, suggesting a progression in the phenotype (Table 1). Consistent with the decreased cardiac contractility, 6 month old ace2$^{-/y}$ mice exhibited reduced blood pressure (FIG. 6c), a feature not found in age matched ace2$^{-/-}$ females and 3 month old males, suggesting that the reduction in blood pressure may be the result of severe cardiac dysfunction and not a direct effect of loss of ACE2 on systemic blood pressure. These surprising results show that ACE2 is a critical negative regulator of heart contractility.

To confirm the echocardigraphic defects in cardiac function, invasive hemodynamic measurements were performed in ace2 null mice. Importantly, invasive hemodynamic measurements showed that both dP/dT-max and dP/dT-min were markedly reduced in the ace2 mutant mice (Table 2), indicating severe impairment of contractile heart function. Loss of ACE2 also resulted in a significant decrease in aortic and ventricular pressures consistent with the observed reductions in cardiac contractility (Table 2). Remarkably, the data establish that the defects in cardiac contractility of ace2 mutant mice occur in the absence of any overt cardiac hypertrophy and can be genetically uncoupled from alterations in blood pressure.

Up-Regulation of Hypoxia-Inducible Genes in ace2 Null Mice

The severe contractile dysfunction and mild dilation in the absence of hypertrophy or cardiac fibrosis in ace2 null mice resembles cardiac stunning/hibernation in humans and animal models. Cardiac stunning and hibernation are adaptive responses to chronic hypoxia such as coronary artery disease or following bypass surgery. Since ACE2 is highly expressed in vascular endothelial cells but contractility is controlled by cardiomyocytes, it was speculated that loss of ACE2 could result in cardiac hypoxia. Therefore changes in the expression levels of hypoxia-inducible genes such as BNIP3[25] and PAI-1 were analyzed by Northern blotting. In the hearts of all ace2 null mice analyzed, mRNA expression of BNIP3 and PAI-1 were markedly up-regulated as compared to their wild-type littermates (FIG. 7a). Thus, loss of ACE2 results in the induction of a hypoxia-regulated gene expression profile.

Increased Angiotensin II Levels in tissues of ace2 Null Mice

Since ACE2 functions as a carboxypeptidase, cleaving a single residue from AngI, to generate Ang1-9, and a single residue form AngII to generate Ang1-7, it was hypothesized that ACE2 may function as a negative regulator of the RAS by competing with ACE for the substrate AngI and/or cleaving and inactivating AngII. If correct, loss of ACE2 should increase AngII levels in vivo. Using radioimmunoassays, AngII levels were indeed found to be significantly increased in the kidneys and hearts of ace2 mutant mice (FIG. 7b). In addition, an increase in AngI was also observed (FIG. 7b) consistent with AngI being a substrate of ACE2 action in vivo. No differences in ACE mRNA levels were found in the hearts and kidneys of ace2 mutant mice compared to controls indicating that the increased AngII tissue levels were not due to increased ACE expression (FIG. 3d). These data show that ACE2 functions as a negative regulator of the RAS and controlling endogenous levels of AngII.

Ablation of ACE Expression in ace2-Deficient Mice Rescues Heart Failure

If the phenotype in the hearts of ace2 mutant mice was due to the increase in AngII levels, then genetic ablation of ACE in combination with disruption of ACE2 may serve to reduce AngII levels and rescue the phenotype observed in the ACE2 mutant mice. To test this notion, ace/ace2 double mutant mice were generated. These double mutant mice were born at the expected Mendelian ratio and appear healthy. Blood pressure (FIG. 8a) and kidney defects (not shown) in the ace-ace2 double null mice were similar to that of ace single mutant mice. Fertility of the ace-ace2 double mutant mice was not addressed. Thus, loss of both ACE and ACE2 does not cause any apparent disease in addition to that seen in ace single mutant mice.

Since the heart function of ACE knockout mice has not been previously reported the heart parameters in these mice were first analyzed. In ace$^{-/-}$ mice, hearts are histologically normal (not shown) and no defect in heart function could be detected at 6 months of age (FIG. 8b,c). Importantly, ablation of ACE expression on an ace2 mutant background completely abolished the heart failure phenotype of ace2 single knockout mice (FIG. 8b,c). Moreover, using echocardiography, all heart functions of 6 month old, age matched ace-ace2 double mutant mice were comparable to that of their ace single mutant and wild type littermates (Table 1). Restoration of heart functions occurred in both male and female ace-ace2 double mutant mice. These genetic data show that ACE expression is required and necessary to trigger contractile heart failure in the absence of ACE2. Importantly, there was also no difference in blood pressure between ace and ace/ace2 knockout mice (FIG. 8a), further implying that the reduced blood pressure in older male ace2 mice is due to the dramatic decrease in heart function.

ACE2 Negatively Controls Lung Injury

Adult respiratory distress syndrome (ARDS) is a serious form of acute lung injury and has mortality rates of 40-70% even when intensive care is available. Trauma, severe sepsis (systemic infection), diffuse pneumonia and shock are the most serious causes of ARDS, and among them acid-induced lung injury is one of the most common causes. Potential mechanisms causing acid aspiration-associated lung injury include HCl-induced damage to the alveolar-capillary membrane, and polymorphonuclear neutrophil (PMN) adhesion, activation and sequestration, which results in pulmonary edema and the deterioration of gas exchange. Treatment for ARDS consists of mechanical ventilation and continuing treatment of the precipitating illness or injury. The supportive treatment using novel drugs protecting lung from further alveolar-capillary membrane damage would preserve the ARDS patients' lung function in order to treat the precipitating illness or injury, leading to a decrease in the mortality rate of ARDS.

Since ACE2 is expressed in lungs, we assessed whether loss of ACE2 has any role in acute lung injuries. FIG. 9 shows the changes in lung elastance (EL) in HCl-treated and control mice over a 3 hour period. Following HCl administration, wild type mice survived more than 4 hours, whereas ACE2 knockout mice died within 2-3 hours. Reflecting the difference of survival, ACE2 knockout mice showed a significantly more severe response in lung elastance than wild type mice. Thus, ACE2 plays a significant role in protecting lungs from acute acid-induced injury. Thus, enhancing ACE2 function and/or expression is a novel and unanticipated target for the treatment for ARDS and lung disease.

Methods

Cloning of mouse and rat ACE2 and chromosomal QTL mapping. Murine ACE2 was cloned from a proprietary EST database. Using a mouse ACE2 probe, we then screened a rat kidney cDNA (Invitrogen) to obtain a full-length rat cDNA as determined by DNA sequencing. For chromosomal mapping, a rat ACE2 cDNA specific probe was used to screen a rat PAC library (RPCI-31, Research Genetics), identifying two positive clones (6M6 and 125K9). The end sequences of these clones were determined and rat specific primers were designed (mc2L: 5'-TCAATTTACTGCTGAGGGGG-3', mc2R: 5'-GAGGGATAACCCAGTGCAAA-3') to determine the chromosomal map position of ACE2 in rat by screening a radiation hybrid panel (RH07.5, Research Genetics). SHR and control WKY rats were obtained from Harlan and maintained at the animal facilities of the Ontario Cancer Institute in accordance with institutional guidelines. Tissues from SHRSP rats were kindly provided by Dr. Detlev Ganten, Germany. Salt-resistant and salt-sensitive Sabra rats were bred and maintained at the animal facility of the Ben-Gurion University Barzilai Medical Center, Israel. Doca-salt treatment was as described previously.

Expression analysis. Total RNA was prepared form rat kidneys using tri-reagent. 20 mg of RNA was resolved on a 0.8% formamide gel. Blotted to nylon membrane (Amersham), and probed with a partial rat ACE2 cDNA clone (9-1). The β-actin probe and Multiple tissue Northern blots were purchased from Clontech. For western analysis, kidneys were homogenized in lysis buffer (50 mM Tris-HCl, pH 7.4, 20 mM EDTA, and 1% triton-X 100) supplemented with "Complete" protease inhibitor cocktail (Roche) and 1 mM Na$_3$VO$_4$. 100 mg of protein was resolved by SDS-PAGE on 8% trisglycine gels. ACE2 immuno-serum was obtained from rabbits immunized with a mouse specific ACE2 peptide DYEA-EGADGYNYNRNQLIED. The serum was affinity purified with the immunizing peptide using sulpho-link kit (Pierce). A commercially available β-actin antibody was used as loading control (Santa Cruz).

Generation of ACE2 mutant mice. A targeting vector (559 base pair short arm, and 8.1 kilobase long arm) was constructed using the pKO Scrambler NTKV-1907 vector (Stratagene). A portion of the ace2 genomic DNA containing nucleotides +1069 to +1299 was replaced with the neomycin resistance cassette in the anti-sense orientation. The targeting construct was electroporated into E14K ES cells, and screening for positive homologous recombinant ES clones was performed by Southern blotting of EcoRI-digested genomic DNA hybridized to 5' and 3' flanking probes. Two independent ace$^{-/y}$ ES cell lines were injected into C57BL/6-derived blastocysts to generate chimeric mice, which were backcrossed to C57BU6 mice. Two ES cell lines gave independent germline transmission. Data reported in this manuscript are consistent between the two mutant mouse lines. Ablation of ACE2 expression was confirmed by RT-PCR, Northern, and Western blot analyses. Only littermate mice were used for all experiments. Histology of all tissues, apoptosis assays, blood serology, and kidney morphometries were as described[31]. Complete ACE mutant mice have been previously described[8] and were obtained from Jackson Laboratories. Mice were maintained at the animal facilities of the Ontario Cancer Institute in accordance with institutional guidelines.

Heart morphometry, echocardiography, hemodynamics and blood pressure measurements. For heart morphometry, hearts were perfused with 10% buffered formalin at 60 mmHg and subsequently embedded in paraffin. Myocardial interstitial fibrosis was determined by quantitative morphometry using the color-subtractive computer assisted image analysis using Image Processing Tool Kit version 2.5 coupled with Photoshop 6.0 software. Picro-Sirius red stained sections were used to calculated interstitial fibrosis as the ratio of the areas with positive PSR staining compared to the entire visual field. Echocardiographic assessments were performed as described[32] using wild-type and mutant littermates. Mice were anesthetized with isoflourane/oxygen and examined by transthoracic echocardiography using a Acuson® Sequoia C256 equipped with a 15 MHz linear transducer. FS was calculated as: FS=[(EDD−ESD)/EDD]*100. Vcfc was calculated as FS/ejection time corrected for heart rate. Hemodynamics measurements were performed as described. Briefly, mice were anesthetized, and the right carotid artery was isolated and cannulated with a 1.4 French Millar catheter (Millar Inc., Houston) connected to an amplifier (TCP-500, Millar Inc.). After insertion of the catheter into the carotid artery, the catheter was advanced into the aorta and then into the left ventricle to record the aortic and ventricular pressures. The parameters measured and analyzed were heart rate, aortic pressure, left ventricular (LV) systolic pressure, LV diastolic pressure, and the maximum and minimum first derivatives of the LV pressure (+dP/dtmax and dP/dtmax, respectively). Tail-cuff blood pressure measurement were taken using a Visitech BP-2000 Blood Pressure Analysis System manufactured by Visitech Systems (Apex, N.C.). For captopril treatment, drinking water was supplemented with 400 mg/L captopril (Sigma) for two weeks prior to blood pressure measurement.

Tissue angiotensin peptide levels. Hearts and kidneys were homogenized on ice in 80% ethanol/0.1 N HCl containing the peptidase inhibitors described above including phenylmethylsulfonyl fluoride (PMSF, 100 µM). Protein homogenates were centrifuged at 30,000 g for 20 minutes, supernatants decanted, and acidified with 1% (v/v) heptafluorobutyric acid (HFBA, Pierce, Rockford, Ill.). The supernatant was concentrated to 5 ml on a Savant vacuum centrifuge (Savant, Farmingdale, N.Y.) and concentrated extracts were applied to activated Sep-Paks, washed with 0.1% HFBA, and eluted with 5 ml 80% methanol/0.1% HFBA. Radioimmunoassay analysis of angiotensin peptide content in the extracts from heart and kidney tissues was performed. The limits of detection for the Ang II and Ang I RIAs were 0.5 fmol/tube and Ang I 5 fmol/tube, respectively.

Acute lung injury model. ACE2 knockout mice and their littermates (8-12 weeks old) were used in this study. One minute before aspiration challenge, 2 deep inhalations (3 times tidal volume) were delivered to standardize volume history and measurements were made as baseline. Anesthetized and mechanically ventilated mice received intratracheal injection of 2 mL/kg HCl (pH=1.5), followed by a bolus of air. In the control group, mice received saline injection or no injection. In all groups, measurements were made at 30-minute intervals for 3 hours. To assess lung injury physiologically, lung elastance (EL; a reciprocal of lung compliance) was evaluated by measuring the tracheal peek pressure, flow, and volume. EL was calculated by dividing tracheal peek pressure with volume. Changes in EL reflect lung parenchymal alterations and stiffening of the lungs.

The present invention has been described in detail and with particular reference to the preferred embodiments; however, it will be understood by one having ordinary skill in the art that changes can be made without departing from the spirit and scope thereof. For example, where the application refers to proteins, it is clear that peptides and polypeptides may often be used. Likewise, where a gene is described in the application, it is clear that nucleic acid molecules or gene fragments may often be used.

All publications (including Genbank entries), patents and patent applications are incorporated by reference in their entirety to the same extent as if each individual publication, patent or patent application was specifically and individually indicated to be incorporated by reference in its entirety.

REFERENCES

Yusuf, S., Reddy, S., Ounpuu, S., & Anand, S. Global burden of cardiovascular diseases Part I: General considerations, the epidemiologic transition, risk factors, and impact of urbanization. *Circulation* 104, 2746-2753 (2001).

Carretero, O. A., & Oparil, S. Essential hypertension Part I: Definition and etiology. *Circulation* 101, 329-335 (2000).

Jacob, H. J. Physiological genetics: Application to hypertension research. *Clin. Exp. Pharm. Phys.* 26, 530-535 (1999).

Rapp, J. P. Genetic analysis of inherited hypertension in the rat. *Physiol. Rev.* 80,135-172 (2000).

Stoll, M. et al. A genomic-systems biology map for cardiovascular function. *Science* 294, 1723-1726 (2001).

Corvol, P., Williams, T. A. in *Handbook of Proteolytic Enzymes* (Barrett, A. J., Rawlings, N. D., and Woessner, J. F., eds) pp. 1066-1076. (Academic Press, London, 1998)

Skeggs, L. T., Dorer, F. E., Levine, M., Lentz, K. E., & Kahn J. R. The biochemistry of the renin-angiotensin system. *Adv. Exp. Med. Biol.* 130, 1-27 (1980).

Krege, J. H. et al. Male-female differences in fertility and blood pressure in ACE-deficient mice. *Nature* 375,146-148 (1995).

Esther, C. R. et al. Mice lacking angiotensin-converting enzyme have low blood pressure, renal pathology, and reduced male fertility. *Lab Invest.* 74, 953-965 (1996).

Wuyts, B., Delanghe, J., & De Buyzere, M. Angiotensin 1-converting enzyme insertion/deletion polymorphism: clinical implications. *Acta Clin. Belg.* 52, 338-49 (1997).

Elkind, M. S., & Sacco, R. L. Stoke risk factors and stroke prevention. *Semin. Neurol.* 18, 429-440 (1998).

Hollenberg, N. K. Angiotensin converting enzyme inhibition and the kidney. *Curr. Opin. Cardiol.* 3(Suppl 1), S19-29 (1988).

Garg, R., & Yusuf, S. Overview of randomized trials of angiotensin-converting enzyme inhibitors on mortality and morbidity in patients with heart failure. *JAMA.* 273, 1450-1456 (1995).

Tipnis, S. R. et al. A human homolog of angiotensin-converting enzyme. Cloning and functional expression as a captopril-insensitive carboxypeptidase. *J. Biol. Chem.* 275, 33238-33243 (2000).

Donoghue, M. et al. A novel angiotensin-converting enzyme-related carboxypeptidase (ACE2) converts angiotensin I to angiotensin 1-9. *Circ. Res.* 87, e1-e8 (2000)

Yagil C. et al. Role of chromosome X in the Sabra rat model of salt-sensitive hypertension. *Hypertension* 33(part II), 261-265 (1999).

Hilbert, P. et al. Chromosomal mapping of two genetic loci associated with blood-pressure regulation in hereditary hypertensive rats. *Nature* 353, 521-529 (1991).

Kloting, I., Voigt, B., Kovacs, P. Metabolic features of newly established congenic diabetes-prone BB.SHR rat strains. *Life Sci.* 62, 973-979 (1998).

Laragh, J. H. Renovascular hypertension: a paradigm for all hypertension. *J. Hypertension* 4(suppl. 4), S79-S88 (1986).

Yagil, C. et al. Development, genotype and phenotype of a new colony of the Sabra hypertension prone (SBH/y) and resistant (SBN/y) rat model of salt sensitivity and resistance. *J. Hypertension* 14, 175-82 (1996).

Tanimoto, K. et al. Angiotensinogen-deficient mice with hypotension. *J. Biol. Chem.* 269, 31334-31337 (1994).

Kloner, R. A., Bolli, R., Marban, E., Reinlib, L., & Braunwald, E. Medical and cellular implications of stunning, hibernation, and preconditioning: an NHLBI workshop. *Circulation* 97, 1848-1867 (1998).

Murphy, A. M. et al. Transgenic mouse model of stunned myocardium. *Science* 287, 488491 (2000).

Heusch, G. Hibernating myocardium. *Physiol Rev.* 78, 1055-1085 (1998).

Sowter, H. M., Ratcliffe, P. J., Watson, P., Greenberg, A. H., & Harris, A. L. HIF-1-dependent regulation of hypoxic induction of the cell death factors BNIP3 and NIX in human tumors. *Cancer Res.* 61, 6669-6673 (2001).

Kietzmann, T., Roth, U., & Jungermann, K. Induction of the plasminogen activator inhibitor-1 gene expression by mild hypoxia via a hypoxia response element binding the hypoxia-inducible factor-1 in rat hepatocytes. *Blood* 94, 4177-4185 (1999).

Taylor, C. A. M., Coates, D., & Shirras, A. D. The Acer gene in *Drosophilia* codes for an angiotensin-converting enzyme homologue. *Gene (Amst.)* 181, 191-197 (1996).

Giordano, F. J. et al. A cardiac myocyte vascular endothelial growth factor paracrine pathway is required to maintain cardiac function. *Proc. Natl. Acad. Sci.* 98, 5780-5785 (2001).

Weiss, D., Sorescu, D., & Taylor, W. R. Angiotensin II and atherosclerosis. *Am. J. Cardiol.* 87, 25C-32C (2001).

Enseleit, F., Hurlimann, D., & Luscher, T. F. Vascular protective effects of angiotensin converting enzyme inhibitors and their relation to clinical events. *J. Cardiovasc. Pharmacol.* 37(suppl. 1), S21-S30 (2001).

Kong, Y. Y. et al. OPGL is a key regulator of osteoclastogenesis, lymphocyte development and lymph-node organogenesis. *Nature* 397, 315-23 (1999).

Rothmann T. et al. Heart muscle-specific gene expression using replication defective recombinant adenovirus. Gene Ther 1996 October;3(10):919-26

Phillips M I et al. Vigilant vector: heart-specific promoter in an adeno-associated virus vector for cardioprotection. Hypertension 2002, February; 39(2 Pt 2):651-5

Herold B C et al. Herpes simplex virus as a model vector system for gene therapy in renal disease. Kidney Int 2002 January;61 Suppl 1:3-8

Figlin R A et al. Technology evaluation: interleukin-2 gene therapy for the treatment of renal cell carcinoma. Curr Opin Mol Ther 1999 April;1(2):271-8

Varda-Bloom N et al. Tissue-specific gene therapy directed to tumor angiogenesis. Gene Ther 2001 June;8(11):819-27

Scott-Taylor T H et al. Adenovirus facilitated infection of human cells with ecotropic retrovirus. Gene Ther 1998 May;5(5):621-9

Langer J C et al. Adeno-associated virus gene transfer into renal cells: potential for in vivo gene delivery. Exp Nephrol 1998 May-June;6(3):189-94

Lien Y H et al. Gene therapy for renal diseases. Kidney Int Suppl 1997 October;61:S85-8

Ohno K et al., Cell-specific targeting of Sindbis virus vectors displaying IgG-binding domains of protein A. Nat Biotechnol 1997 August;15(8):763-7

TABLE 1

Heart functions of ace2 null mice

| | 3 month - males | | 6 month - males | | 6 month - females | |
|---|---|---|---|---|---|---|
| | ace2$^{+/y}$ n = 7 | ace2$^{-/y}$ n = 7 | ace2$^{+/y}$ n = 8 | ace2$^{-/y}$ n = 8 | ace2$^{+/-}$ n = 3 | ace2$^{-/-}$ n = 3 |
| Heart Rate, bpm | 469 ± 12 | 466 ± 18 | 495 ± 15 | 482 ± 12 | 460 ± 6 | 452 ± 14 |
| AW, mm | 0.65 ± 0.02 | 0.62 ± 0.01 | 0.66 ± 0.01 | 0.59 ± 0.02* | 0.65 ± 0.02 | 0.57 ± 0.04 |
| LVEDD, mm | 4.09 ± 0.04 | 4.25 ± 0.10 | 4.12 ± 0.10 | 4.49 ± 0.12* | 3.71 ± 0.10 | 4.11 ± 0.07* |
| LVESD, mm | 2.11 ± 0.04 | 2.69 ± 0.09** | 2.13 ± 0.06 | 3.29 ± 0.14** | 1.74 ± 0.07 | 2.68 ± 0.11** |
| % FS | 48.42 ± 1.14 | 36.73 ± 0.89** | 48.12 ± 0.84 | 26.76 ± 1.78** | 53.00 ± 1.68 | 34.85 ± 1.76** |
| PAV, M/s | 0.992 ± 0.029 | 0.922 ± 0.033 | 0.902 ± 0.044 | 0.802 ± 0.037 | 0.875 ± 0.048 | 0.809 ± 0.044 |
| Vcfc, circ/s | 9.49 ± 0.48 | 7.28 ± 0.45* | 9.46 ± 0.26 | 4.93 ± 0.33** | 10.34 ± 0.81 | 6.16 ± 0.31** |
| LVM, mg | 95.69 ± 1.88 | 95.50 ± 2.28 | 102.41 ± 4.00 | 100.49 ± 3.39 | 92.27 ± 2.02 | 89.60 ± 1.54 |
| LVM/BW, mg/g | 3.32 ± 0.08 | 3.53 ± 0.18 | 3.19 ± 0.10 | 3.32 ± 0.15 | 3.29 ± 0.37 | 3.30 ± 0.09 |

*p < 0.05 ace2$^{-/y}$ vs ace2$^{+/y}$ or ace2$^{-/-}$ vs ace2$^{+/-}$
**p < 0.01 ace2$^{-/y}$ vs ace2$^{+/y}$ or ace2$^{-/-}$ vs ace2$^{+/-}$
Bpm = heart beats per minute;
AW = anterior wall thickness;
LVEDD = left ventricle end diastolic dimension;
LVESD = left ventricle end systolic dimension;
% FS = percent fractional shortening;
PAV = peak aortic outflow velocity;
Vcfc = Velocity of circumferential fiber shortening;
LVM = calculated left ventricular mass;
BW = body weight.

Wickenden, A. D. et al. Targeted expression of a dominant-negative K(v)4.2 K(+) channel subunit in the mouse heart. *Circ. Res.* 85, 1067-1076 (1999).

Zvaritch, E. et al. The transgenic expression of highly inhibitory monomeric forms of phospholamban in mouse heart impairs cardiac contractility. *J. Biol. Chem.* 275, 14985-14991 (2000).

Rosengart et al. U.S. Pat. No. 6,322,536

March et al. U.S. Pat. No. 6,224,584

Hammond et al. U.S. Pat. No. 6,174,871

Wolfgang-M. Franz et al. Analysis of tissue-specific gene delivery by recombinant adenoviruses containing cardiac-specific promoters. Cardiovascular Research 35(1997) 560-566

TABLE 2

Invasive hemodynamic parameters of 6 months old ace2$^{-/y}$ mice

| | ace2$^{+/y}$ N = 8 | ace2$^{-/y}$ N = 8 |
|---|---|---|
| Heart rate, bpm | 303 ± 16 | 298 ± 8 |
| SBP, mmHg | 111.5 ± 2.4 | 91.6 ± 3.0 |
| DBP, mmHg | 70.5 ± 3.0 | 50.3 ± 2.4** |
| MBP, mmHg | 84.2 ± 2.8 | 64.0 ± 2.6** |
| LVSBP, mmHg | 107.4 ± 4.5 | 87.5 ± 2.3** |
| LVEDBP, mmHg | 5.5 ± 0.8 | 5.3 ± 0.7 |

TABLE 2-continued

Invasive hemodynamic parameters of 6 months old ace2$^{-/y}$ mice

|  | ace2$^{+/y}$ N = 8 | ace2$^{-/y}$ N = 8 |
|---|---|---|
| dP/dT max | 5579 ± 422 | 3034 ± 124** |
| dP/dT min | −5055 ± 257 | −2929 ± 271** |

**p < 0.01 ace2$^{-/y}$ vs ace2$^{+/y}$
SBP = systolic blood pressure;
DBP = diastolic blood pressure;
MBP = mean arterial blood pressure;
LVSBP = left ventricle systolic blood pressure;
LVEDBP = left ventricle end diastolic blood pressure;
dP/dT max = maximum 1st derivative of the change in left ventricular pressure/time;
dP/dT min = minimum 1$^{st}$ derivative of the change in left ventricular pressure/time

TABLE 3

Heart functions of 6 months old ace and ace/ace2 null mice

|  | ace$^{-/-}$ n = 8 | ace$^{-/-}$ace2$^{-/y}$ n = 8 |
|---|---|---|
| Heart Rate, bpm | 507 ± 17 | 491 ± 10 |
| AW, mm | 0.63 ± 0.01 | 0.65 ± 0.02 |
| LVEDD, mm | 3.86 ± 0.04 | 3.79 ± 0.07 |
| LVESD, mm | 2.11 ± 0.04 | 2.13 ± 0.07 |
| % FS | 45.34 ± 1.11 | 43.95 ± 1.24 |
| PAV, M/s | 0.995 ± 0.064 | 0.931 ± 0.040 |
| Vcfc, circ/s | 8.94 ± 0.25 | 8.40 ± 0.27 |

AW = anterior wall thickness;
LVEDD = left ventricle end diastolic dimension;
LVESD = left ventricle end systolic dimension;
% FS = percent fractional shortening;
PAV = peak aortic outflow velocity;
Vcfc = Velocity of circumferential fiber shortening.

We claim:

1. A method of treating acute respiratory distress syndrome in a mammal comprising administering a mammalian ACE2 polypeptide to the mammal, wherein the acute respiratory distress syndrome is treated.

2. The method of claim 1, wherein the ACE2 polypeptide is a mouse ACE2 polypeptide.

3. The method of claim 1, wherein the ACE2 polypeptide is a rat ACE2 polypeptide.

4. The method of claim 1, wherein the ACE2 polypeptide is a human ACE2 polypeptide.

5. The method of claim 1, wherein the mammal is a human.

6. The method of claim 1, further comprising administering an ACE inhibitor to the mammal.

* * * * *